US010377791B2

(12) United States Patent
Eloranta et al.

(10) Patent No.: US 10,377,791 B2
(45) Date of Patent: Aug. 13, 2019

(54) THERAPEUTICALLY ACTIVE ESTRATRIENTHIAZOLE DERIVATIVES AS INHIBITORS OF 17 B-HYDROXYSTEROID DEHYDROGENASE, TYPE 1

(71) Applicant: FORENDO PHARMA LTD, Turku (FI)

(72) Inventors: Maire Eloranta, Oulu (FI); Leena Hirvelä, Oulu (FI); Lauri Kangas, Lieto (FI); Pasi Koskimies, Turku (FI); Risto Lammintausta, Turku (FI); Mikko Unkila, Turku (FI)

(73) Assignee: FORENDO PHARMA LTD., Turku (FI)

( * ) Notice: Subject to any disclaimer, the term of this patent is extended or adjusted under 35 U.S.C. 154(b) by 0 days.

(21) Appl. No.: 14/392,289

(22) PCT Filed: Jun. 25, 2014

(86) PCT No.: PCT/FI2014/050517
§ 371 (c)(1),
(2) Date: Dec. 23, 2015

(87) PCT Pub. No.: WO2014/207309
PCT Pub. Date: Dec. 31, 2014

(65) Prior Publication Data
US 2017/0114090 A1    Apr. 27, 2017

(30) Foreign Application Priority Data
Jun. 25, 2013    (FI) .................................... 20135693

(51) Int. Cl.
| A61K 31/58 | (2006.01) |
| C07J 43/00 | (2006.01) |
| C07J 71/00 | (2006.01) |
| A61K 31/704 | (2006.01) |
| C07J 51/00 | (2006.01) |

(52) U.S. Cl.
CPC ........... *C07J 71/0063* (2013.01); *A61K 31/58* (2013.01); *A61K 31/704* (2013.01); *C07J 43/003* (2013.01); *C07J 51/00* (2013.01); *C07J 71/0057* (2013.01)

(58) Field of Classification Search
CPC .. C07J 43/003; C07J 71/0057; C07J 71/0063; A61K 31/58; A61K 31/704
See application file for complete search history.

(56) References Cited

U.S. PATENT DOCUMENTS

2006/0281710 A1    12/2006  Messinger et al.
2008/0255075 A1    10/2008  Messinger et al.

FOREIGN PATENT DOCUMENTS

| JP | 2004-537499 | 12/2004 |
| WO | WO 99/046279 | 9/1999 |
| WO | WO 00/007996 | 2/2000 |
| WO | WO 01/042181 | 6/2001 |
| WO | WO 2002/42319 A2 | 5/2002 |
| WO | WO 03/022835 | 3/2003 |
| WO | WO 03/033487 | 4/2003 |
| WO | WO 04/046111 | 6/2004 |
| WO | WO 04/060488 | 7/2004 |
| WO | WO 04/085345 | 10/2004 |
| WO | WO 04/085457 | 10/2004 |
| WO | WO 04/110459 | 12/2004 |
| WO | WO 05/032527 | 4/2005 |
| WO | WO 05/047303 | 5/2005 |
| WO | WO 05/084295 | 9/2005 |
| WO | WO 06/003012 | 1/2006 |

(Continued)

OTHER PUBLICATIONS

P. Brozic, T. Lanisnik Rizner and S. Gobec, "Inhibitors of 17β-Hydroxysteroid Dehydrogenase Type 1", *Current Medicinal Chemistry*, vol. 15, No. 2, pp. 137-150; (2008).

Koffman et al., "Evidence for Involvement of Tyrosine in Estradiol Binding by Rat Uterus Estrogen Receptor", *J. Steroid Biochem. Molec. Biol.*, vol. 38, No. 2, pp. 135-139, 1991.

Laplante et al., "Estradiol and estrone C-16 derivatives as inhibitors of type 1 17β-hydroxysteroid dehydrogenase: Blocking of ER+breast cancer cell proliferation induced by estrone", *Bioorganic & Medicinal Chemistry*, vol. 16, pp. 1849-1860 (2008).

(Continued)

*Primary Examiner* — Barbara P Badio
(74) *Attorney, Agent, or Firm* — Brinks Gilson & Lione

(57) ABSTRACT

The invention relates to compounds of formula (I) and pharmaceutically acceptable salts thereof wherein R1 to R6 are as defined in the claims. The invention further relates to their use as inhibitors of 17β-HSD and in treatment or prevention of steroid hormone de-pendent diseases or disorders, such as steroid hormone dependent diseases or disorders requiring the inhibition of the 17β-HSD1 enzyme and/or requiring the lowering of the endogenous estradiol concentration. The present invention also relates to the preparation of the aforementioned compounds and to pharmaceutical compositions comprising as an active ingredient(s) one or more of the aforementioned compounds or pharmaceutically acceptable salts thereof.

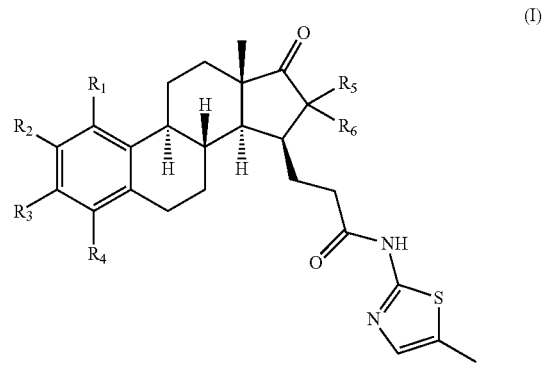

16 Claims, No Drawings

(56) References Cited

FOREIGN PATENT DOCUMENTS

| WO | WO 06/003013 | 1/2006 |
|---|---|---|
| WO | WO 06/027347 | 3/2006 |
| WO | WO 06/125800 | 11/2006 |
| WO | WO 08/034796 | 3/2008 |
| WO | WO 08/065100 | 6/2008 |
| WO | WO 12/129673 | 10/2012 |

OTHER PUBLICATIONS

Messinger et al., "Estrone C15 derivatives-A new class of 17β-hydroxysteroid dehydrogenase type 1 inhibitors", *Molecular and Cellular Endocrinology*, vol. 301, pp. 216-224, (2009).

Moller et al., "Structure-based design, synthesis and in vitro characterization of potent 17β-hydroxysteroid dehydrogenase type 1 inhibitors based on 2-substitutions of estrone and D-homo-estrone", *Bioorganic & Medicinal Chemistry Letters*, vol. 19, pp. 6740-6744, (2009).

Möller et al., "Species Used for Drug Testing Reveal Different Inhibition Susceptibility for 17 beta-Hydroxysteroid Dehydrogenase Type 1", *PLoS ONE*, vol. 5, Issue 6, pp. 1-11; (Jun. 2010).

Poirier, Donald, "Inhibitors of 17β-Hydroxysteroid Dehydrogenases", *Current Medicinal Chemistry*, vol. 10, No. 6; pp. 453-477; (2003).

Poirier, Donald, "17β-Hydroxysteroid dehydrogenase inhibitors: a patent review", *Expert Opin. Ther. Patents*, 20(9), pp. 1123-1145; (2010).

Puranen et al., "Site-directed mutagenesis of the putative active site of human 17β-hydroxysteroid dehydrogenase type 1", *Biochem. J.*, 304; pp. 289-293; (1994).

International Search Report and Written Opinion of PCT/FI2014/050517, dated Jul. 10, 2014.

Search Report for Finnish Patent Application No. 20135693, dated Feb. 12, 2014.

Japanese Office Action for JP 2016-522678, dated May 9, 2018 (10 pages).

Gillian M. Allan et al., "Modification of Estrone at the 6, 16, and 17 Positions: Novel Potent Inhibitors of 17β-Hydroxysteroid Dehydrogenase Type 1," J. Med. Chem. 2006, 49, pp. 1325-1345.

THERAPEUTICALLY ACTIVE ESTRATRIENTHIAZOLE DERIVATIVES AS INHIBITORS OF 17 B-HYDROXYSTEROID DEHYDROGENASE, TYPE 1

FIELD OF THE INVENTION

The present relates to novel estrone C-15 thiazole derivatives, to their pharmaceutically acceptable salts, and their use in therapy. The invention further relates to pharmaceutical compositions comprising these compounds as active ingredients.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestrosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy pre-menopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is down-regulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 17β-HSD's have been disclosed in WO 2001/42181, WO 2003/022835, WO 2003/033487, WO 2004/046111, WO 2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogen-dependent diseases that can be influenced by the inhibition of the 17β-hydroxysteroid dehydrogenase type 1. Similarly WO2006/003013 presents 2-substituted estratrienones usable for preventing and treating estrogen-dependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3, 15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

BRIEF DESCRIPTION OF THE INVENTION

An object of the present invention is to provide compounds useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

One of the problems associated with the known 17β-HSD1 inhibitors is the disposition, in particular the metabolic stability, of the compounds. It is therefore yet a further object of the present invention to provide compounds with improved metabolic stability.

The present invention provides novel compounds of formula (I)

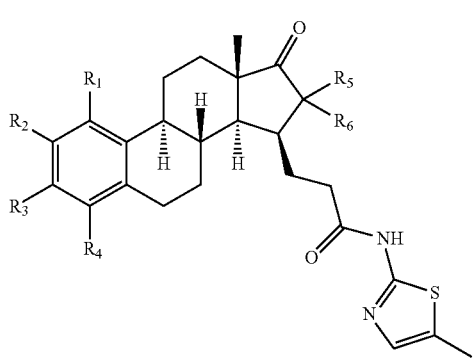

(I)

wherein (i) R1 is selected from the group consisting of H, $NO_2$, OH, and $N(R')_2$;

(ii-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR", C(=NH)R", C(=N—OH)R" and COR";

R3 is selected from the group consisting of H, $C_{1-6}$-alkyl, $C_{1-3}$-haloalkyl, $C_{1-3}$-perhaloalkyl, $NR'_2$, $N_3$, and $OR_3'$, wherein $R_3'$ is selected from the group consisting of R', benzyl, succinyl, optionally acylated glucuronyl, $(CH_2)_nOH$, $SO_2OH$, $SO_2R"$, tosyl, $SO_2N(R')_2$, $PO(OR')_2$, COOR''', $C(O)N(R')_2$, $C(O)(CH_2)_nN(R')_2$, $C(O)CH_2NHC(O)R'$, $C(O)CH_2NHC(O)OR"$ and C(O)R''';

wherein

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R" is $C_{1-6}$-alkyl, $C_{1-3}$-haloalkyl, or $C_{1-3}$-perhaloalkyl;

R''' is $C_{1-18}$-alkyl, $C_{2-18}$-alkenyl, —$(CH_2)_n$—$C_{3-6}$-cycloalkyl, or phenyl optionally substituted with acetoxy; and n is 1 or 2; or (ii-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(iii) R5 and R6 are each independently selected from the group consisting of H, halogen, OH, $C_{1-3}$-alkoxy, and CHO, or R5 and R6 form together =CH—OH;

provided that when R1, R2, R4, R5 and R6 are H, R3 is not OH or methoxy;

or a pharmaceutically acceptable salt thereof.

Compounds of the present invention may be useful in therapy, especially in the treatment or prevention of steroid hormone dependent diseases or disorders requiring the lowering of the endogenous estradiol concentration or the inhibition of 17β-HSD enzymes, in animals, in particular mammals, and humans. In particular, compounds of formula (I) represent inhibitors of the 17β-HSD1 enzyme, possessing pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome or lower urinary tract syndrome. Further estrogen-dependent diseases which may be treated and/or prevented with an effective amount of a compound of the invention include multiple sclerosis, obesity, rheumatoid arthritis, colon cancer, tissue wounds, skin wrinkles and cataracts. The compounds of the present invention typically have an inhibitory activity at the 17-β-HSD1 enzyme in the IC50 range of 0.1 nM to 1 μM. The inhibitory activity can be measured as explained in context of the experimental examples.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compound of formula (I) or a pharmaceutically acceptable salt thereof for use in the treatment of estradiol dependent malign or benign diseases and disorders.

DETAILED DESCRIPTION OF THE INVENTION

Compounds of the invention contain steroidal core structure having a defined stereochemistry that is the natural configuration of estrogens.

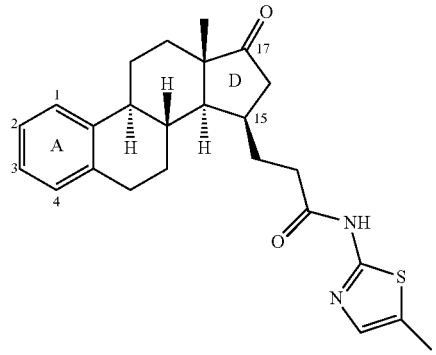

Compounds of the invention bear a methyl thiazolyl side chain at C15 in β-configuration which, together with the specific substitution pattern of the A and/or D ring(s), provides the inventive properties of compounds of the present invention. In addition to the stereochemistry of the steroidal core, the compounds of formula (I) may poses at least one further asymmetric carbon atom at C16. Thus compounds of the invention may exist in racemic form or optically active forms in respect to this carbon atom. All these forms are encompassed by the present invention.

The term "halogen" as used herein and hereafter by itself or as part of other groups refers to the Group VIIa elements and includes F, Cl, Br and I groups.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-6}$-alkyl has 1 to 6 carbon atoms in the alkyl moiety and thus, for example, $C_{1-4}$-alkyl includes methyl, ethyl, n-propyl, isopropyl, n-butyl, sec-butyl, isobutyl, tert-butyl and $C_{1-6}$-alkyl additionally includes branched and straight chain pentyl and hexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "$C_{3-6}$-cycloalkyl" as used herein and hereafter refers to cycloalkyl groups having 3 to 6 carbon atoms and thus includes cyclopropyl, cyclobutyl, cyclopentyl, and cyclohexyl.

The term "alkylenyl" as used herein and hereafter, is a divalent group derived from a straight or branched chain hydrocarbon of having suitably 1 to 6 carbon atoms. Representative examples of alkylenyl include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkenyl" as used herein and hereafter is an unsaturated linear or branched hydrocarbon group having at least one olefinic double bond between any two carbon atoms and having the indicated number of carbon atoms, for example $C_{2-6}$-alkenyl has 2 to 6 carbon atoms in the alkenyl moiety, such as ethenyl, propenyl, butenyl, pentenyl, and hexenyl. Examples of preferred alkenyls groups include, but are not limited to, linear alkenyl groups having a terminal double bond such as vinyl and allyl groups.

The term "$C_{2-6}$-alkynyl" as used herein is an unsaturated linear or branched hydrocarbon group having at least one olefinic triple bond between any two carbon atoms, such as ethynyl, propynyl, butynyl, pentynyl, and hexynyl. Examples of preferred alkynyl groups include, but are not limited to, linear alkynyls groups having a terminal triple bond.

The term "$C_{1-6}$-alkoxy" as used herein and hereafter refers to a —O—($C_{1-6}$-alkyl) group where the "$C_{1-6}$-alkyl" has the above-defined meaning. Examples of preferred alkoxy groups include, but are not limited to, methoxy, ethoxy, and iso-propyloxy.

The term "an 5 to 6 membered aliphatic or aromatic heterocyclic ring" refers to a monocyclic ring, which may be aliphatic or aromatic and comprises 1 or 2 heteroatoms each independently selected from N and O while the remaining ring atoms are carbon atoms. Representing groups include pyrrolidinyl, piperidinyl, morpholinyl, and piperazinyl, especially morpholinyl.

The term "an unsaturated or aromatic 5-membered heterocyclic ring" refers to a monocyclic ring which may be aromatic or unsaturated and comprises 1 or 2 heteroatoms each independently selected from N and O, while the remaining ring atoms are carbon atoms. The ring may be optionally substituted one or more times, in particular one time, with methyl at any suitable ring atom, including N, or with oxo at any suitable ring carbon atom. Preferred groups include, but are not limited to, oxazolone or and 1,3-oxazole, optionally substituted with methyl.

The term "optionally substituted" as used herein and hereafter in context of a phenyl group denotes phenyl that is either unsubstituted or substituted independently with one or more, in particular 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen, $C_{1-4}$-alkyl, in particular methyl; OH; $C_{1-4}$-alkoxy, in particular methoxy; CN; $NO_2$; and acetoxy. Preferably said phenyl is optionally substituted with acetoxy.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The present invention relates to estrone C-15 thiazole compounds having formula (I)

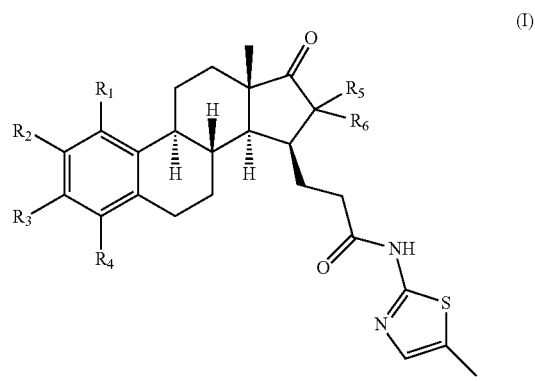

(I)

wherein (i) R1 is selected from the group consisting of H, $NO_2$, OH, and $N(R')_2$;

(ii-a) R2 and R4 are each independently selected from the group consisting of H, halogen, $C_{1-8}$-alkyl, $C_{1-3}$-haloalkyl, $C_{1-3}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR'', C(=NH)R'', C(=N—OH)R'' and COR'';

R3 is selected from the group consisting of H, $C_{1-8}$-alkyl, $C_{1-3}$-haloalkyl, $C_{1-3}$-perhaloalkyl, $NR'_2$, $N_3$, and $OR_3'$, wherein $R_3'$ is selected from the group consisting of R', benzyl, succinyl, optionally acylated glucuronyl, $(CH_2)_nOH$, $SO_2OH$, $SO_2R''$, tosyl, $SO_2N(R')_2$, $PO(OR')_2$, COOR''', $C(O)N(R')_2$, $C(O)(CH_2)_nN(R')_2$, $C(O)CH_2NHC(O)R'$, $C(O)CH_2NHC(O)OR''$ and $C(O)R'''$;

wherein

R' is H or $C_{1-8}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R'' is $C_{1-8}$-alkyl, $C_{1-3}$-haloalkyl, or $C_{1-3}$-perhaloalkyl;

R''' is $C_{1-18}$-alkyl, $C_{2-18}$-alkenyl, $-(CH_2)_n-C_{3-8}$-cycloalkyl, or optionally substituted phenyl; and n is 1 or 2; or (ii-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(iii) R5 and R6 are each independently selected from the group consisting of H, halogen, OH, $C_{1-3}$-alkoxy, and CHO, or R5 and R6 form together =CH—OH;

provided that when R1, R2, R4, R5 and R6 are H, R3 is not OH or methoxy;

or a pharmaceutically acceptable salt thereof.

In an embodiment of the invention, the invention relates to a compound of formula (I) as defined herein, provided that when R3 is OH or methoxy and R2 is $C_{1-6}$-alkyl, one of R1 and R4 is other than H. In a further embodiment of the invention, the invention relates to a compound of formula (I) as defined herein, provided that when R3 is OH, $C_{1-6}$-alkoxy or benzyloxy, and R2 is $C_{1-6}$-alkyl or $C_{1-6}$-alkoxy, one of R1 and R4 is other than H.

In an embodiment of the invention, the invention relates to a compound of formula (I) wherein R1 is H or $NO_2$, in particular H. In a further embodiment of the present invention the invention relates to a compound of formula (I) wherein R5 and R6 are each independently selected from H and halogen, in particular both are H.

In one embodiment of the invention, the invention relates to a compound of formula (I), wherein R2 is selected from the group consisting of H, halogen, branched $C_{3-6}$-alkyl, CN, $NO_2$, $NH_2$, $(CH_2)N(R')_2$, COR'' and OH, wherein R' is methyl or both R's together with the nitrogen they are attached to form an 5 to 6 membered aliphatic or aromatic heterocyclic ring comprising 1 or 2 heteroatoms each independently selected from N and O, such as pyridinyl.

In another embodiment of the invention, R3 is selected from the group consisting of H, $OR_3'$, wherein $R_3'$ is as defined in above, preferably $R_3'$ is selected from the group consisting of R' and $C(O)R'''$.

In a further embodiment of the invention, the invention relates to a compound of formula (I), wherein R4 is selected from the group consisting of H, halogen, $NO_2$, $NH_2$, CN, and $NHCOCF_3$.

In yet another embodiment of the invention, the invention relates to a compound of formula (I) wherein R1, R5 and R6 are each H and which compound has the formula (Ia)

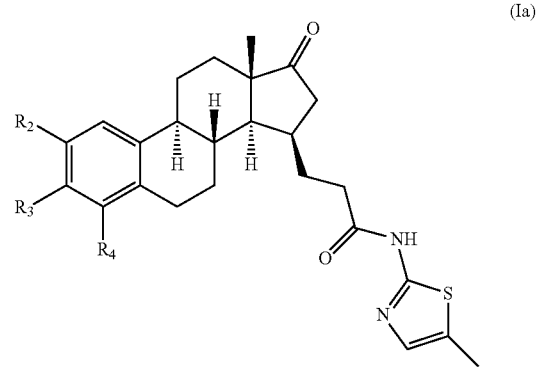

(Ia)

wherein R2, R3 and R4 are as defined above.

In an aspect of the invention (ii-a) R2 and R4 are independently selected from the group consisting of H, $C_{1-6}$-alkyl, $C_{1-3}$-haloalkyl, especially $C_r$ haloalkyl, $C_{1-3}$-perhaloalkyl, especially $C_1$-perhaloalkyl, halogen, CN, $NO_2$, $NR'_2$, $CH_2N(R')_2$, OH, $(CH_2)_nOH$, COR'', and C(=N—OH)R'', wherein R' is in particular H or $C_{1-4}$-alkyl. In another aspect of the embodiment R2 and R4 are selected from the group consisting of H, branched $C_{3-6}$-alkyl, halogen, CN, $NO_2$, $NH_2$, $CH_2N(R')_2$, and OH, and R3 is in particular H, or OR3', wherein R3' is selected from the group consisting of H, $C_{1-4}$-alkyl, benzyl, acyl (Ac), mesyl (Ms), trifyl (Tf), glycyl, $PO(OR')_2$, COOR''' and $CONR'_2$. In a further aspect of this embodiment R3 is selected from the group consisting of H, OH, methoxy, OAc, OMs, and OTf; or (ii-b) R2 and R3 or R3 and R4, together with the ring carbon atoms to which they are attached, form an oxazolone or 1,3-oxazole ring, optionally substituted with methyl, and R4 or R2, respectively, is selected from the group consisting of H, F, Cl, Br, and I.

In an embodiment of the present invention, the invention relates to a compound of formula (I) or a pharmaceutically acceptable salt thereof, wherein R1, R5 and R6 are each H and R3 is OR3' and which compound has the formula (Ib)

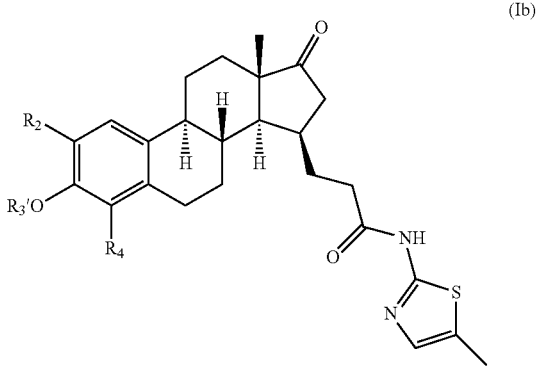

(Ib)

wherein R2, R3' and R4 are as defined above.

In an aspect of the embodiment R3' is selected from the group consisting of H, $C_{1-4}$-alkyl, mesyl and trifyl, in particular from H, methyl, mesyl and trifyl. In a further subgroup of this embodiment, the invention relates to a compound of formula (Ib) wherein R3' is H.

In another aspect of this embodiment one of R2 and R4 is independently selected from the group consisting of F, Cl, Br, I, $C_{1-6}$-alkyl, $NO_2$, $NH_2$, and CN and the other is selected from the group consisting of H, F, Cl, Br, I, $NO_2$, $NH_2$ and CN. In a further aspect of this embodiment both R2 and R4 are independently selected from the group consisting of F, Cl, Br, I, $NO_2$ and $NH_2$.

In an alternative embodiment of the present invention, the invention relates to a compound of formula (I) or a pharmaceutically acceptable salt thereof, wherein R2 and R3 or R3 and R4, together with the ring carbon atoms to which they are attached, form an unsaturated 5-membered heterocyclic ring; and which compound in particular has the formula (Ic), (Id), (Ie) or (If).

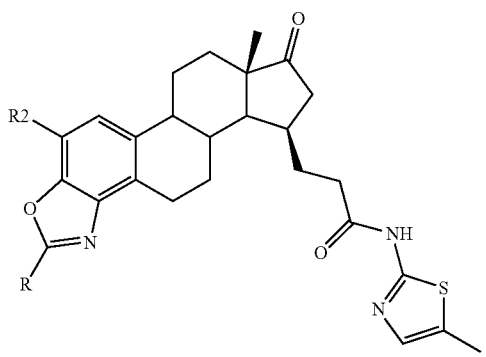
(Ic)

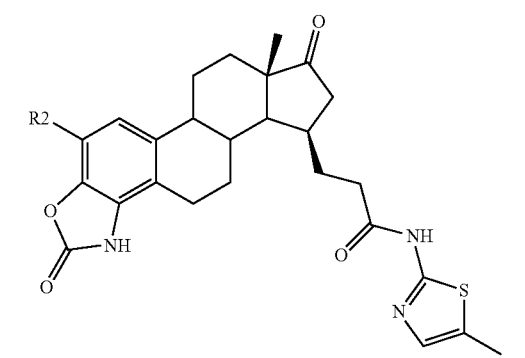
(Id)

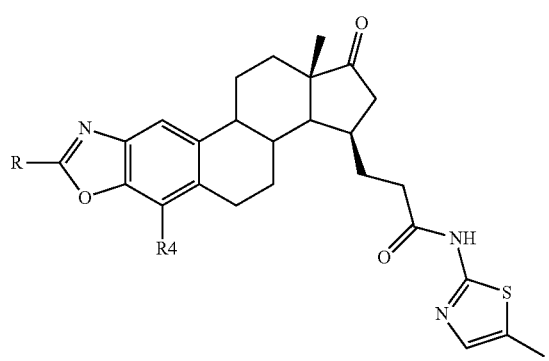
(Ie)

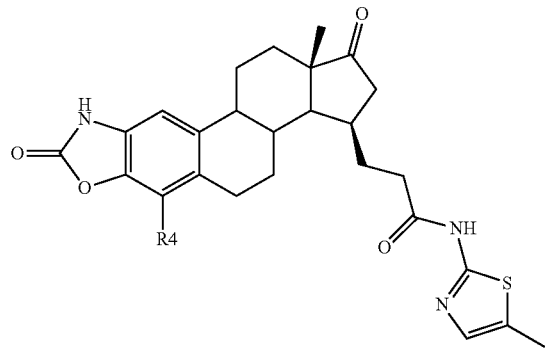
(If)

wherein R2 and R4 are selected from the group consisting of H, F, Cl, Br, and I, and R is H or methyl.

In an another alternative embodiment of the present invention, the invention relates to a compound of formula (I) wherein R1, R2 and R4 are H and R3 is OR3' and which compound has the formula (Ig)

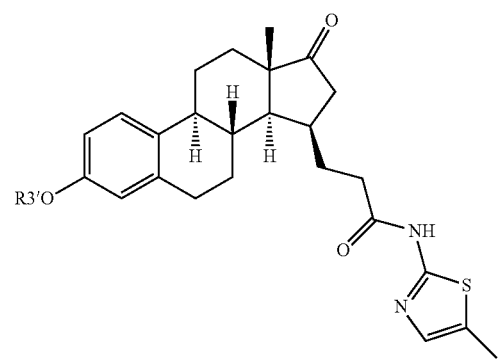
(Ig)

wherein R3' is as defined above.

In an aspect of this embodiment R3' is selected from the group consisting of benzyl, succinyl, optionally acylated glucuronyl, $(CH_2)_n OH$, $SO_2OH$, $SO_2R''$, tosyl, $SO_2N(R')_2$, $PO(OR')_2$, COOR''', $C(O)N(R')_2$, $C(O)(CH_2)_n N(R')_2$, $C(O)CH_2NHC(O)R'$, $C(O)CH_2NHC(O)OR''$ and $C(O)R'''$, wherein R' is H or $C_{1-8}$-alkyl, especially methyl or ethyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O, R'' is $C_{1-8}$-alkyl, $C_{1-3}$-haloalkyl, or $C_{1-3}$-perhaloalkyl, R''' is $C_{1-18}$-alkyl, $C_{2-18}$-alkenyl, $-(CH_2)_n-C_{3-8}$-cycloalkyl, or optionally substituted phenyl, and n is 1 or 2.

In an another further embodiment of the present invention, the invention relates to a compound of formula (I), wherein R3, R5 and R6 are each H and which compound has the formula (Ih)

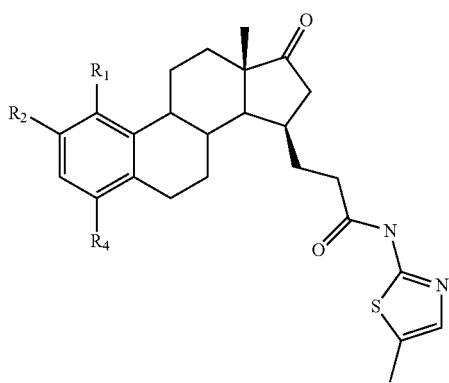

(Ih)

wherein R1, R2 and R4 are as defined above.

In an aspect of this embodiment one or more, in particular one or two of R1, R2 and R4 is independently selected from the group consisting of F, Cl, Br, I, OH, $NH_2$, and $NO_2$.

In an aspect of the present invention the invention relates to a compound of formula (I) selected from the group consisting of:

Compound 1 Acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 2 Methanesulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 3 2,2-Dimethyl-propionic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 4 Sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 5 Sulphuric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester; triethylamine salt Compound 6 Phosphoric acid diethyl ester; (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 7 Phosphoric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester;

Compound 8 Phosphoric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester; disodium salt Compound 9 Succinic acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester;

Compound 10 Succinic acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester; sodium salt Compound 11 Acetylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 12 Pentanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 13 3-Cyclopentyl-propionic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 14 Dodecanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 15 tert-Butoxycarbonylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 16 Amino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 17 Undec-10-enoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 18 Hexadecanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 19 2-Acetoxy-benzoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 20 Ethyl ((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl) carbonate;

Compound 21 Tert-butyl ((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl) carbonate;

Compound 22 (13S,15R)-13-Methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl octyl carbonate;

Compound 23 Dimethyl-sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 24 Morpholine-4-carboxylic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 25 Dimethyl-carbamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 26 Dimethylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 27 Toluene-4-sulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Compound 28 (2S,3S,4S,5R,6S)-2-(methoxycarbonyl)-6-(((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl)oxy)tetrahydro-2H-pyran-3,4,5-triyl triacetate;

Compound 29 (2S,3S,4S,5R,6S)-3,4,5-trihydroxy-6-(((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl)oxy)tetrahydro-2H-pyran-2-carboxylic acid;

Compound 30 3-((13S,15R)-3-Benzyloxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 31 3-((13S,15R)-2-(tert-butyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 32 3-((13S,15R)-3-hydroxy-2-isopropyl-13-methyl-17-oxo-7,8,9,11,12,13,14,15,16,17-decahydro-6H-cyclopenta[a]phenanthren-15-yl)-N-(5-methylthiazol-2-yl)propanamide;

Compound 33 3-((13S,15R)-2-acetyl-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 34 3-((13S,15R)-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide;

Compound 35 3-((13S,15R)-3-hydroxy-13-methyl-4-nitro-17-oxo-7,8,9,11,12,13,14,15,16,17-decahydro-6H-cyclopenta[a]phenanthren-15-yl)-N-(5-methylthiazol-2-yl)propanamide;

Compound 36 3-((13S,15R)-3-hydroxy-13-methyl-2,4-dinitro-17-oxo-7,8,9,11,12,13,14,15,16,17-decahydro-6H-cyclopenta[a]phenanthren-15-yl)-N-(5-methylthiazol-2-yl)propanamide;

Compound 37 3-((13S,15R)-2-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 38 3-((13S,15R)-4-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 39 (13S,15R)-13-methyl-15-(3-((5-methylthiazol-2-yl)amino)-3-oxopropyl)-4-nitro-17-oxo-7,8,9,11,12,13,14,15,16,17-decahydro-6H-cyclopenta[a]phenanthren-3-yl methanesulfonate;

Compound 40 (13S,15R)-4-amino-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl methanesulfonate Compound 41 3-((13S,15R)-3-hydroxy-13-methyl-17-oxo-4-(2,2,2-trifluoroacetamido)-7,8,9,11,12,13,14,15,16,17-decahydro-6H-cyclopenta[a]phenanthren-15-yl)-N-(5-methylthiazol-2-yl)propanamide;

Compound 42 3-((13S,15R)-3-hydroxy-13-methyl-2-(morpholinomethyl)-17-oxo-7,8,9,11,12,13,14,15,16,17-decahydro-6H-cyclopenta[a]phenanthren-15-yl)-N-(5-methylthiazol-2-yl)propanamide;

Compound 43 3-((13S,15R)-3-hydroxy-13-methyl-2-(morpholinomethyl)-4-nitro-17-oxo-7,8,9,11,12,13,14,15,16,17-decahydro-6H-cyclopenta[a]phenanthren-15-yl)-N-(5-methylthiazol-2-yl)propanamide;

Compound 44 3-((13S,15R)-2-((dimethylamino)methyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 45 3-((13S,15R)-3-hydroxy-13-methyl-17-oxo-2-(pyrrolidin-1-ylmethyl)-7,8,9,11,12,13,14,15,16,17-decahydro-6H-cyclopenta[a]phenanthren-15-yl)-N-(5-methylthiazol-2-yl)propanamide;

Compound 46 3-((7aS,10R)-7a-methyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide;

Compound 47 3-((3R,12aS)-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;

Compound 48 3-((3R,12aS)-8,12a-dimethyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;

Compound 49 3-((7aS,10R)-2,7a-dimethyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide;

Compound 50 3-((3R,12aS)-12a-methyl-1,8-dioxo-2,3,3a,3b,4,5,8,9,10b,11,12,12a-dodecahydro-1H-cyclopenta[7,8]phenanthro[3,2-d]oxazol-3-yl)-N-(5-methylthiazol-2-yl)propanamide;

Compound 51 3-((7aS,10R)-7a-methyl-2,8-dioxo-2,5b,6,7,7a,8,9,10,10a,10b,11,12-dodecahydro-1H-cyclopenta[7,8]phenanthro[1,2-d]oxazol-10-yl)-N-(5-methylthiazol-2-yl)propanamide;

Compound 52 3-((13S,15R)-2-iodo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 53 3-((13S,15R)-3-hydroxy-2,4-diiodo-13-methyl-17-oxo-7,8,9,11,12,13,14,15,16,17-decahydro-6H-cyclopenta[a]phenanthren-15-yl)-N-(5-methylthiazol-2-yl)propanamide;

Compound 54 3-((13S,15R)-3-hydroxy-4-iodo-13-methyl-17-oxo-7,8,9,11,12,13,14,15,16,17-decahydro-6H-cyclopenta[a]phenanthren-15-yl)-N-(5-methylthiazol-2-yl)propanamide;

Compound 55 3-((13S,15R)-3-hydroxy-2-iodo-13-methyl-17-oxo-7,8,9,11,12,13,14,15,16,17-decahydro-6H-cyclopenta[a]phenanthren-15-yl)-N-(5-methylthiazol-2-yl)propanamide;

Compound 56 3-((13S,15R)-2-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 57 3-((13S,15R)-4-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 58 3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 59 N-(5-methylthiazol-2-yl)-3-((13S,15S)-2,4,16-tribromo-3-hydroxy-13-methyl-17-oxo-7,8,9,11,12,13,14,15,16,17-decahydro-6H-cyclopenta[a]phenanthren-15-yl)propanamide;

Compound 60 N-(5-methylthiazol-2-yl)-3-((13S,15S)-2,4,16-tribromo-3-methoxy-13-methyl-17-oxo-7,8,9,11,12,13,14,15,16,17-decahydro-6H-cyclopenta[a]phenanthren-15-yl)propanamide;

Compound 61 3-((13S,15S)-2,16-dibromo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 62 3-((13S,15S)-16-bromo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 63 3-((13S,15R)-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 64 3-((13S,15R)-2-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 65 3-((13S,15R)-2,4-dichloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 66 3-((13S,15R)-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 67 3-((13S,15R)-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 68 3-((13S,15R)-2,3-dihydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compounds 69 (13S,15R)-2-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate;

Compound 70 (13S,15R)-4-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate;

Compound 71 3-((13S,15R)-2-bromo-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 72 3-((13S,15R)-4-bromo-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 73 3-((13S,15R)-4-fluoro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide;

Compound 74 3-((13S,15R)-2-amino-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 75 3-((13S,15R)-4-chloro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide;

Compound 76 3-((13S,15R)-2-amino-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 77 3-((3R,12aS)-6-chloro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;

Compound 78 3-((3R,12aS)-6-fluoro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;

Compound 79 (13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl trifluoromethanesulfonate;

Compound 80 (13S,15R)-13-methyl-15-(3-((5-methylthiazol-2-yl)amino)-3-oxopropyl)-2-nitro-17-oxo-7,8,9,11,12,13,14,15,16,17-decahydro-6H-cyclopenta[a]phenanthren-3-yl trifluoromethanesulfonate;

Compound 81 (13S,15R)-13-methyl-15-(3-((5-methylthiazol-2-yl)amino)-3-oxopropyl)-4-nitro-17-oxo-7,8,9,11,12,13,14,15,16,17-decahydro-6H-cyclopenta[a]phenanthren-3-yl trifluoromethanesulfonate;

Compound 82 (13S,15R)-2-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl trifluoromethanesulfonate;

Compound 83 3-((13S,15R)-13-methyl-17-oxo-7,8,9,11,12,13,14,15,16,17-decahydro-6H-cyclopenta[a]phenanthren-15-yl)-N-(5-methylthiazol-2-yl)propanamide;

Compound 84 3-((13S,15R)-13-methyl-2-nitro-17-oxo-7,8,9,11,12,13,14,15,16,17-decahydro-6H-cyclopenta[a]phenanthren-15-yl)-N-(5-methylthiazol-2-yl)propanamide;

Compound 85 3-((13S,15R)-13-methyl-4-nitro-17-oxo-7,8,9,11,12,13,14,15,16,17-decahydro-6H-cyclopenta[a]phenanthren-15-yl)-N-(5-methylthiazol-2-yl)propanamide;

Compound 86 3-((13S,15R)-2-fluoro-13-methyl-17-oxo-7,8,9,11,12,13,14,15,16,17-decahydro-6H-cyclopenta[a]phenanthren-15-yl)-N-(5-methylthiazol-2-yl)propanamide;

Compound 87 3-((13S,15R)-2-amino-13-methyl-17-oxo-7,8,9,11,12,13,14,15,16,17-decahydro-6H-cyclopenta[a]phenanthren-15-yl)-N-(5-methylthiazol-2-yl)propanamide;

Compound 88 3-((13S,15R)-2-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 89 3-((13S,15R)-4-amino-13-methyl-17-oxo-7,8,9,11,12,13,14,15,16,17-decahydro-6H-cyclopenta[a]phenanthren-15-yl)-N-(5-methylthiazol-2-yl)propanamide;

Compound 90 3-((13S,15R)-4-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 91 3-((13S,15R)-2-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 92 3-((13S,15R)-4-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 93 3-((13S,15S)-16-hydroxy-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 94 3-((13S,15R)-4-hydroxy-13-methyl-1-nitro-17-oxo-7,8,9,11,12,13,14,15,16,17-decahydro-6H-cyclopenta[a]phenanthren-15-yl)-N-(5-methylthiazol-2-yl)propanamide;

Compound 95 3-{(13S,15S)-3-Hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide;

Compound 96 3-{(13S,15S)-16-[1-Hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide;

Compound 97 3-{(13S,15S)-16-[1-Hydroxy-methylidene]-3-methoxy-13-methyl-17-oxo-7,8,9,11,12,13,14,15,16,17-decahydro-6H-cyclopenta[a]phenanthren-15-yl}-N-(5-methylthiazol-2-yl)propanamide;

Compound 98 3-{(13S,15S)-2-tert-Butyl-3-hydroxy-16-[1-hydroxy-methylidene]-13-methyl-17-oxo-7,8,9,11;12,13,14,15,16,17-decahydro-6H-cyclopenta[a]phenanthren-15-yl}-N-(5-methylthiazol-2-yl)propanamide;

Compound 99 3-{(13S,15S)-2-Bromo-3-hydroxy-16-[1-hydroxy-methylidene]-13-methyl-17-oxo-7,8,9,11;12,13,14,15,16,17-decahydro-6H-cyclopenta[a]phenanthren-15-yl}-N-(5-methylthiazol-2-yl)propanamide;

Compound 100 3-{(13S,15S)-4-Bromo-3-hydroxy-16-[1-hydroxy-methylidene]-13-methyl-17-oxo-7,8,9,11;12,13,14,15,16,17-decahydro-6H-cyclopenta[a]phenanthren-15-yl}-N-(5-methylthiazol-2-yl)propanamide;

Compound 101 3-{(13S,15S)-2,4-Dibromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide;

Compound 102 3-{(13S,15S)-16-[1-hydroxy-methylidene]-2-iodo-3-methoxy-13-methyl-17-oxo-7,8,9,11,12,13,14,15,16,17-decahydro-6H-cyclopenta[a]phenanthren-15-yl}-N-(5-methylthiazol-2-yl)propanamide;

Compound 103 3-{(13S,15S)-3-hydroxy-16-[1-hydroxy-methylidene]-13-methyl-2-nitro-17-oxo-7,8,9,11,12,13,14,15,16,17-decahydro-6H-cyclopenta[a]phenanthren-15-yl}-N-(5-methylthiazol-2-yl)propanamide;

Compound 104 3-{(13S,15S)-3-hydroxy-16-[1-hydroxy-methylidene]-13-methyl-4-nitro-17-oxo-7,8,9,11,12,13,14,15,16,17-decahydro-6H-cyclopenta[a]phenanthren-15-yl}-N-(5-methylthiazol-2-yl)propanamide;

or a pharmaceutically acceptable salt thereof.

A more preferred embodiment of the present invention relates to compounds of formula (I) selected from the group consisting of:

Compound 1 Acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester;

Phosphoric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester disodium salt;

Compound 30 3-((13S,15R)-3-Benzyloxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 47 3-((3R,12aS)-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;

Compound 55 3-((13S,15R)-3-hydroxy-2-iodo-13-methyl-17-oxo-7,8,9,11,12,13,14,15,16,17-decahydro-6H-cyclopenta[a]phenanthren-15-yl)-N-(5-methylthiazol-2-yl)propanamide;

Compound 56 3-((13S,15R)-2-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 57 3-((13S,15R)-4-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 58 3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 66 3-((13S,15R)-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 67 3-((13S,15R)-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

Compound 69 (13S,15R)-2-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate;

Compound 70 (13S,15R)-4-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate;

Compound 83 3-((13S,15R)-13-methyl-17-oxo-7,8,9,11,12,13,14,15,16,17-decahydro-6H-cyclopenta[a]phenanthren-15-yl)-N-(5-methylthiazol-2-yl)propanamide;

Compound 86 3-((13S,15R)-2-fluoro-13-methyl-17-oxo-7,8,9,11,12,13,14,15,16,17-decahydro-6H-cyclopenta[a]phenanthren-15-yl)-N-(5-methylthiazol-2-yl)propanamide;

Compound 88 3-((13S,15R)-2-hydroxy-13-methyl-17-oxo-7,8,9,11,12,13,14,15,16,17-decahydro-6H-cyclopenta[a]phenanthren-15-yl)-N-(5-methylthiazol-2-yl)propanamide; and Compound 90 3-((13S,15R)-4-hydroxy-13-methyl-17-oxo-7,8,9,11,12,13,14,15,16,17-decahydro-6H-cyclopenta[a]phenanthren-15-yl)-N-(5-methylthiazol-2-yl)propanamide;

or a pharmaceutically acceptable salt thereof.

EXAMPLES OF THE INVENTION

Representative examples of compounds of formula (I) are shown in Table 1.

TABLE 1
| # | Compound | NMR |
|---|---|---|
| 1 | 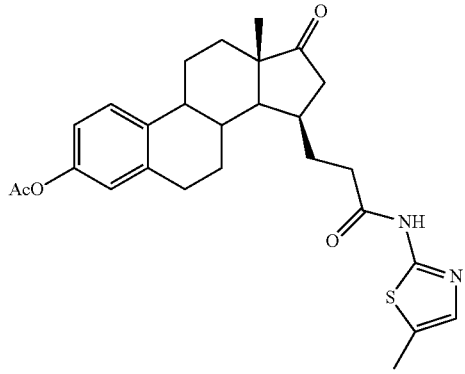 [SMILES: CC(=O)Oc1ccc2c(c1)CCC1C2CC[C@]2(C)C(=O)C[C@@H](CCC(=O)Nc3ncc(C)s3)C12] | ¹H-NMR (DMSO-d$_6$): 0.98 (s, 3H), 1.35-2.40 (m, 22H), 2.86 (m, 2H), 6.83-6.87 (m, 2H), 7.11 (s, 1H), 7.29 (d, 1H), 11.91 (s, 1H). |
| 2 | 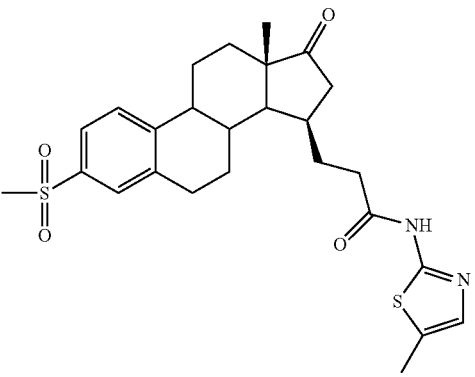 [SMILES: Cc1cnc(NC(=O)CC[C@@H]2CC(=O)[C@@]3(C)CCC4c5ccc(S(C)(=O)=O)cc5CCC4C23)s1] | ¹H-NMR (DMSO-d$_6$): 0.97 (s, 3H), 1.36-2.40 (m, 22H), 2.91 (m, 2H), 6.82-6.86 (m, 2H), 7.09 (s + d, 3H), 7.37 (d, 1H), 11.91 (s, 1H). |
| 3 | 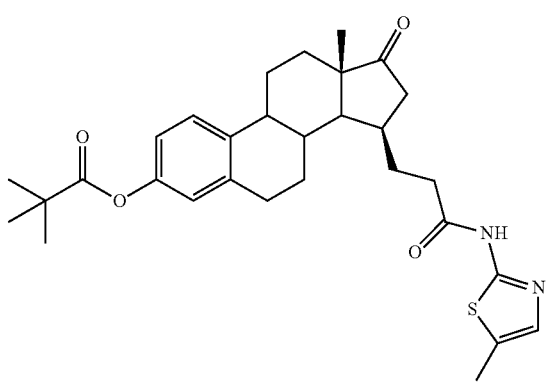 [SMILES: Cc1cnc(NC(=O)CC[C@@H]2CC(=O)[C@@]3(C)CCC4c5ccc(OC(=O)C(C)(C)C)cc5CCC4C23)s1] | ¹H-NMR (DMSO-d$_6$): 0.97 (s, 3H), 1.28 (s, 9H, 3 × Me), 1.35-2.40 (m, 19H), 2.86 (m, 2H), 6.79-6.83 (m, 2H), 7.11 (s, 1H), 7.28 (d, 1H), 11.92 (s, 1H). |
| 4 | 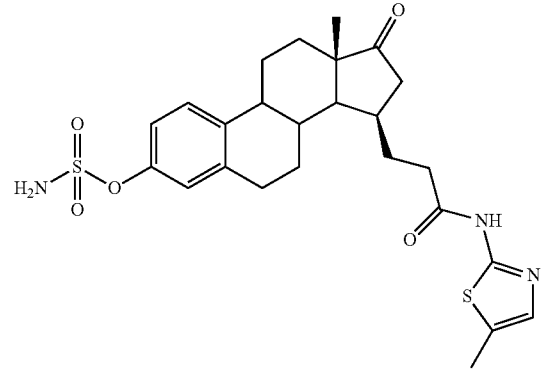 [SMILES: Cc1cnc(NC(=O)CC[C@@H]2CC(=O)[C@@]3(C)CCC4c5ccc(OS(N)(=O)=O)cc5CCC4C23)s1] | ¹H-NMR (DMSO-d$_6$): 0.97 (s, 3H), 1.30-2.40 (m, 19H), 2.86 (m, 2H), 7.00-7.37 (m, 4H), 7.92 (s, 2H), 11.92 (s, 1H). |

TABLE 1-continued
| # | Compound | NMR |
|---|---|---|
| 5 | 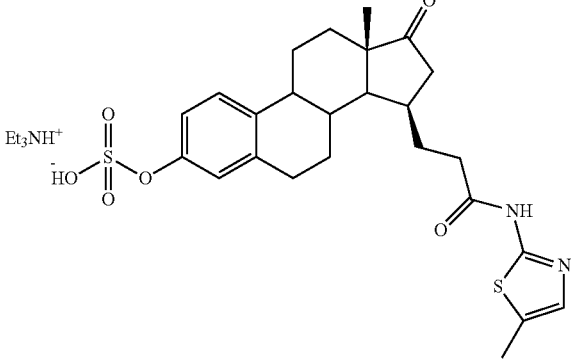 | ¹H-NMR (DMSO-d$_6$): 0.97 (s, 3H), 1.16 (t, 9H), 1.30-2.40 (m, 19H), 2.83 (m, 2H), 3.09 (q, 6H), 6.88-6.90 (m, 2H), 7.11-7.17 (m, 2H), 11.91 (s, 1H). |
| 6 | 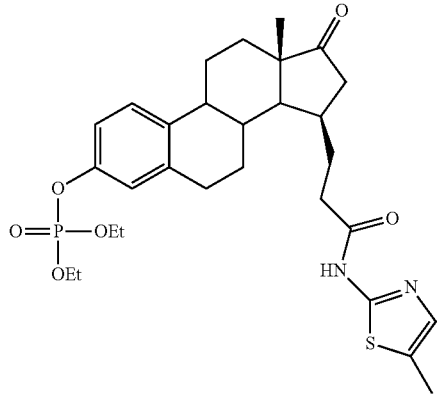 | ¹H-NMR (DMSO-d$_6$): 0.96 (t, 3H), 1.27 (2 × t, 6H), 1.30-2.40 (m, 19H), 2.86 (m, 2H), 4.07-4.22 (m, 4H), 6.91 (s, 1H), 6.95 (s, 1H), 7.10 (s, 1H), 7.28 (d, 1H). |
| 7 | 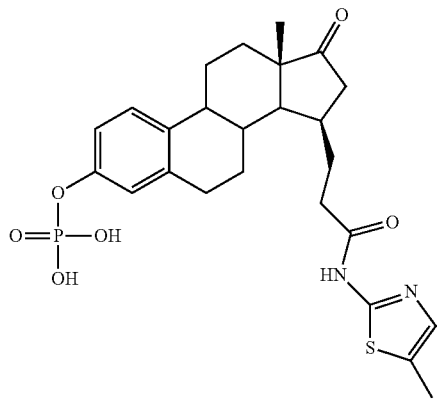 [SMILES: Cc1cnc(NC(=O)CC[C@@H]2CC(=O)[C@@]3(C)CCC4c5ccc(OP(=O)(O)O)cc5CCC4C23)s1] | ¹H-NMR (DMSO-d$_6$): 0.97 (s, 3H), 1.35-2.40 (m, 19H), 2.85 (m, 2H), 6.89 (s, 1H), 6.92 (s, 1H), 7.12 (s, 1H), 7.24 (d, 1H), 11.92 (s, 1H). |
| 8 | 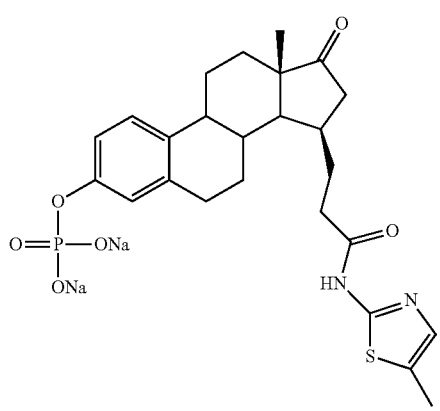 | ¹H-NMR (D$_2$O): 0.94 (s, 3H), 1.35-2.40 (m, 19H), 2.78 (m, 2H), 6.89 (s, 1H), 6.92 (s, 1H), 7.14-7.18 (m, 2H). |

TABLE 1-continued
| # | Compound | NMR |
|---|----------|-----|
| 9 | 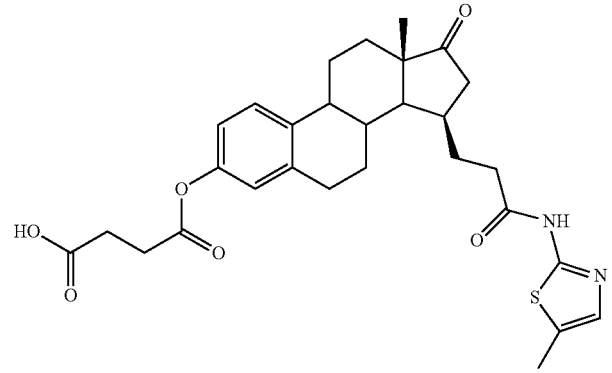 [SMILES: Cc1cnc(NC(=O)CC[C@@H]2CC(=O)[C@@]3(C)CCC4c5ccc(OC(=O)CCC(=O)O)cc5CCC4C23)s1] | ¹H-NMR (DMSO-$d_6$): 0.98 (s, 3H), 1.36-1.45 (m, 3H), 1.72 (m, 4H), 1.89-2.4 (m, 12H), 2.54-2.61 (m, 2H), 2.76-2.90 (m, 4H), 6.81 (s, 1H), 6.83 (d, 1H), 7.12 (s, 1H), 7.30 (d, 1H), 11.96 (s, 1H). |
| 10 | 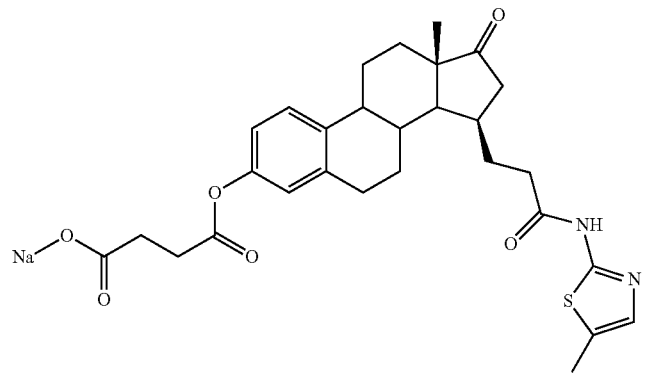 | ¹H-NMR (DMSO-$d_6$): 0.96 (s, 3H), 1.31-1.38, (m, 3H), 1.61-1.79 (m), 1.99-2.23 (m), 2.33 (s, 3H), 2.76-2.79 (m, 2H), 2.89 (s, 4H), 6.47 (s, 1H), 6.51 (d, 1H), 7.04 (d, 1H), 7.11 (s, 1H), 11.93 (s, 1H). |
| 11 | 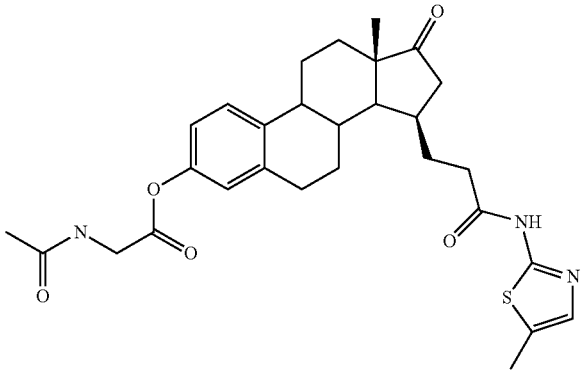 [SMILES: CC(=O)NCC(=O)Oc1ccc2c(c1)CCC1C2CC[C@]2(C)C(=O)C[C@@H](CCC(=O)Nc3ncc(C)s3)C12] | ¹H-NMR (DMSO-$d_6$): 0.98 (s, 3H), 1.37-1.73 (m, 6H), 1.90 (s, 3H), 2.27-2.89 (m, 9H), 3.98-4.07 (m, 2H), 6.83-6.87 (m, 2H), 7.11 (s, 1H), 7.31 (d, 1H), 8.46 (m, 1H), 11.92 (s, 1H). |
| 12 | 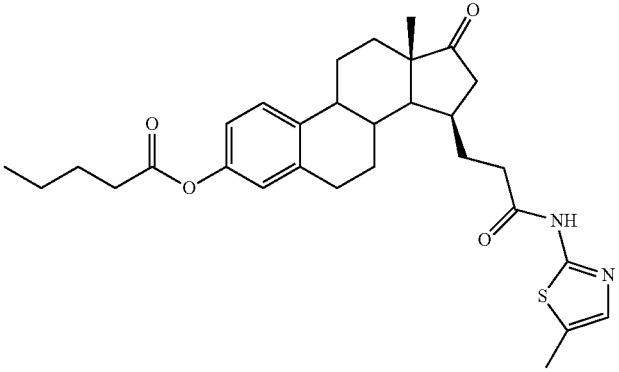 [SMILES: CCCCC(=O)Oc1ccc2c(c1)CCC1C2CC[C@]2(C)C(=O)C[C@@H](CCC(=O)Nc3ncc(C)s3)C12] | ¹H-NMR (DMSO-$d_6$): 0.92 (t, 3H), 0.99 (s, 3H), 1.24-2.59 (m, 25H), 2.87 (m, 2H), 6.82-6.86 (m, 2H), 7.11 (s, 1H), 7.30 (d, 1H), 11.92 (s, 1H). |

TABLE 1-continued

| # | Compound | NMR |
|---|---|---|
| 13 | (structure: 3-(3-cyclopentylpropanoyloxy) estra-1,3,5(10)-triene-17-one with 15-position propanamide-N-(5-methylthiazol-2-yl) substituent) | $^1$H-NMR (DMSO-d$_6$): 0.97 (s, 3H), 1.11 (m, 2H), 1.35-1.76 (m, 2H), 2.32 (s, 3H), 2.86 (m, 2H), 6.83 (m, 2H), 7.11 (s, 1H), 7.29 (d, 1H), 11.91 (s, 1H). |
| 14 | (structure: 3-dodecanoyloxy estra-1,3,5(10)-triene-17-one with 15-position propanamide-N-(5-methylthiazol-2-yl) substituent) | $^1$H-NMR (DMSO-d$_6$): 0.85 (t, 3H), 0.98 (s, 3H), 1.25-2.50 (m, 39H), 2.87 (m, 2H), 6.81-6.86 (m, 2H), 7.11 (s, 1H), 7.29 (d, 1H), 11.91 (s, 1H). |
| 15 | (structure: 3-(N-Boc-glycyloxy) estra-1,3,5(10)-triene-17-one with 15-position propanamide-N-(5-methylthiazol-2-yl) substituent) | $^1$H-NMR (DMSO-d$_6$): 0.98 (s, 3H), 1.40 (s, 9H), 1.7-2.5 (m), 2.32 (s, 3H), 2.87 (m, 2H), 3.93 (d, 2H, —CH2), 6.84 (m, 2H), 7.11 (s, 1H), 7.15-7.42 (m, 3H), 11.91 (s, 1H). |
| 16 | (structure: 3-(glycyloxy) estra-1,3,5(10)-triene-17-one with 15-position propanamide-N-(5-methylthiazol-2-yl) substituent) | $^1$H-NMR (DMSO-d$_6$): 0.98 (s, 3H), 1.41 (m), 1.7-2.5 (m), 2.33 (s, 3H), 2.90 (m, 2H), 4.11 (br s, 2H), 6.93 (m, 2H), 7.11 (s, 1H), 7.36 (2 × s, 2H), 8.37 (br s, 2H), 11.92 (s, 1H). |

TABLE 1-continued

| # | Compound | NMR |
|---|----------|-----|
| 17 | | $^1$H-NMR (DMSO-d$_6$): 0.98 (s, 3H), 1.29-2.56 (m, 35H), 2.86 (m, 2H), 4.91-5.05 (m, 2H), 5.69-5.89 (m, 1H), 6.81-6.85 (m, 2H), 7.11 (s, 1H), 7.29 (d, 1H), 11.92 (s, 1H). |
| 18 | | $^1$H-NMR (DMSO-d$_6$): 0.84 (t, 3H), 0.99 (s, 3H), 1.22-1.46 (m, 47H), 2.88 (m, 2H), 6.77-6.81 (m, 2H), 7.05 (s, 1H), 7.25 (d, 1H), 11.86 (s, 1H). |
| 19 | | $^1$H-NMR (DMSO-d$_6$): 0.98 (s, 3H), 1.42 (m), 1.6-2.4 (m), 2.23 (s, 3H), 2.32 (s, 3H), 2.90 (m, 2H), 6.95 (m, 2H), 7.10 (s, 1H), 7.33 (dd, 2H), 7.48 (dd, 1H), 7.77 (dd, 1H), 8.13 (d, 1H), 11.91 (s, 1H). |
| 20 | | $^1$H-NMR (DMSO-d$_6$): 0.98 (s, 3H), 1.28 (t, 3H), 1.35-2.40 (m, 19H), 1.48 (s, 9H), 2.88 (m, 2H), 4.22 (q, 2H), 6.93 (s, 1H), 6.95 (d, 1H), 7.11 (s, 1H), 7.31 (d, 1H), 11.92 (s, 1H). |

TABLE 1-continued

| # | Compound | NMR |
|---|---|---|
| 21 | | ¹H-NMR (DMSO-d₆): 0.98 (s, 3H), 1.25-2.40 (m, 19H), 1.48 (s, 9H), 2.87 (m, 2H), 6.89 (s, 1H), 6.91 (d, 1H) 7.11 (s, 1H), 7.29 (d 1H) 11.92 (s, 1H). |
| 22 | | ¹H-NMR (CDCl₃ + MeOH-d₄): 0.86 (t, 3H), 0.98 (t, 3H), 1.20-2.40 (m, 31H), 2.87 (m, 2H), 4.17 (t, 2H), 6.93 (s, 1H), 6.95 (d, 1H), 7.11 (s, 1H), 7.30 (d, 1H), 11.91 (s, 1H). |
| 23 | | ¹H-NMR (DMSO-d₆): 0.98 (s, 3H), 1.41 (m), 1.6-2.4 (m), 2.33 (s, 3H), 2.91 (s, 6H), 7.04 (s, 1H), 7.11 (m, 2H), 7.36 (d, 1H), 11.92 (s, 1H). |
| 24 | | ¹H-NMR (DMSO-d₆): 0.98 (t, 3H), 1.20-2.40 (m, 16H), 2.86 (m, 2H), 2.90 (s, 3H), 3.02 (s, 3H), 6.82 (s, 1H), 6.84 (d, 1H), 7.12 (s, 1H), 7.26 (dd, 1H), 11.92 (s, 1H). |

TABLE 1-continued

| # | Compound | NMR |
|---|---|---|
| 25 | (structure: 3-(dimethylcarbamoyloxy)-estra-1,3,5(10)-trien-17-one with 15-propanamide-N-(5-methylthiazol-2-yl) substituent) | ¹H-NMR (DMSO-d₆): 0.98 (t, 3H), 1.20-2.40 (m, 19H), 2.75 (m, 2H), 4.62 (s, 1H), 6.46 (s, 1H), 6.50 (d, 1H), 7.03 (d, 1H), 7.11 (s, 1H), 11.91 (br s, 1H), 12.21 (br s, 1H). |
| 26 | (structure: 3-(N,N-dimethylglycyloxy)-estra-1,3,5(10)-trien-17-one with 15-propanamide-N-(5-methylthiazol-2-yl) substituent) | ¹H-NMR (DMSO-d₆): 0.98 (s, 3H), 1.40 (m), 1.6-2.4 (m), 2.31 (s, 3H), 2.39 (s, 6H), 2.87 (s, 2H), 6.86 (s, 2H), 7.11 (m, 1H), 7.30 (d, 1H), 11.92 (s, 1H). |
| 27 | (structure: 3-(tosyloxy)-estra-1,3,5(10)-trien-17-one with 15-propanamide-N-(5-methylthiazol-2-yl) substituent) | ¹H-NMR (DMSO-d₆): 0.95 (s, 3H), 1.36 (m), 1.6-2.4 (m), 2.32 (s, 3H), 2.42 (s, 3H), 2.81 (s, 2H), 6.72 (m, 2H), 7.10 (m, 1H), 7.25 (d, 1H), 7.48 (d, 2H), 7.75 (d, 2H), 11.91 (s, 1H). |
| 28 | (structure: 3-(2,3,4-tri-O-acetyl-β-D-glucuronide methyl ester)-estra-1,3,5(10)-trien-17-one with 15-propanamide-N-(5-methylthiazol-2-yl) substituent) | ¹H-NMR (CDCl₃): 1.05 (s, 3H), 1.25-2.4 (m), 2.05 (s, 6H), 2.07 (s, 3H), 2.42 (s, 3H), 2.91 (m, 2H), 3.75 (s, 3H), 4.20 (d, 1H), 5.2-5.34 (m, 4H), 6.76 (m, 2H), 7.05 (s, 1H), 7.19 (d, 1H). |

TABLE 1-continued
| # | Compound | NMR |
|---|----------|-----|
| 29 | 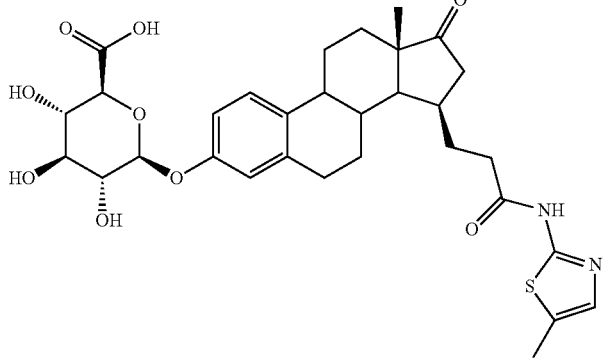 | ¹H-NMR (CDCl₃ + DMSO-d₆): 1.05 (s, 3H), 1.25-2.4 (m), 2.38 (s, 3H), 2.90 (m, 2H), 3.51-3.92 (m, 4H), 4.89 (d, 1H), 6.84 (m, 2H), 7.04 (s, 1H), 7.17 (d, 1H). |
| 30 | 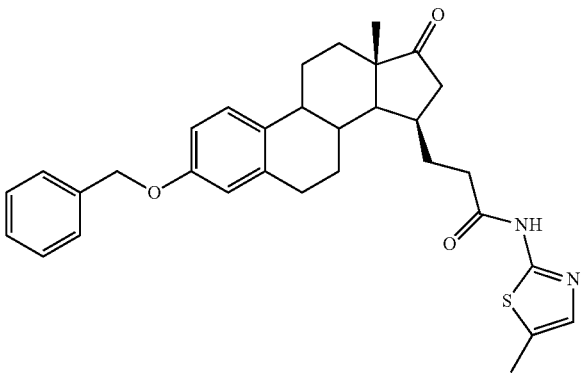 [SMILES: Cc1cnc(NC(=O)CC[C@@H]2CC(=O)[C@@]3(C)CCC4c5ccc(OCc6ccccc6)cc5CCC4C23)s1] | ¹H-NMR (DMSO-d₆): 0.97 (s, 3H), 1.37-2.50 (m, 19H), 2.85 (m, 2H), 5.06 (s, 2H), 6.74 (m, 2H), 7.11 (d, 1H), 7.16 (d, 1H), 11.92 (s, 1H). |
| 31 | 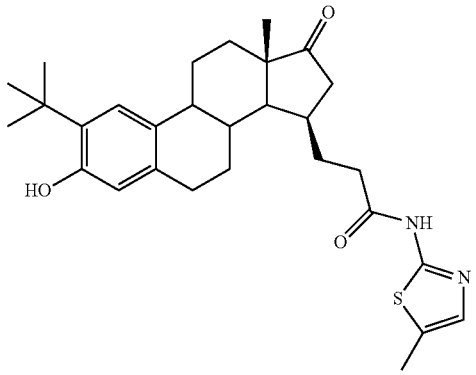 [SMILES: Cc1cnc(NC(=O)CC[C@@H]2CC(=O)[C@@]3(C)CCC4c5cc(C(C)(C)C)c(O)cc5CCC4C23)s1] | ¹H-NMR (DMSO-d₆): 0.97 (s, 3H), 1.2-1.45 (m, 12H), 1.5-2.4 (m, 16H), 2.6-2.95 (m, 2H), 6.47 (s, 1H), 7.01 (s, 1H), 7.11 (s, 1H), 8.97 (s, 1H), 11.92 (s, 1H, —NH). |
| 32 | 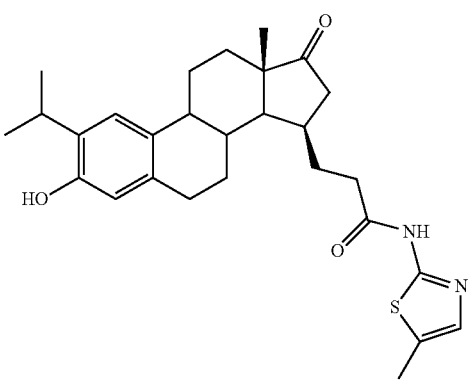 [SMILES: Cc1cnc(NC(=O)CC[C@@H]2CC(=O)[C@@]3(C)CCC4c5cc(C(C)C)c(O)cc5CCC4C23)s1] | ¹H-NMR (CDCl₃): 1.05 (s, 3H), 1.31 (s, 3H), 1.34 (s, 3H), 1.4-2.6 (m, 16H), 4.5 (m, 1H), 6.67 (m, 2H), 7.04 (s, 1H), 7.17 (d, 1H), 11.92 (s, 1H); |

TABLE 1-continued

| # | Compound | NMR |
|---|---|---|
| 33 | | $^1$H-NMR (CDCl$_3$): 1.05 (s, 3H), 1.36-2.68 (m, 22H), 2.90-3.03 (m, 2H), 3.89 (s, 3H), 6.69 (s, 1H), 7.05 (s, 1H), 7.69 (s, 1H), 11.76 (br, 1H); |
| 34 | | $^1$H-NMR (CDCl$_3$): 1.07 (s, 3H), 1.30-2.75 (m, 19H), 2.9-3.05 (m, 2H), 6.89 (s, 1H), 7.05 (s, 1H), 7.98 (s, 1H). |
| 35 | | $^1$H-NMR (CDCl$_3$): 1.08 (s, 3H), 1.3-3.4 (m, 21H), 6.96 (d, 1H), 7.05 (s, 1H), 7.45 (d, 1H). |
| 36 | | $^1$H-NMR (CDCl$_3$): 1.08 (s, 3H), 1.35-3.10 (m, 21H), 7.03 (s, 1H), 8.14 (s, 1H). |

TABLE 1-continued
| # | Compound | NMR |
|---|----------|-----|
| 37 | 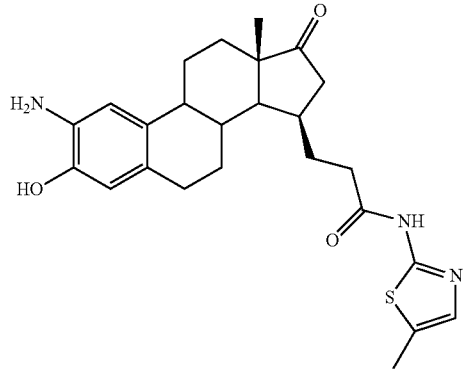 [SMILES: Cc1cnc(NC(=O)CC[C@@H]2CC(=O)[C@@]3(C)CCC4c5cc([N+](=O)[O-])c(O)cc5CCC4C23)s1] | ¹H-NMR (CDCl$_3$ + MeOH-d$_4$): 1.06 (s, 3H), 1.30-2.65 (m, 19H), 2.80-2.95 (m, 2H), 6.50 (s, 1H), 6.69 (s, 1H), 7.03 (s, 1H). |
| 38 | 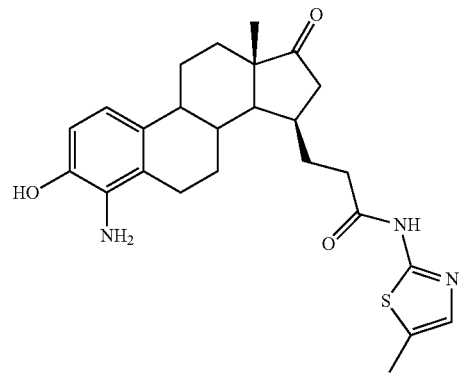 [SMILES: Cc1cnc(NC(=O)CC[C@@H]2CC(=O)[C@@]3(C)CCC4c5ccc(O)c(N)c5CCC4C23)s1] | ¹H-NMR (CDCl$_3$ + MeOH-d$_4$): 1.03 (s, 3H), 1.35-2.65 (m, 19H), 2.75-3.00 (m, 2H), 6.63 (s, 2H), 7.03 (s, 1H). |
| 39 | 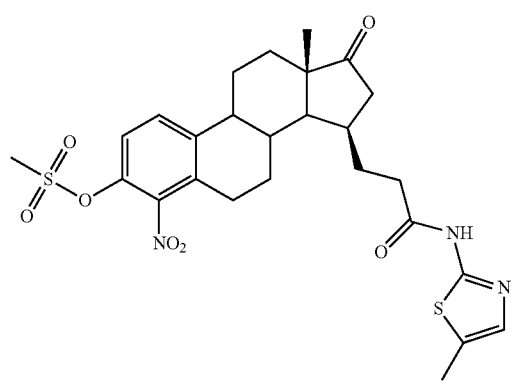 [SMILES: Cc1cnc(NC(=O)CC[C@@H]2CC(=O)[C@@]3(C)CCC4c5ccc(OS(C)(=O)=O)c([N+](=O)[O-])c5CCC4C23)s1] | ¹H-NMR (CDCl$_3$): 1.03 (s, 3H), 1.35-3.00 (m, 21H), 3.17 (s, 3H), 7.00 (s, 1H), 7.40 (AB, 2H), 11.25 (br s). |
| 40 | 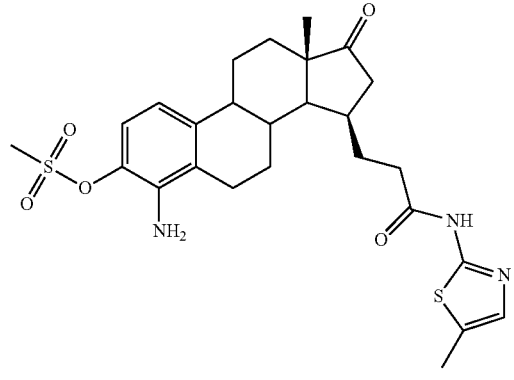 | ¹H-NMR (CDCl$_3$): 1.01 (s, 3H), 1.35-2.90 (m, 19H), 3.18 (s, 3H), 6.72 (d, 1H), 7.05 (d, 1H), 7.06 (s, 1H), 12.37 (br s, 1H). |

TABLE 1-continued
| # | Compound | NMR |
|---|---|---|
| 41 | 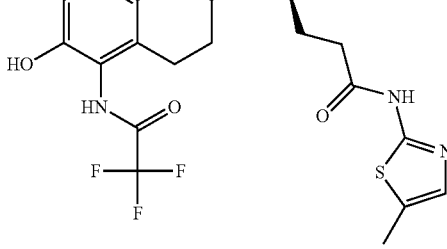 | ¹H-NMR (CDCl₃): 1.04 (s, 3H), 1.35-2.85 (m, 21H), 6.88 (d, 1H), 7.10 (s, 1H), 7.23 (d, 1H), 7.85 (s, 2H). |
| 42 | 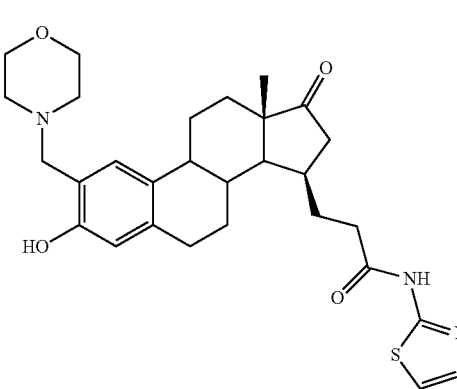 | ¹H-NMR (CDCl₃): 1.05 (s, 3H), 1.30-3.00 (m, 21H), 3.60-3.85 (m, 6H), 6.59 (s, 1H), 6.88 (s, 1H), 7.04 (s, 1H), 11.87 (br s, 1H). |
| 43 | 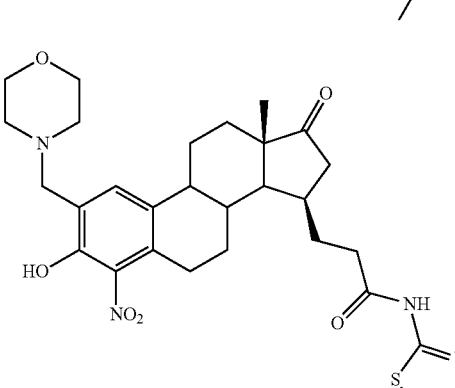 | ¹H-NMR (CDCl₃): 1.06 (s, 3H), 1.30-3.00 (m, 21H), 3.65-3.85 (m, 6H), 7.02 (s, 1H), 7.04 (s, 1H), 11.58 (br s, 1H). |
| 44 | 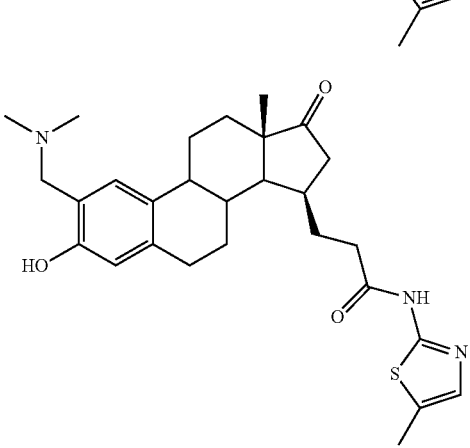 | ¹H-NMR (CDCl₃): 1.06 (s, 3H), 1.30-3.00 (m, 21H), 3.59 (AB, 2H), 6.58 (s, 1H), 6.85 (s, 1H), 7.05 (s, 1H), 11.50 (br s, 1H). |

TABLE 1-continued
| # | Compound | NMR |
|---|---|---|
| 45 | 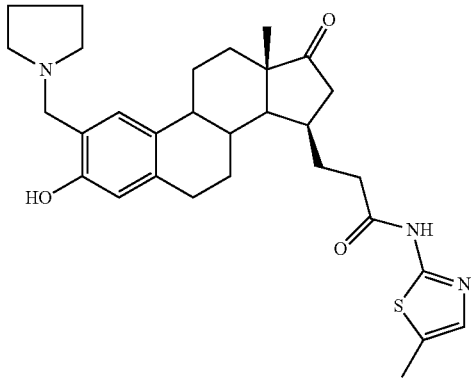 [SMILES: Cc1cnc(NC(=O)CC[C@@H]2CC(=O)[C@@]3(C)CCC4c5cc(CN6CCCC6)c(O)cc5CCC4C23)s1] | $^1$H-NMR (CDCl$_3$): 1.06 (s, 3H), 1.30-3.00 (m, 21H), 3.78 (AB, 2H), 6.57 (s, 1H), 6.88 (s, 1H), 7.05 (s, 1H), 12.00 (br s, 1H). |
| 46 | 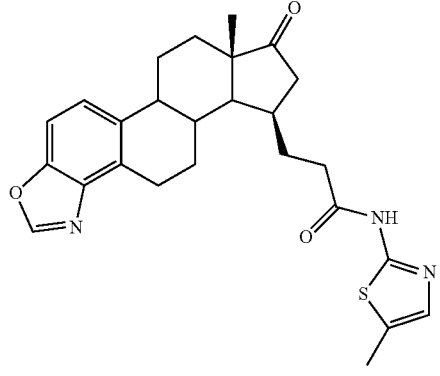 [SMILES: Cc1cnc(NC(=O)CC[C@@H]2CC(=O)[C@@]3(C)CCC4c5ccc6ocnc6c5CCC4C23)s1] | $^1$H-NMR (CDCl$_3$): 1.09 (s, 3H), 1.40-2.80 (m, 19H), 3.05-3.50 (m, 2H), 7.06 (s, 1H), 7.37 (s, 2H), 8.06 (s, 1H), 12.43 (s, 1H). |
| 47 | 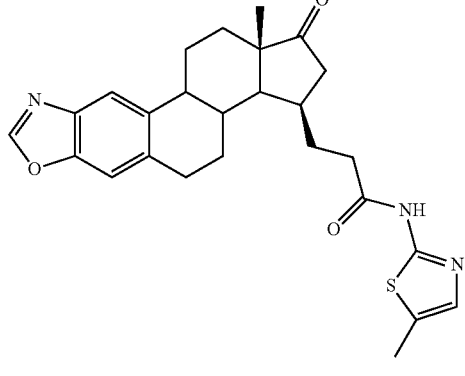 | $^1$H-NMR (CDCl$_3$): 1.07 (s, 3H), 1.30-2.75 (m, 18H), 2.95-3.15 (m, 3H), 7.05 (s, 1H), 7.32 (s, 1H), 7.70 (s, 1H), 8.01 (s, 1H), 12.31 (s, 1H). |
| 48 | 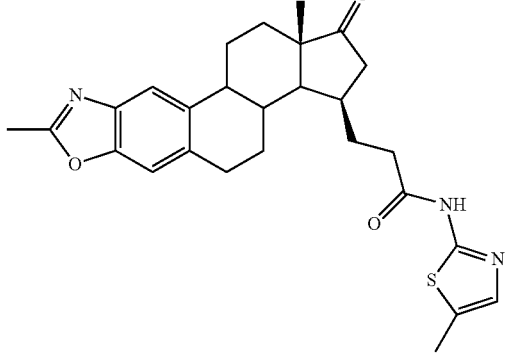 | $^1$H-NMR (CDCl$_3$): 1.07 (s, 3H), 1.35-2.75 (m, 22H), 2.90-3.10 (m, 2H), 7.05 (s, 1H), 7.19 (s, 1H), 7.55 (s, 1H), 12.22 (s, 1H). |

TABLE 1-continued

| # | Compound | NMR |
|---|---|---|
| 49 | | ¹H-NMR (DMSO-d₆): 0.99 (s, 3H), 1.23-3.16 (m, 24H), 7.12-7.41 (m, 2H), 11.93 (s, 1H). |
| 50 | | ¹H-NMR (CDCl₃): 1.06 (s, 3H), 1.35-2.75 (m, 19H), 2.80-3.00 (m, 2H), 6.91 (s, 1H), 6.98 (s, 1H), 7.10 (s, 1H), 10.67 (br s, 1H), 11.93 (br s, 1H). |
| 51 | | ¹H-NMR (DMSO-d₆): 0.97 (s, 3H), 1.25-2.95 (m, 21H), 7.00-7.20 (m, 3H), 11.68 (br s, 1H), 11.93 (s, 1H). |
| 52 | | ¹H-NMR (CDCl₃): 1.06 (s, 3H, —Me), 1.20-3.00 (m, 21H), 3.85 (s, 3H), 6.56 (s, 1H), 7.11 (s, 1H), 7.64 (s, 1H). |

TABLE 1-continued
| # | Compound | NMR |
|---|----------|-----|
| 53 | 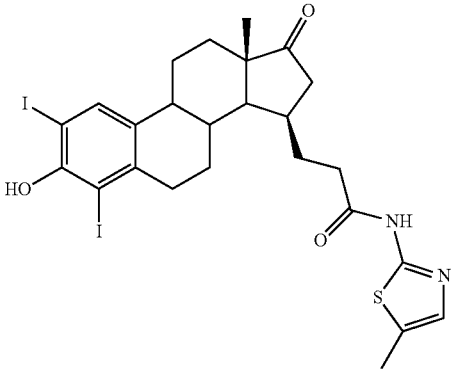 [SMILES: Cc1cnc(NC(=O)CC[C@@H]2CC(=O)[C@@]3(C)CCC4c5cc(I)c(O)c(I)c5CCC4C23)s1] | MS m/z (TOF ES+): 691 (M + 1), 713 (M + Na). |
| 54 | 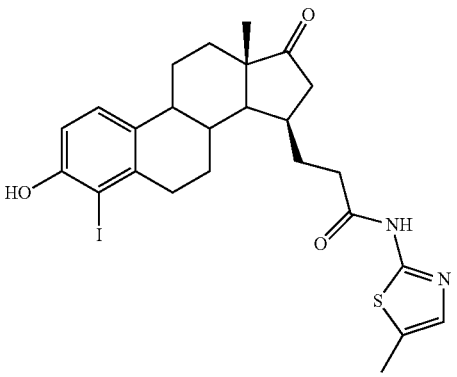 [SMILES: Cc1cnc(NC(=O)CC[C@@H]2CC(=O)[C@@]3(C)CCC4c5ccc(O)c(I)c5CCC4C23)s1] | $^1$H-NMR (CDCl$_3$): 1.04 (s, 3H), 1.30-2.95 (m, 21H), 6.84 (d, 1H), 7.06 (s, 1H), 7.19 (d, 1H). |
| 55 | 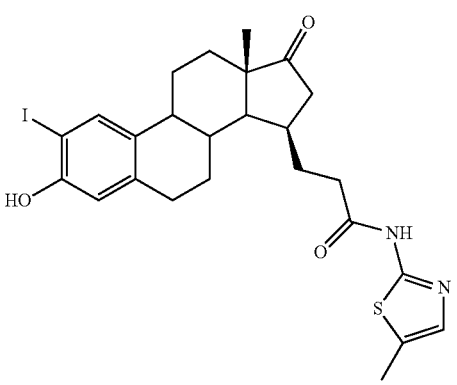 [SMILES: Cc1cnc(NC(=O)CC[C@@H]2CC(=O)[C@@]3(C)CCC4c5cc(I)c(O)cc5CCC4C23)s1] | $^1$H-NMR (CDCl$_3$): 1.05 (s, 3H), 1.28-2.75 (m, 19H), 2.75-2.90 (m, 2H), 6.74 (s, 1H), 7.05 (s, 1H), 7.51 (s, 1H). |
| 56 | 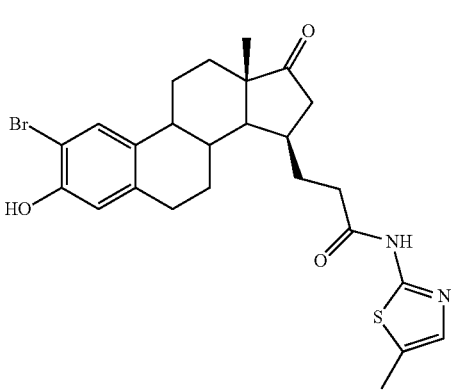 [SMILES: Cc1cnc(NC(=O)CC[C@@H]2CC(=O)[C@@]3(C)CCC4c5cc(Br)c(O)cc5CCC4C23)s1] | $^1$H-NMR (DMSO-d$_6$): 0.96 (s, 3H, —Me), 1.35-2.40 (m, 21H), 2.75 (m, 2H), 6.67 (s, 1H), 7.11 (s, 1H), 7.27 (s, 1H), 9.89 (s, 1H), 11.92 (s, 1H). |

TABLE 1-continued
| # | Compound | NMR |
|---|----------|-----|
| 57 | 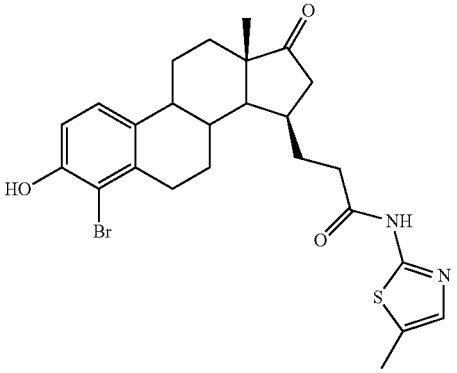 [SMILES: Cc1cnc(NC(=O)CC[C@@H]2CC(=O)[C@@]3(C)CCC4c5ccc(O)c(Br)c5CCC4C23)s1] | ¹H-NMR (DMSO-d$_6$): 0.95 (s, 3H, —Me), 1.35-2.40 (m, 21H), 2.83 (m, 2H), 6.78 (d, 1H), 7.11 (m, 2H), 7.27 (s, 1H), 9.89 (s, 1H), 11.92 (s, 1H). |
| 58 | 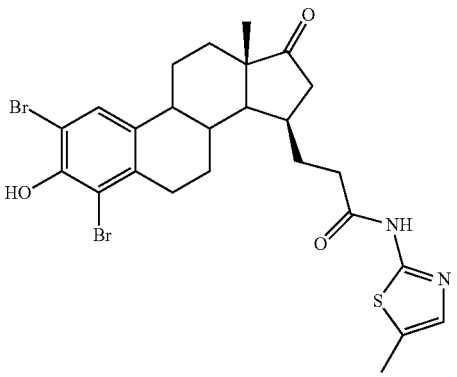 | ¹H-NMR (DMSO-d$_6$): 0.95 (s, 3H), 1.22-2.32 (m, 19H), 2.79 (m, 2H), 7.12 (s, 1H), 7.40 (s, 1H), 9.55 (s, 1H), 11.92 (s, 1H). |
| 59 | 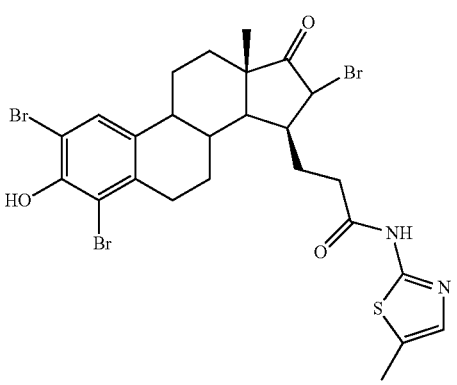 [SMILES: Cc1cnc(NC(=O)CC[C@@H]2C(Br)C(=O)[C@@]3(C)CCC4c5cc(Br)c(O)c(Br)c5CCC4C23)s1] | ¹H-NMR (CDCl$_3$): 1.10 (s, 3H), 1.35-3.10 (m, 21H), 4.55 (d, 1H), 7.15 (s, 1H), 7.38 (s, 1H). |
| 60 | 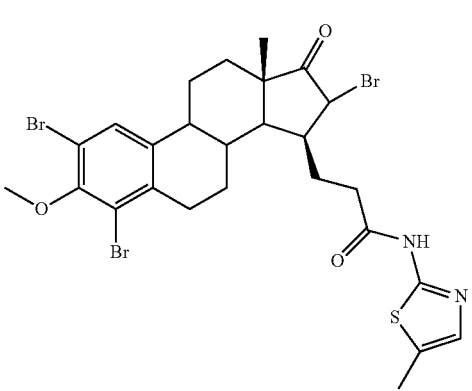 [SMILES: COc1c(Br)cc2c(c1Br)CCC1C2CC[C@]2(C)C(=O)C(Br)[C@@H](CCC(=O)Nc3ncc(C)s3)C12] | ¹H-NMR (CDCl$_3$): 1.14 (s, 3H), 1.25-2.99 (m, 19H), 3.87 (s, 3H), 5.03 (s, 1H), 6.64 (s, 1H), 7.41 (s, 1H). |

TABLE 1-continued

| # | Compound | NMR |
|---|---|---|
| 61 | (structure) | $^1$H-NMR (CDCl$_3$): 1.12 (s, 3H), 1.3-2.99 (m, 19H), 3.87 (s, 3H), 4.48 (d, 1H), 5.03 (s, 1H), 6.64 (s, 1H), 7.20 (m, 1H), 7.42 (s, 1H). |
| 62 | (structure) | $^1$H-NMR (DMSO-d$_6$): 1.05 (s, 3H), 1.25-2.90 (m, 19H), 3.69 (s, 3H), 5.03 (s, 1H), 6.68 (m, 2H), 7.12 (s, 1H), 11.95 (s, 1H). |
| 63 | (structure) | $^1$H-NMR (CDCl$_3$): 1.05 (s, 3H), 1.30-3.10 (m, 21H), 6.86 (d, 1H), 7.05 (s, 1H), 7.13 (d, 1H). |
| 64 | (structure) | $^1$H-NMR (CDCl$_3$ + MeOH-d$_4$): 1.06 (s, 3H), 1.20-2.65 (m, 19H), 2.75-3.05 (m, 2H), 6.70 (s, 1H), 7.03 (s, 1H), 7.18 (s, 1H). |

TABLE 1-continued
| # | Compound | NMR |
|---|---|---|
| 65 | 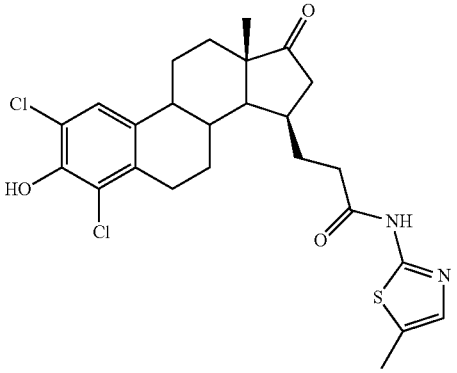 [SMILES: Cc1cnc(NC(=O)CC[C@@H]2CC(=O)[C@@]3(C)CCC4c5cc(Cl)c(O)c(Cl)c5CCC4C23)s1] | ¹H-NMR (DMSO-d₆): 0.96 (s, 3H), 1.35-2.40 (m, 21H), 2.80 (m, 2H), 7.12 (s, 1H), 7.23 (s, 1H), 9.75 (s, 1H), 11.92 (s, 1H). |
| 66 | 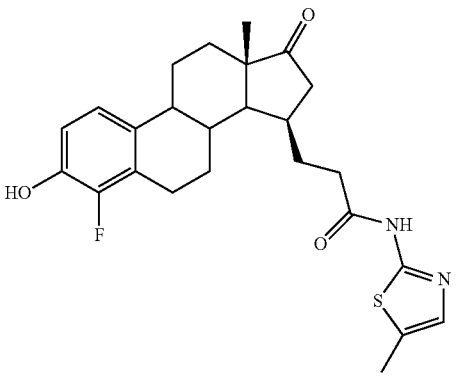 | ¹H-NMR (CDCl₃): 1.04 (s, 3H), 1.30-3.05 (m, 21H), 6.75-6.98 (m, 2H), 7.05 (br s, 1H). |
| 67 | 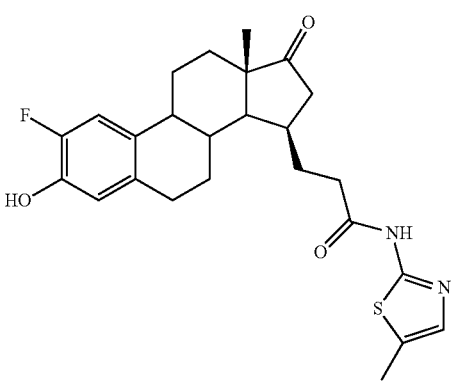 [SMILES: Cc1cnc(NC(=O)CC[C@@H]2CC(=O)[C@@]3(C)CCC4c5cc(F)c(O)cc5CCC4C23)s1] | ¹H-NMR (CDCl₃): 1.05 (s, 3H), 1.30-2.70 (m, 19H), 2.75-2.90 (m, 2H), 6.73 (d, J = 10 Hz, 1H), 6.97 (d, J = 14 Hz, 1H), 7.05 (br s, 1H). |
| 68 | 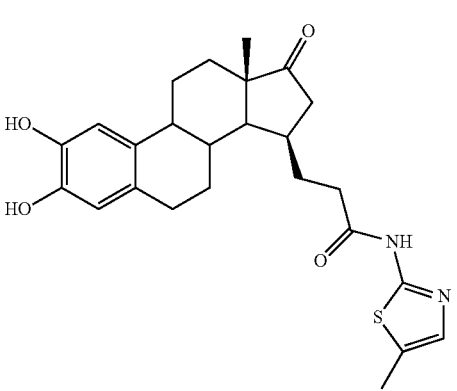 [SMILES: Cc1cnc(NC(=O)CC[C@@H]2CC(=O)[C@@]3(C)CCC4c5cc(O)c(O)cc5CCC4C23)s1] | ¹H-NMR (CDCl₃ + MeOH-d₄): 1.07 (s, 3H), 1.20-2.70 (m, 21H), 7.07 (s, 1H), 7.16 (s, 1H), 7.31 (s, 1H). |

TABLE 1-continued
| # | Compound | NMR |
|---|----------|-----|
| 69 | 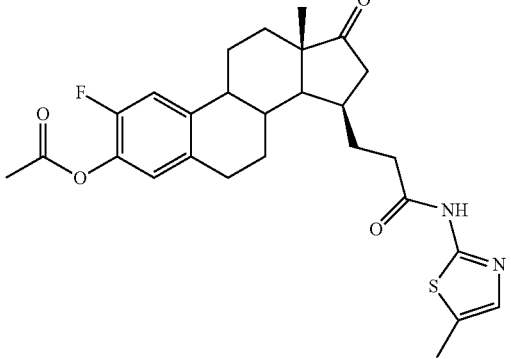 | $^1$H-NMR (CDCl$_3$): 1.06 (s, 3H), 1.16-2.75 (m, 25H), 2.76-3.0 (m, 2H), 6.83-7.1 (m, 3H); |
| 70 | 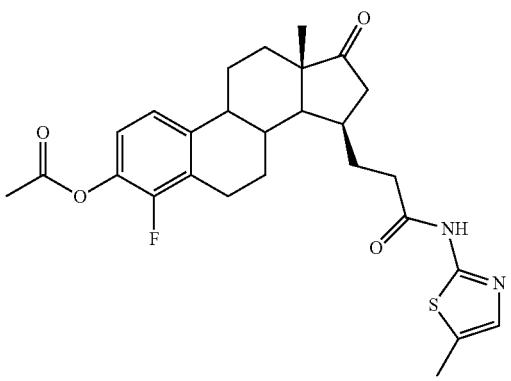 [SMILES: CC(=O)Oc1ccc2c(c1F)CCC1C2CC[C@]2(C)C(=O)C[C@@H](CCC(=O)Nc3ncc(C)s3)C12] | $^1$H-NMR (CDCl$_3$): 1.06 (s, 3H), 1.16-2.75 (m, 25H), 2.76-3.0 (m, 2H), 6.83-7.1 (m, 3H); |
| 71 | 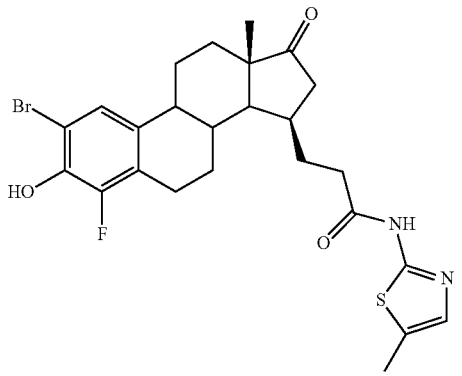 [SMILES: Cc1cnc(NC(=O)CC[C@@H]2CC(=O)[C@@]3(C)CCC4c5cc(Br)c(O)c(F)c5CCC4C23)s1] | $^1$H-NMR (CDCl$_3$): 1.05 (s, 3H), 1.26-2.99 (m, 21H), 7.05 (s, 1H), 7.12 (s, 1H). |
| 72 | 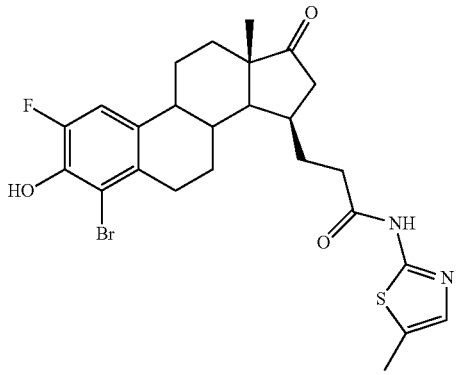 [SMILES: Cc1cnc(NC(=O)CC[C@@H]2CC(=O)[C@@]3(C)CCC4c5cc(F)c(O)c(Br)c5CCC4C23)s1] | $^1$H-NMR (CDCl$_3$): 1.04 (s, 3H), 1.36-2.97 (m, 21H), 6.99 (d, 1H), 7.05 (br s, 1H). |

TABLE 1-continued

| # | Compound | NMR |
|---|---|---|
| 73 | | ¹H-NMR (CDCl₃): 1.07 (s, 3H), 1.30-3.20 (m, 21H), 7.05 (s, 1H), 7.82 (s, 1H). |
| 74 | | ¹H-NMR (CDCl₃): 1.06 (s, 3H), 1.30-2.50 (m, 21H), 6.48 (s, 1H), 6.58 (s, 1H). |
| 75 | | ¹H-NMR (CDCl₃): 1.07 (s, 3H), 1.35-3.20 (m, 21H), 7.05 (s, 1H), 7.99 (s, 1H). |
| 76 | | ¹H-NMR (CDCl₃ + MeOH-d₄): 1.05 (s, 3H), 1.35-3.00 (m, 21H), 6.64 (s, 1H), 7.04 (s, 1H). |

TABLE 1-continued

| # | Compound | NMR |
|---|---|---|
| 77 | | $^1$H-NMR (CDCl$_3$): 1.07 (s, 3H), 1.40-3.45 (m, 21H), 7.06 (s, 1H), 7.66 (s, 1H), 8.06 (s, 1H), 11.89 (br s, 1H). |
| 78 | | $^1$H-NMR (CDCl$_3$): 1.08 (s, 3H), 1.40-3.20 (m, 21H), 7.05 (s, 1H), 7.52 (s, 1H), 8.03 (s, 1H), 11.91 (br s, 1H). |
| 79 | | $^1$H-NMR (DMSO-d$_6$): 0.98 (s, 3H), 1.25-2.50 (m, 19H), 2.85-3.00 (m, 2H), 7.11 (s, 1H), 7.22 (d + s, 2H), 7.46 (d, 1H), 11.91 (s, 1H). |
| 80 | | |

TABLE 1-continued
| # | Compound | NMR |
|---|----------|-----|
| 81 | 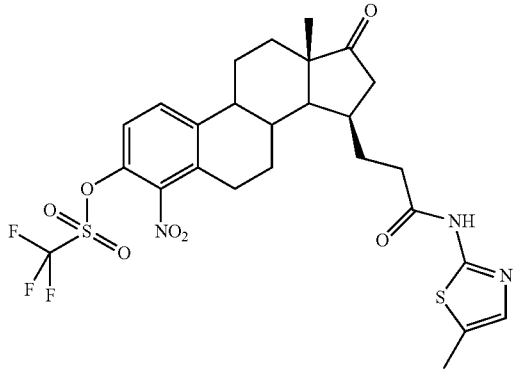 [SMILES: Cc1cnc(NC(=O)CC[C@@H]2CC(=O)[C@@]3(C)CCC4c5ccc(OS(=O)(=O)C(F)(F)F)c([N+](=O)[O-])c5CCC4C23)s1] | |
| 82 | 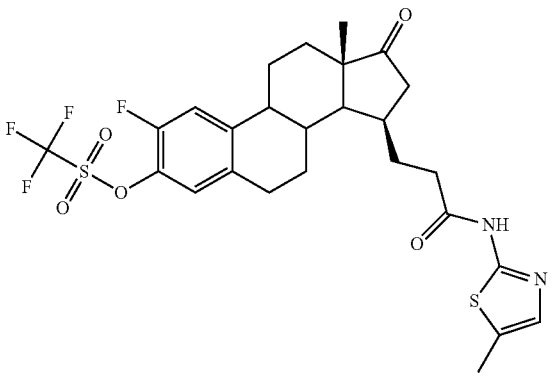 [SMILES: Cc1cnc(NC(=O)CC[C@@H]2CC(=O)[C@@]3(C)CCC4c5cc(F)c(OS(=O)(=O)C(F)(F)F)cc5CCC4C23)s1] | |
| 83 | 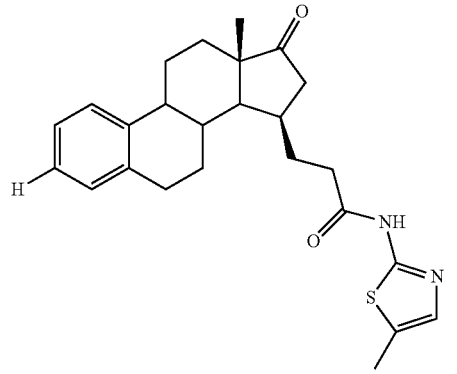 [SMILES: Cc1cnc(NC(=O)CC[C@@H]2CC(=O)[C@@]3(C)CCC4c5ccccc5CCC4C23)s1] | $^1$H-NMR (DMSO-d$_6$): 0.98 (s, 3H), 1.25-2.45 (m, 19H), 2.80-2.95 (m, 2H), 7.05-7.15 (m, 4H), 7.20-7.35 (m, 1H), 11.93 (s, 1H). |
| 84 | 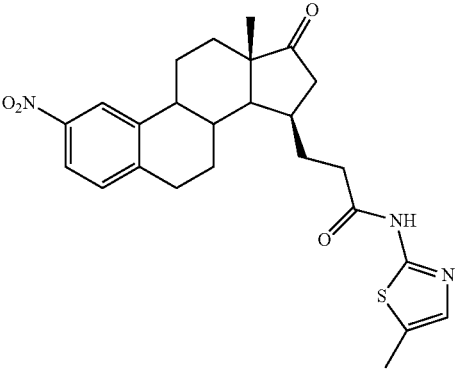 [SMILES: Cc1cnc(NC(=O)CC[C@@H]2CC(=O)[C@@]3(C)CCC4c5cc([N+](=O)[O-])ccc5CCC4C23)s1] | $^1$H-NMR (CDCl$_3$): 1.08 (s, 3H), 1.35-2.70 (m, 19H), 2.95-3.10 (m, 2H), 7.05 (s, 1H), 7.25 (d, 1H), 8.00 (d, 1H), 8.16 (s, 1H), 11.31 (br s, 1H). |

TABLE 1-continued
| # | Compound | NMR |
|---|---|---|
| 85 | 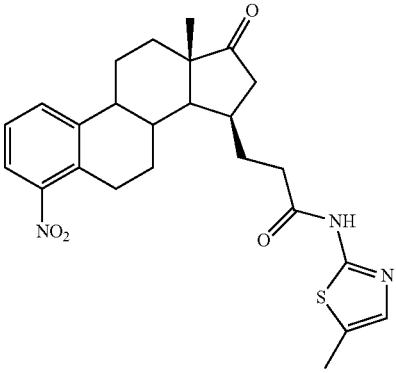 | ¹H-NMR (CDCl₃): 1.08 (s, 3H), 1.35-3.35 (m, 21H), 7.05 (s, 1H), 7.31 (t, 1H), 7.52 (d, 1H), 7.66 (d, 1H), 12.20 (br s, 1H). |
| 86 | 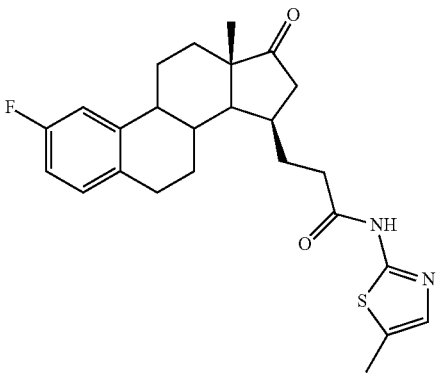 [SMILES: Cc1cnc(NC(=O)CC[C@@H]2CC(=O)[C@@]3(C)CCC4c5cc(F)ccc5CCC4C23)s1] | ¹H-NMR (CDCl₃): 1.06 (s, 3H), 1.30-3.0 (m, 21H), 6.50-7.10 (m, 4H), 6.94 (d, J = 12 Hz, 1H), 7.03 (br s, 1H). |
| 87 | 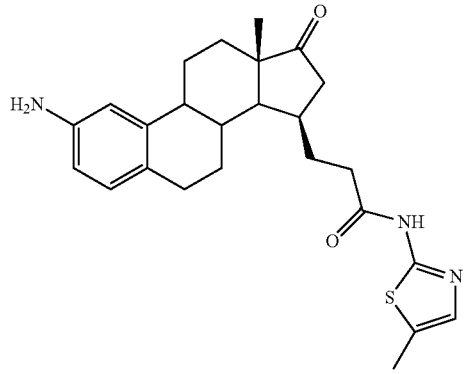 | ¹H-NMR (CDCl₃): 1.05 (s, 3H), 1.30-2.90 (m, 19H), 2.70-2.90 (m, 2H), 6.53 (d, 1H), 6.64 (s, 1H), 6.90 (d, 1H), 7.04 (s, 1H) 12.12 (br s, 1H). |
| 88 | 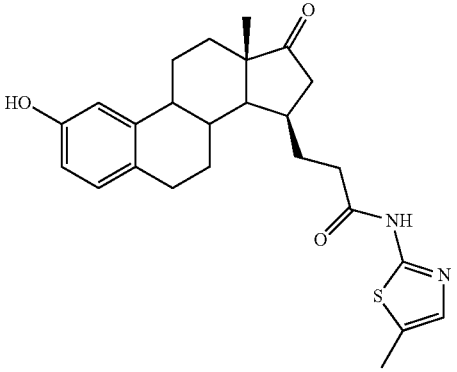 [SMILES: Cc1cnc(NC(=O)CC[C@@H]2CC(=O)[C@@]3(C)CCC4c5cc(O)ccc5CCC4C23)s1] | ¹H-NMR (CDCl₃): 0.97 (s, 3H), 1.30-2.85 (m, 21H), 6.65 (d, 1H), 6.77 (s, 1H), 6.91 (d, 1H), 7.05 (s, 1H). |

TABLE 1-continued
| # | Compound | NMR |
|---|---|---|
| 89 | 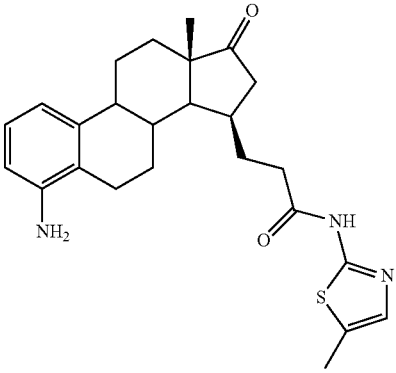 | $^1$H-NMR (CDCl$_3$ + MeOH-d$_4$): 1.05 (s, 3H), 1.35-2.70 (m, 21H), 6.60 (d, 1H), 6.79 (d, 1H), 7.03 (t, 1H), 7.03 (s, 1H). |
| 90 | 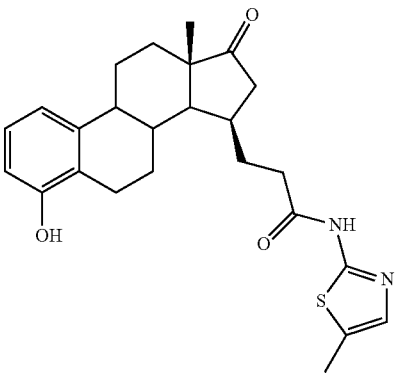 [SMILES: Cc1cnc(NC(=O)CC[C@@H]2CC(=O)[C@@]3(C)CCC4c5cccc(O)c5CCC4C23)s1] | $^1$H-NMR (CDCl$_3$ + MeOH-d$_4$): 1.05 (s, 3H), 1.30-2.05 (m, 21H), 6.67 (d, 1H), 6.85 (d, 1H), 7.00 (t, 1H), 7.03 (s, 1H). |
| 91 | 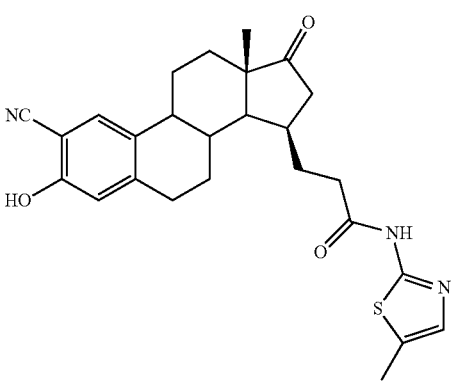 [SMILES: Cc1cnc(NC(=O)CC[C@@H]2CC(=O)[C@@]3(C)CCC4c5cc(C#N)c(O)cc5CCC4C23)s1] | $^1$H-NMR (CDCl3 + MeOH-d$_4$): 1.05 (s, 3H), 1.40-2.65 (m, 19H), 2.89 (m, 2H), 6.70 (s, 1H), 7.06 (s, 1H), 7.36 (s, 1H). |
| 92 | 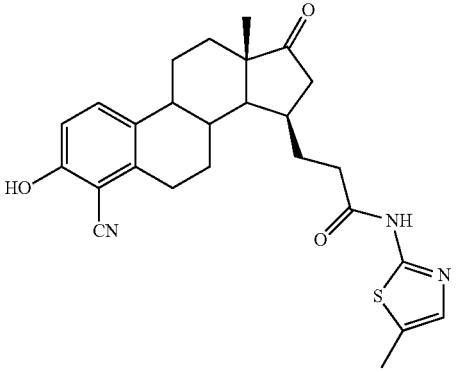 [SMILES: Cc1cnc(NC(=O)CC[C@@H]2CC(=O)[C@@]3(C)CCC4c5ccc(O)c(C#N)c5CCC4C23)s1] | $^1$H-NMR (CDCl3 + MeOH-d$_4$): 1.03 (s, 3H), 1.22-2.56 (m, 19H), 3.05 (m, 2H), 6.76 (d, 1H), 7.06 (s, 1H), 7.31 (s, 1H). |

TABLE 1-continued

| # | Compound | NMR |
|---|---|---|
| 93 | | $^1$H-NMR (CDCl$_3$): 0.83 (s, 3H), 1.46-2.48 (m, 22H), 2.95 (m, 2H), 3.79 (s, 3H), 6.67 (m, 2H), 7.05 (s, 1H), 7.20 (d, 1H), 11.66 (br s, 1H). |
| 94 | | $^1$H-NMR (CDCl$_3$): 1.08 (s, 3H), 1.26-3.20 (m, 21H), 6.98 (d, 1H), 7.07 (s, 1H), 7.93 (d, 1H). |
| 95 | | $^1$H-NMR (DMSO-d$_6$): 0.96 (s, 3H), 1.20-2.95 (m, 19H), 6.45 (s, 1H), 6.48 (d, 1H), 7.02 (d, 1H), 7.08 (s, 1H), 7.72 (s, 1H), 9.01 (s, 1H) 12.43 (br s, 1H). |
| 96 | | $^1$H-NMR (CDCl$_3$): 1.12 (s, 3H), 1.30-3.0 (m, 19H), 7.0-7.3 (m, 5H). |

TABLE 1-continued

| # | Compound | NMR |
|---|---|---|
| 97 | (structure: 3-methoxy estrone-derived steroid with 16-hydroxymethylene and 15-(2-(N-(5-methylthiazol-2-yl)carbamoyl)ethyl) substituent) | ¹H-NMR (CDCl₃ + MeOH-d₄): 0.97 (t, 3H), 1.15-2.40 (m, 16H), 2.84 (m, 3H), 3.69 (s, 3H), 6.64 (s, 1H), 6.66 (d, 1H), 7.08 (s, 1H), 7.15 (d 1H), 8.13 (s, 1H). |
| 98 | (structure: 2-tert-butyl-3-hydroxy estrone-derived steroid with 16-hydroxymethylene and 15-(2-(N-(5-methylthiazol-2-yl)carbamoyl)ethyl) substituent) | ¹H-NMR (DMSO-d₆): 0.99 (s, 3H), 1.05-3.00 (m, 32H), 6.46 (s, 1H), 7.00 (s, 1H), 7.09 (s, 1H), 7.58 (s, 1H), 8.95 (s, 1H), 12.01 (s, 1H); |
| 99 | (structure: 2-bromo-3-hydroxy estrone-derived steroid with 16-hydroxymethylene and 15-(2-(N-(5-methylthiazol-2-yl)carbamoyl)ethyl) substituent) | ¹H-NMR (CDCl₃): 1.13 (s, 3H), 1.40-2.9 (m, 19H), 3.40 (s, 1H), 6.76 (d, 1H) 7.05 (s, 1H), 7.32 (d, 1H); |
| 100 | (structure: 4-bromo-3-hydroxy estrone-derived steroid with 16-hydroxymethylene and 15-(2-(N-(5-methylthiazol-2-yl)carbamoyl)ethyl) substituent) | ¹H-NMR (CDCl₃): 1.12 (s, 3H), 1.40-3.0 (m, 19H), 3.67 (s, 1H), 6.86 (d, 1H) 7.06 (s, 1H), 7.16 (d, 1H); |

TABLE 1-continued
| # | Compound | NMR |
|---|---|---|
| 101 | 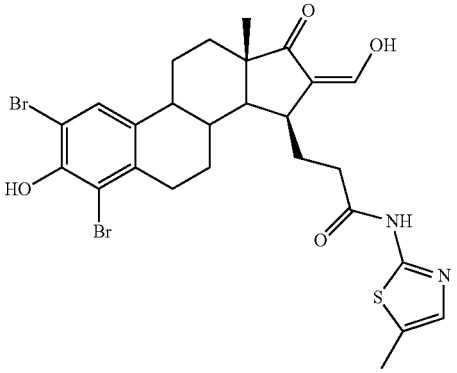 [SMILES: Cc1cnc(NC(=O)CC[C@@H]2/C(=C/O)C(=O)[C@@]3(C)CCC4c5cc(Br)c(O)c(Br)c5CCC4C23)s1] | $^1$H-NMR (DMSO-d$_6$): 0.96 (s, 3H), 1.20-3.00 (m, 19H), 7.09 (s, 1H), 7.39 (s, 1H), 7.55 (s, 1H), 9.53 (br s, 1H), 11.95 (br s, 1H). |
| 102 | 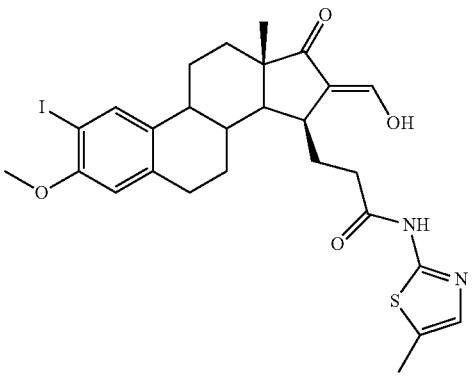 [SMILES: COc1cc2c(cc1I)C1CC[C@]3(C)C(=O)/C(=C/O)[C@@H](CCC(=O)Nc4ncc(C)s4)C3C1CC2] | $^1$H-NMR (CDCl$_3$): 1.14 (s, 3H), 1.20-2.97 (m, 20H), 3.85 (s, 3H), 6.57 (s, 1H), 7.07 (s, 1H), 7.63 (s, 1H); |
| 103 | 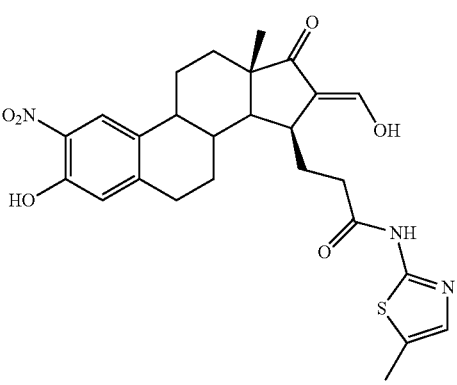 [SMILES: Cc1cnc(NC(=O)CC[C@@H]2/C(=C\O)C(=O)[C@@]3(C)CCC4c5cc([N+](=O)[O-])c(O)cc5CCC4C23)s1] | $^1$H-NMR (CDCl$_3$): 1.14 (s, 3H), 1.20-3.05 (m, 19H), 6.88 (s, 1H), 7.04 (s, 1H), 7.23 (s, 1H), 7.97 (s, 1H). |
| 104 | 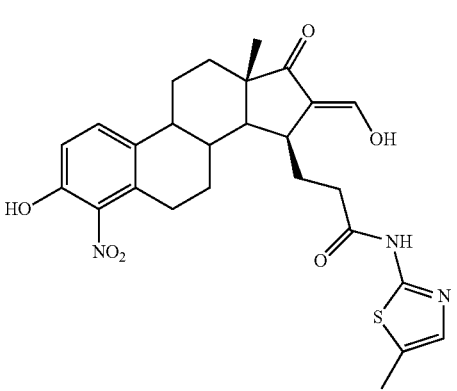 [SMILES: Cc1cnc(NC(=O)CC[C@@H]2/C(=C\O)C(=O)[C@@]3(C)CCC4c5ccc(O)c([N+](=O)[O-])c5CCC4C23)s1] | $^1$H-NMR (CDCl$_3$): 1.14 (s, 3H), 1.30-3.35 (m, 19H), 6.97 (d, 1H), 7.06 (d, 1H), 7.44 (d, 12H). |

TABLE 1-continued

| # | Compound | NMR |
|---|---|---|
| 105 | 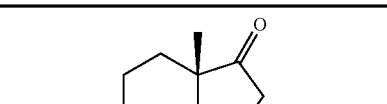 | $^{1}$H-NMR (CDCl$_3$): 1.06 (s, 3H), 1.31 (s, 9H), 1.40-2.20 (m, 10H), 2.33-2.67 (m, 9H), 2.92 (m, 2H), 7.04-7.33 (m, 4H), 12.32 (s, 1H). |

Compounds of this invention are also useful in the form of acid or base addition salts, hydrates, or solvates thereof.

General Preparation Methods

Compounds of the present invention may be prepared by methods known in the art.

The following examples illustrate the preparation of compounds of formula (I).

General Information

Commercial grade reagents and solvents were used without further purification. Thin-layer chromatography (TLC) was performed on Merck-plates; pre-coated aluminum sheets. Visualization of plates was done the following techniques: 1) ultraviolet illumination (254 nm), 2) dipping the plate into anisaldehyde or vanillin solution followed by heating. 1H-NMR spectra were measured with a Bruker DPX (200 MHz) spectrometer with the solvent as indicated.

Preparation of Synthesis Starting Materials and Precursors

Compound VII may be synthesized as disclosed in Messinger et al. Mol Cell Endocrinol. 2009 (301) 216-224. The detailed synthesis of compound VII starting from estrone has been described in the Solvay Pharmaceuticals' PCT applications WO2005/047303 and WO2006/125800.

Benzyl-C15-C16-dehydroestrone II was prepared in five steps from estrone according to previously described methods. The compound II was treated with an allylic Grignard reagent in the presence of cuprous iodide and lithium chloride in temperature −78° C. Hydroboration by borane tetrahydrofuran complex at room temperature (rt) to compound III and following hydrogen peroxide oxidation in alkaline conditions produced diol IV in over 90% yields. Jones oxidation in acetone-water afforded acid V, which was debenzylated by hydrogenation to compound VI by using Pd/C as a catalyst. The final step was the amide formation affording the β-thiazole VII.

The phenolic VII was acetylated by using acetyl chloride or acetic anhydride in the presence of pyridine to the compound 1. The synthesis of the key precursor i.e. the phenolic thiazole VII is shown below.

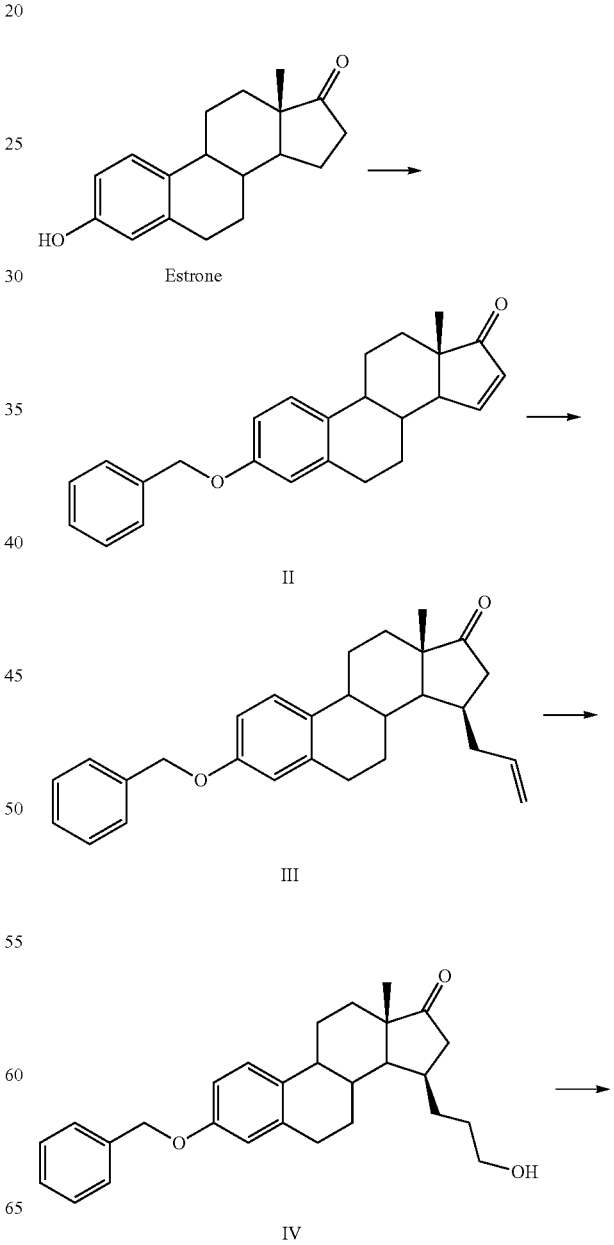

73
-continued

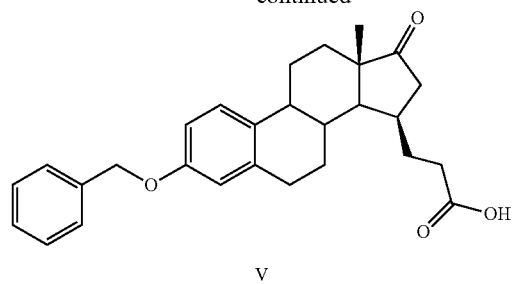

V

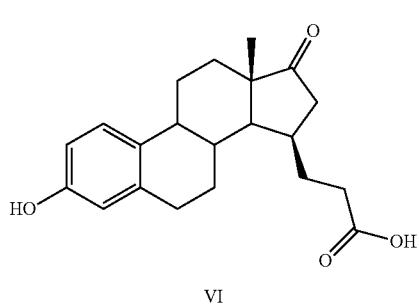

VI

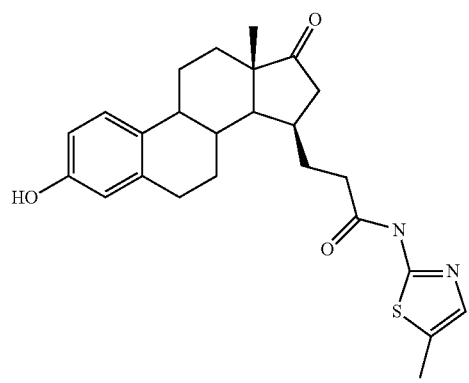

VII

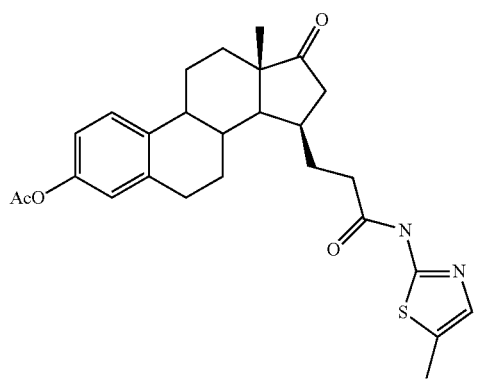

1

74

C-3 Methylation

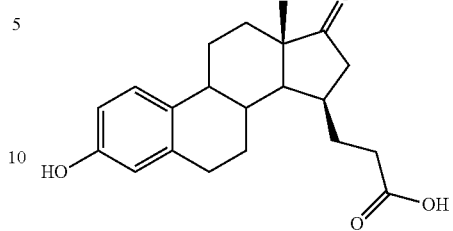

VI

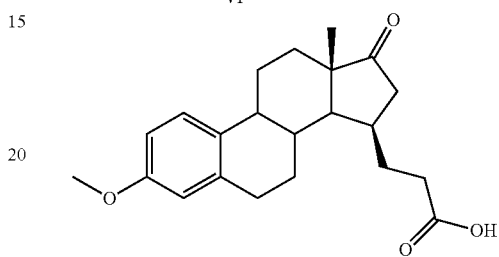

IX

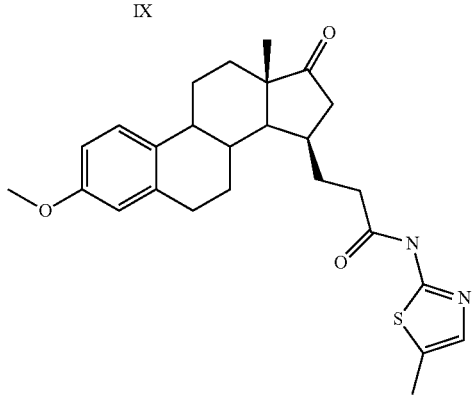

X

Compound IX 3-((13S,15R)-3-Methoxy-13-methyl-17-oxo-7,8,9,11,12,13,14,15,16,17-decahydro-6H-cyclopenta[a]phenanthren-15-yl)propionic acid The compound VI (2.0 g, 100 mol-%) was dissolved in acetone (40 ml). Potassium carbonate (200 mol-%) and methyl iodide (500 mol-%) were added and stirred at rt overnight. Additional amounts of methyl iodide (200 mol-%) and potassium carbonate (100 mol-%) were added and refluxed for 10 hours. The solvent was evaporated. The precipitate was dissolved in methanol (50 ml) and 2M NaOH-solution was added until pH was >12. The reaction mixture was stirred at rt for 4 hours. The reaction mixture was acidified by HCl. The product was extracted with dichloromethane (DCM) (3×30 ml), washed several times with water and finally with brine. The amount of the product IX was 1.95 g; the yield was 94%.

$^1$H-NMR (CDCl$_3$): 1.05 (s, 3H), 1.45-2.48 (m, 19H), 2.93 (m, 2H), 3.79 (s, 3H), 6.70 (m, 2H), 7.20 (d, 1H).

Compound X 3-((13S,15R)-3-Methoxy-13-methyl-17-oxo-7,8,9,11,12,13,14,15,16,17-decahydro-6H-cyclopenta[a]phenanthren-15-yl)-N-(5-methylthiazol-2-yl)propanamide The amide coupling: The compound IX (2.0 g, 100 mol-%) was dissolved in dry DCM (80 ml). 2-Amino-5-methylthiazol (200 mol-%), N-methylmorpholine (NMM) (300 mol-%) ja 1-hydroxy-1H-benzotriazole (HOBT) (170 mol-%) were added. The reaction mixture was stirred for five minutes, cooled to 0-5° C. and 1-ethyl-3-(3'dimethylaminopropyl)carbodiimide hydrochloride (EDCI) (220 mol-%) was added. The reaction mixture was stirred at room temperature (rt) overnight and then diluted with DCM, washed with 1N HCl-solution and 5% KOH-solution. The organic phase was finally washed with water and brine. The crude product was purified by chromatography affording 1.85 of the product X; the yield was 73%.

$^1$H-NMR (CDCl$_3$): 1.06 (s, 3H), 1.37-2.60 (m, 22H), 2.90 (m, 2H), 3.79 (s, 3H), 6.70 (m, 2H), 7.05 (s, 1H), 7.19 (d, 1H), 12.11 (s, 1H).

Esterification
General Method for the Preparation of C-3 Esters

The compound VII (100 mol-%) was dissolved in DCM (15 ml). Pyridine (1000 mol-%) and a suitably selected acid chloride or anhydride (500 mol-%) were added. The reaction was refluxed for 1-4 hours followed by TLC. DCM was added and reaction mixture washed with water, 1N HCl, water and brine. The reaction was dried with Na$_2$SO$_4$ and the solvent was evaporated. The crude product was purified by flash chromatography.

Compound 1

Acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

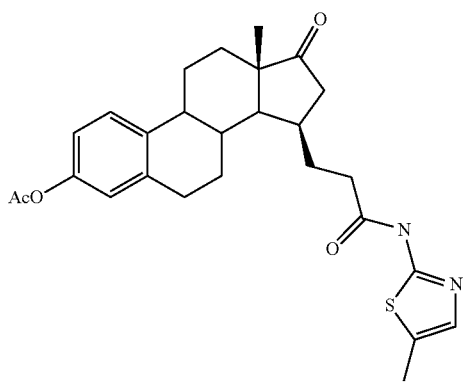 [SMILES: CC(=O)Oc1ccc2c(c1)CCC1C2CC[C@]2(C)C(=O)C[C@@H](CCC(=O)Nc3ncc(C)s3)C12]

The compound VII (100 mol-%) was dissolved in DCM (15 ml). Pyridine (1000 mol-%) and acetic anhydride (500 mol-%) were added. The reaction was refluxed for 1-4 hours followed by TLC. DCM was added and reaction mixture washed with water, 1N HCl, water and brine. The reaction was dried with Na$_2$SO$_4$ and the solvent was evaporated. The crude product was purified by flash chromatography. The yield of the C-3 acetylated 1 was 86%.

$^1$H-NMR (DMSO-d$_6$): 0.98 (s, 3H), 1.35-2.40 (m, 22H), 2.86 (m, 2H), 6.83-6.87 (m, 2H), 7.11 (s, 1H), 7.29 (d, 1H), 11.91 (s, 1H). MS m/z (TOF ES$^+$): 503 (M+Na).

Compound 2

Methanesulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

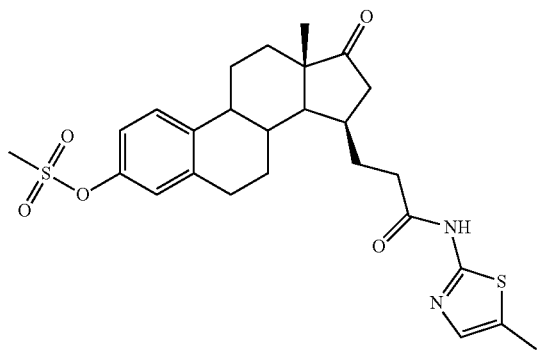

Prepared according to the general method from the compound VII using mesyl chloride as a reagent in 65% yield.

$^1$H-NMR (DMSO-d$_6$): 0.97 (s, 3H), 1.36-2.40 (m, 22H), 2.91 (m, 2H), 6.82-6.86 (m, 2H), 7.09 (s+d, 3H), 7.37 (d, 1H), 11.91 (s, 1H). MS m/z (TOF ES$^+$): 539 (M+Na), 517 (M+1).

Compound 3

2,2-Dimethyl-propionic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

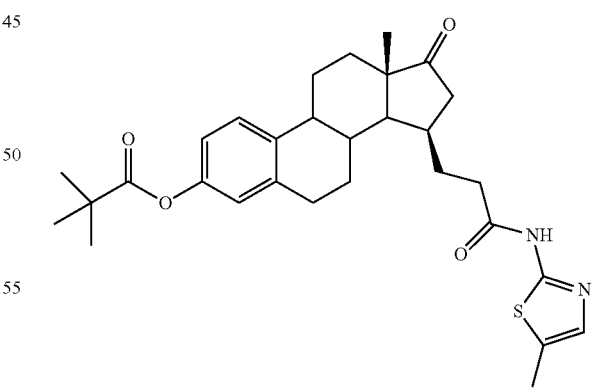

Prepared from the compound VII according to the general method described for the compound 1 using pivaloyl chloride as a reagent in 67% yield.

$^1$H-NMR (DMSO-d$_6$): 0.97 (s, 3H), 1.28 (s, 9H, 3×Me), 1.35-2.40 (m, 19H), 2.86 (m, 2H), 6.79-6.83 (m, 2H), 7.11 (s, 1H), 7.28 (d, 1H), 11.92 (s, 1H). MS m/z (TOF ES$^+$): 545 (M+Na).

Compound 4

Sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

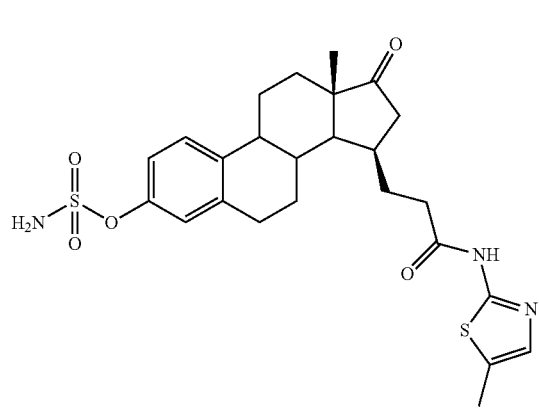 [SMILES: Cc1cnc(NC(=O)CC[C@@H]2CC(=O)[C@@]3(C)CCC4c5ccc(OS(N)(=O)=O)cc5CCC4C23)s1]

Prepared from the compound VII according to the general method described for the compound 1 using sulfamoyl chloride as a reagent.

$^{1}$H-NMR (DMSO-d$_{6}$): 0.97 (s, 3H), 1.30-2.40 (m, 19H), 2.86 (m, 2H), 7.00-7.37 (m, 4H), 7.92 (s, 2H), 11.92 (s, 1H). MS m/z (TOF ES$^{+}$): 540 (M+Na).

Compound 5

Sulphuric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester triethylamine salt

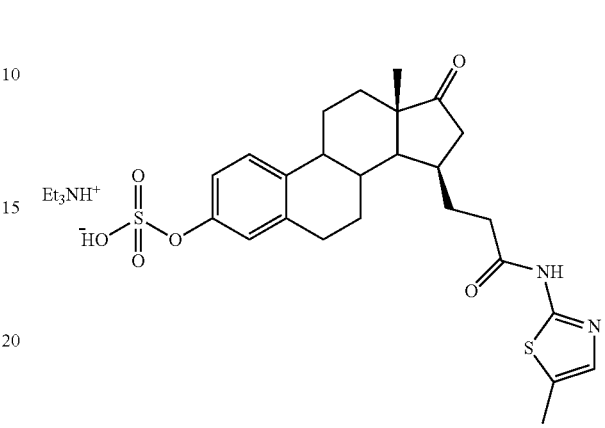

The compound VII (1.5 g, 100 mol-%) was dissolved in dry DMF (15 ml). Sulfur trioxide-triethylamine complex (240 mol-%) was added. Additional amount of sulfur trioxide-triethylamine complex (240 mol-%) was added after 4 hours. Stirring was continued at rt for two days. Silica gel (15 g) was added and the solvent was gently evaporated (bath ca. 35° C.). The precipitate was purified by chromatography.

$^{1}$H-NMR (DMSO-d$_{6}$): 0.97 (s, 3H), 1.16 (t, 9H), 1.30-2.40 (m, 19H), 2.83 (m, 2H), 3.09 (q, 6H), 6.88-6.90 (m, 2H), 7.11-7.17 (m, 2H), 11.91 (s, 1H). MS m/z (TOF ES$^{+}$): 721 (M+NEt$_{3}$); MS m/z (TOF ES$^{-}$): 517 (M−NEt$_{3}$).

Compounds 6 to 8

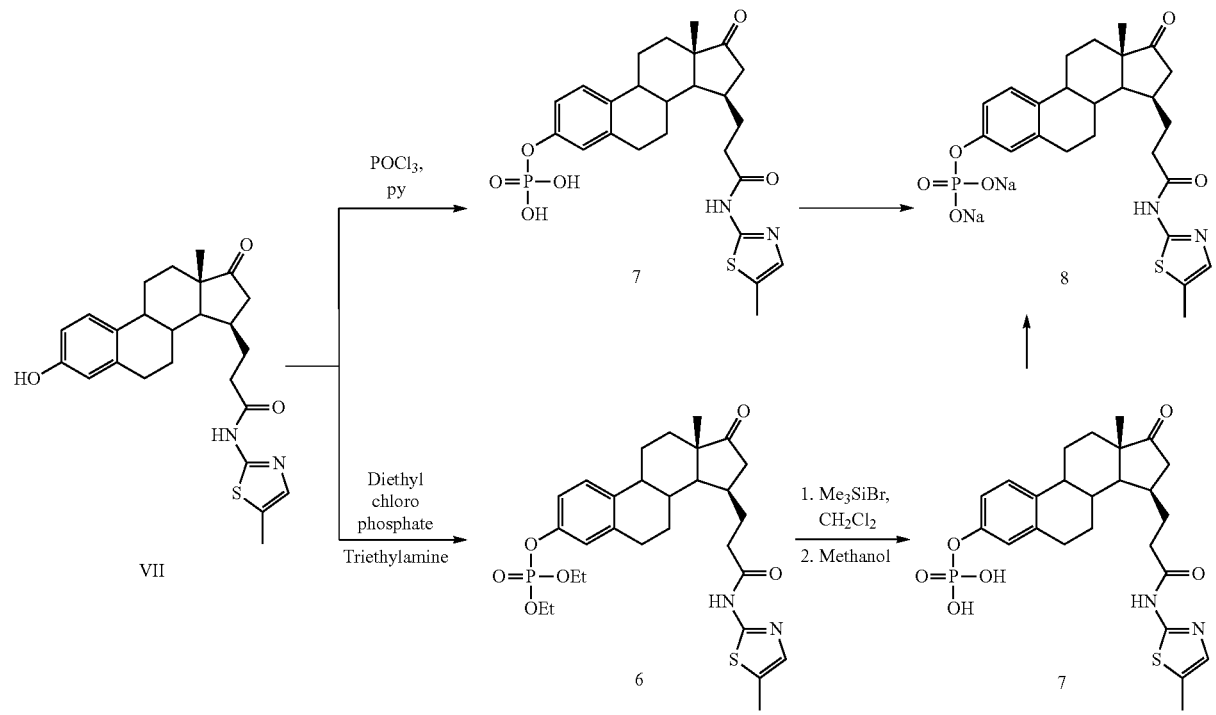

Compound 6

Phosphoric acid diethyl ester (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

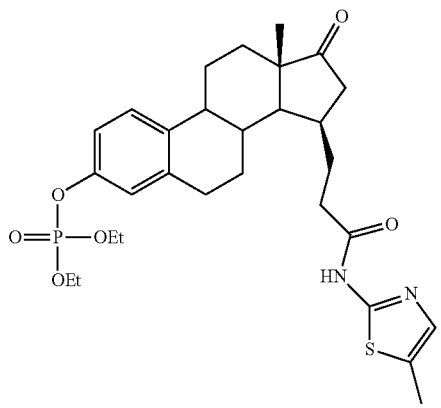 [SMILES: CCOP(=O)(OCC)Oc1ccc2c(c1)CCC1C2CC[C@]2(C)C(=O)C[C@@H](CCC(=O)Nc3ncc(C)s3)C12]

The compound VII (500 mg, 100 mol-%), diethylchlorophosphate (200 mol-%) and dry triethylamine (TEA) (200 mol-%) were dissolved in dry DCM (10 ml), and refluxed for 15 hours. The reaction mixture was diluted with DCM (30 ml), washed with sat. NaHCO$_3$ (2×20 ml) and brine (20 ml) and dried over sodium sulphate. The solvent was evaporated and the product was purified by chromatography.

$^1$H-NMR (DMSO-d$_6$): 0.96 (t, 3H), 1.27 (2×t, 6H), 1.30-2.40 (m, 19H), 2.86 (m, 2H), 4.07-4.22 (m, 4H), 6.91 (s, 1H), 6.95 (s, 1H), 7.10 (s, 1H), 7.28 (d, 1H). MS m/z (TOF ES$^+$): 575 (M+1).

Compound 7

Phosphoric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester

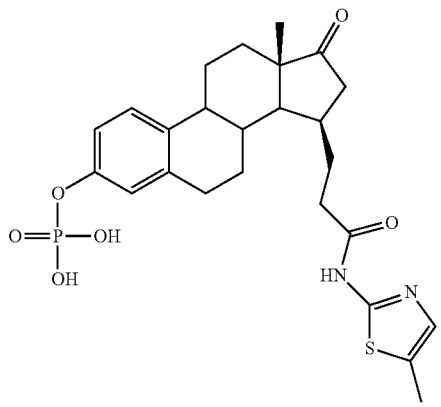 [SMILES: Cc1cnc(NC(=O)CC[C@@H]2CC(=O)[C@@]3(C)CCC4c5ccc(OP(=O)(O)O)cc5CCC4C23)s1]

The compound VII (2.0 g) and pyridine (200 mol-%) were dissolved in THF (20 ml) and phosphorous oxychloride (200 mol-%) was added dropwise during 10 minutes under nitrogen atmosphere to the reaction mixture. The reaction mixture was stirred at rt for 3.5 hours. Water (80 ml) was added dropwise cooling with ice-bath and stirred for one hour. The product was filtered, washed carefully with water. The product 7 was isolated in a quantitative yield.

$^1$H-NMR (DMSO-d$_6$): 0.97 (s, 3H), 1.35-2.40 (m, 19H), 2.85 (m, 2H), 6.89 (s, 1H), 6.92 (s, 1H), 7.12 (s, 1H), 7.24 (d, 1H), 11.92 (s, 1H). MS m/z (TOF ES$^+$): 541 (M+Na), 519 (M+1).

Compound 8

Phosphoric acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester disodium salt

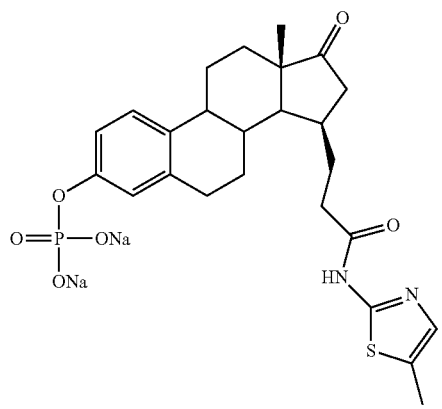

NaOH (240 mol-%) in ethanol (10 ml) was added to the reaction mixture of compound 7 (2.0 g, 100 mol-%) in ethanol (10 ml), and stirred at rt for 60 minutes. Diethyl ether (40 ml) was added and the precipitated product was filtered and washed carefully with ether-ethanol (v/v 1:1). The yield of the product 8 was 1.99 g.

$^1$H-NMR (D$_2$O): 0.94 (s, 3H), 1.35-2.40 (m, 19H), 2.78 (m, 2H), 6.89 (s, 1H), 6.92 (s, 1H), 7.14-7.18 (m, 2H). MS m/z (TOF ES$^+$): 585 (M+Na), 563 (M+1).

Compound 9

Succinic acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester

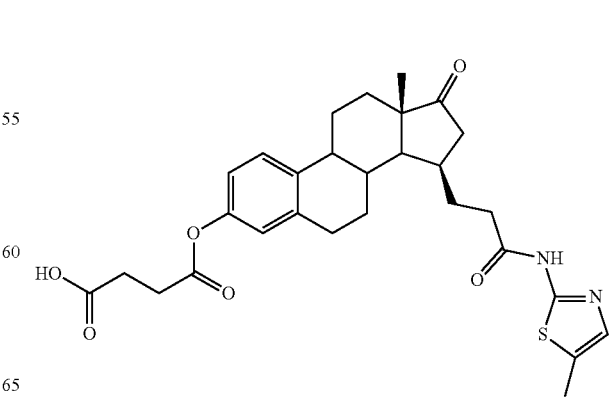

Prepared from the compound VII according to the general method described for the compound 1 using succinic anhydride as a reagent in 30% yield.

$^1$H-NMR (DMSO-$d_6$): 0.98 (s, 3H), 1.36-1.45 (m, 3H), 1.72 (m, 4H), 1.89-2.4 (m, 12H), 2.54-2.61 (m, 2H), 2.76-2.90 (m, 4H), 6.81 (s, 1H), 6.83 (d, 1H), 7.12 (s, 1H), 7.30 (d, 1H), 11.96 (s, 1H).

Compound 10

Succinic acid mono-{(13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl} ester sodium salt

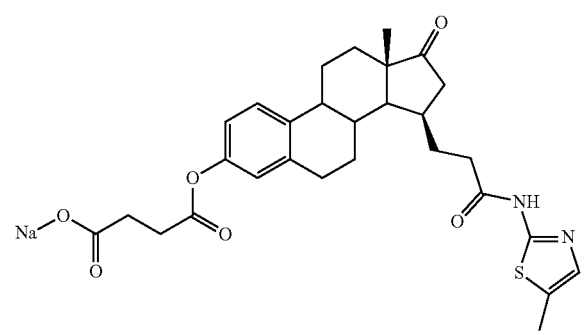

Prepared from the compound 9 dissolving in ethanol and adding 40% NaOH-water solution until pH was basic. The precipitated crystals were filtered.

$^1$H-NMR (DMSO-$d_6$): 0.96 (s, 3H), 1.31-1.38, (m, 3H), 1.61-1.79 (m), 1.99-2.23 (m), 2.33 (s, 3H), 2.76-2.79 (m, 2H), 2.89 (s, 4H), 6.47 (s, 1H), 6.51 (d, 1H), 7.04 (d, 1H), 7.11 (s, 1H), 11.93 (s, 1H).

Compound 11

Acetylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

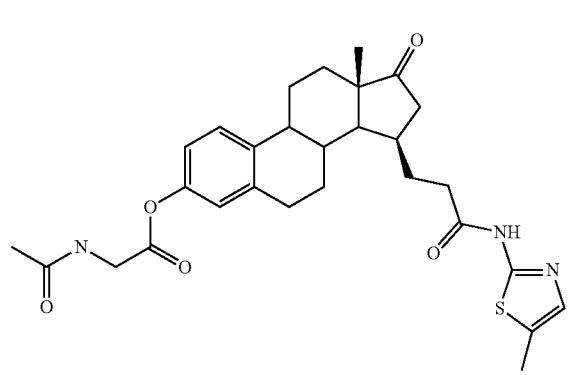 [SMILES: CC(=O)NCC(=O)Oc1ccc2c(c1)CCC1C2CC[C@]2(C)C(=O)C[C@@H](CCC(=O)Nc3ncc(C)s3)C12]

Prepared from the compound VII (1.0 g, 100 mol-%) and N-acetyl glycine (200 mol-%) using the amide coupling conditions described for the compound X.

$^1$H-NMR (DMSO-$d_6$): 0.98 (s, 3H), 1.37-1.73 (m, 6H), 1.90 (s, 3H), 2.27-2.89 (m, 9H), 3.98-4.07 (m, 2H), 6.83-6.87 (m, 2H), 7.11 (s, 1H), 7.31 (d, 1H), 8.46 (m, 1H), 11.92 (s, 1H). MS m/z (TOF ES$^+$): 560 (M+Na).

Compound 12

Pentanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

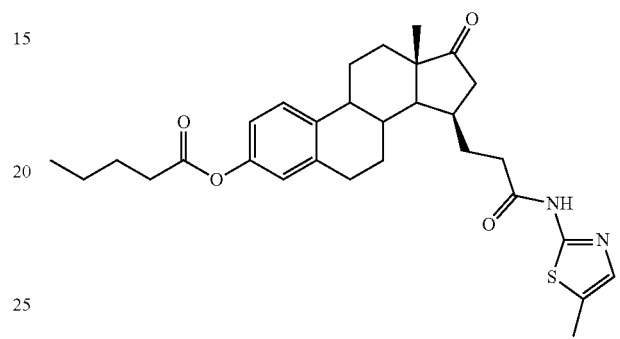

Prepared from the compound VII according to the general method described for the compound 1 using valeroyl chloride as a reagent in 60% yield.

$^1$H-NMR (DMSO-$d_6$): 0.92 (t, 3H), 0.99 (s, 3H), 1.24-2.59 (m, 25H), 2.87 (m, 2H), 6.82-6.86 (m, 2H), 7.11 (s, 1H), 7.30 (d, 1H), 11.92 (s, 1H). MS m/z (TOF ES$^+$): 545 (M+Na).

Compound 13

3-Cyclopentyl-propionic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

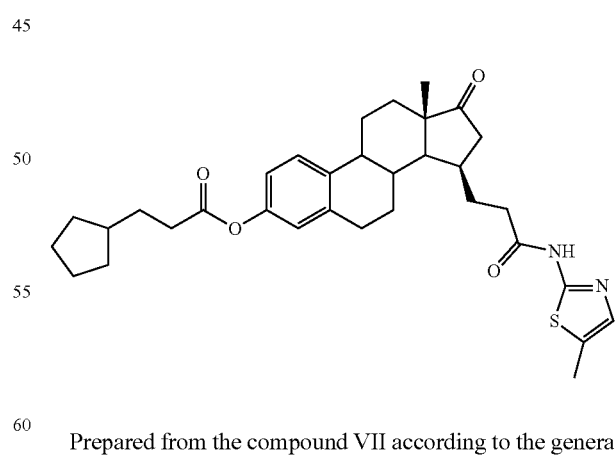

Prepared from the compound VII according to the general method described for the compound 1 using cyclopentane propionyl chloride as a reagent in 78% yield.

$^1$H-NMR (DMSO-$d_6$): 0.97 (s, 3H), 1.11 (m, 2H), 1.35-1.76 (m), 2.32 (s, 3H), 2.86 (m, 2H), 6.83 (m, 2H), 7.11 (s, 1H), 7.29 (d, 1H), 11.91 (s, 1H). MS m/z (TOF ES+): 585 (M+Na), 563 (M+1).

Compound 14
Dodecanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester
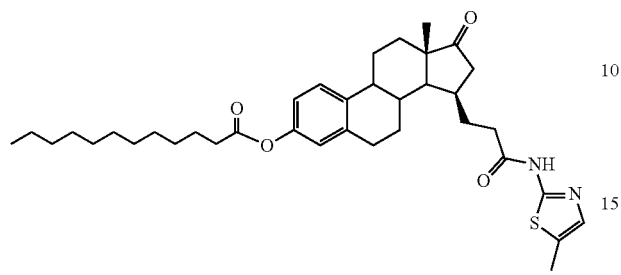
Prepared from the compound VII according to the general method described for the compound 1 using lauroyl chloride as a reagent in 60% yield.
$^1$H-NMR (DMSO-$d_6$): 0.85 (t, 3H), 0.98 (s, 3H), 1.25-2.50 (m, 39H), 2.87 (m, 2H), 6.81-6.86 (m, 2H), 7.11 (s, 1H), 7.29 (d, 1H), 11.91 (s, 1H). MS m/z (TOF ES+): 643 (M+Na).
Compounds 15 and 16
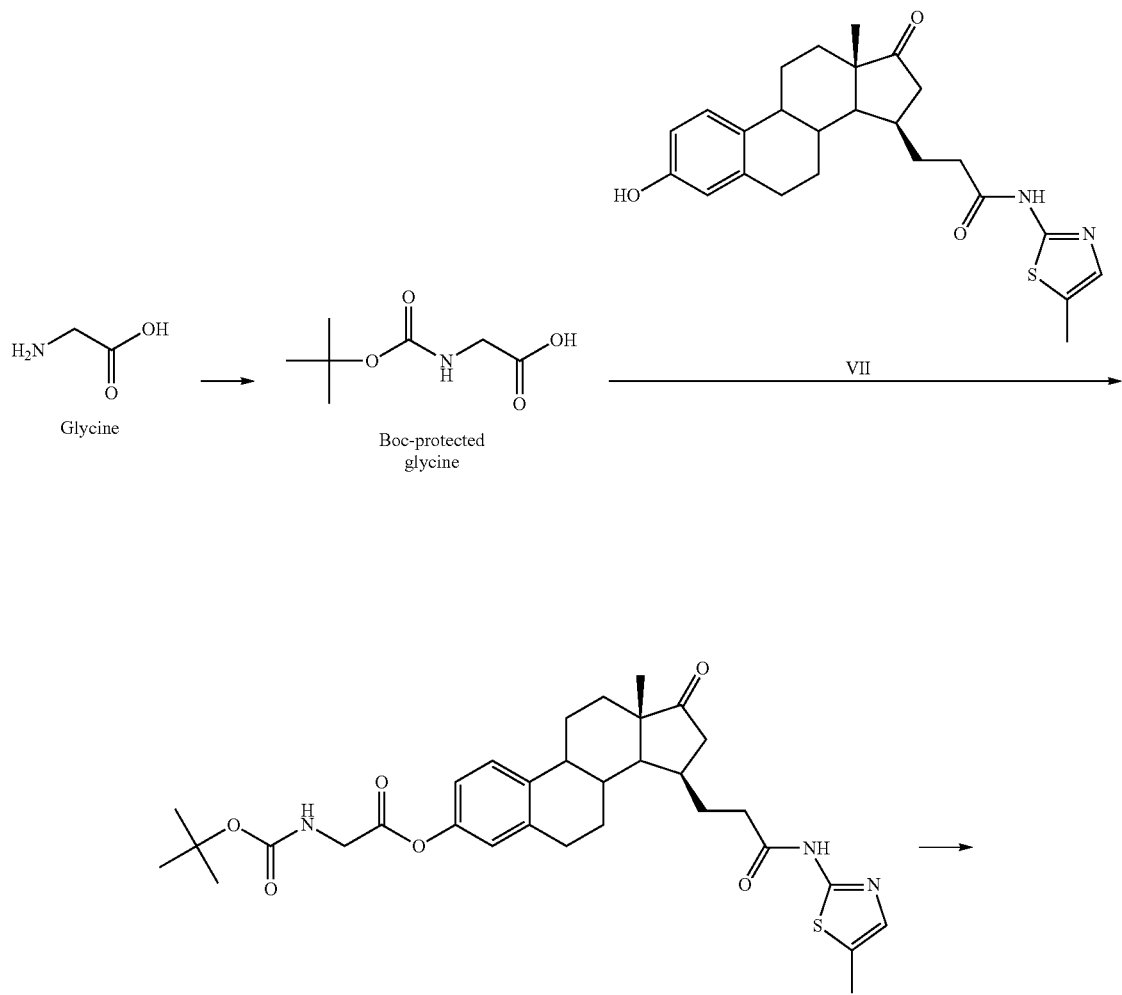

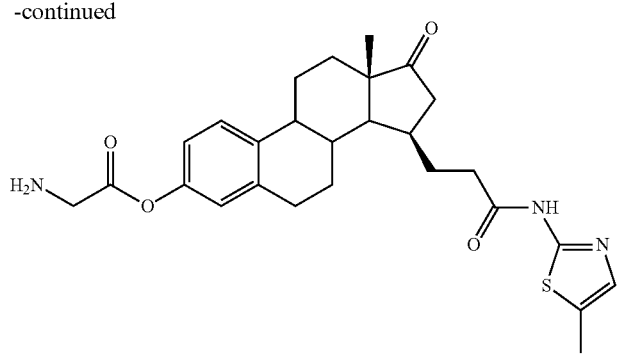

16

Compound 15 tert-Butoxycarbonylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

Compound 16

Amino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

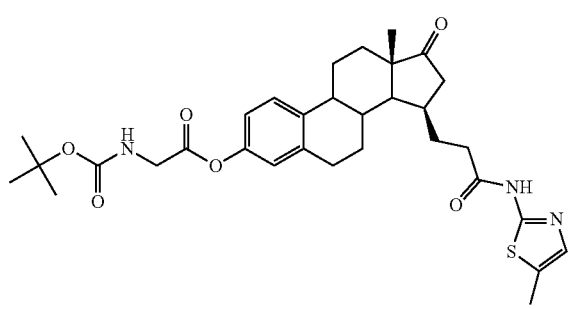 [SMILES: Cc1cnc(NC(=O)CC[C@@H]2CC(=O)[C@@]3(C)CCC4c5ccc(OC(=O)CNC(=O)OC(C)(C)C)cc5CCC4C23)s1]

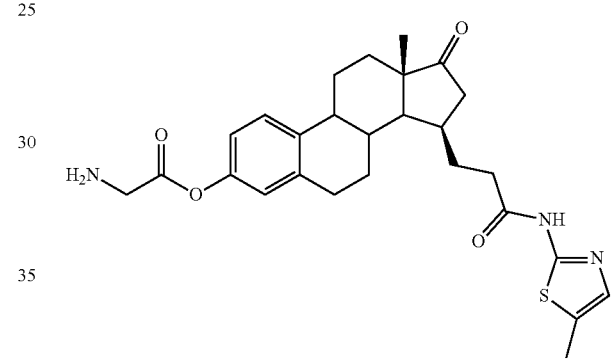

Boc-protection of glycine: Glycine (1.5 g, 100 mol-%) was dissolved in a mixture of 1,4-dioxane (16 ml) and water (8 ml). The mixture was cooled and 1M NaOH (42 ml) and di-tert-butyl pyrocarbonate (4.8 g) were added. After stirring for 60 minutes at 0° C. followed by overnight at rt, the reaction mixture was acidified with conc. citric acid. The product was extracted with EtOAc (3×50 ml), washed with brine and dried with Na$_2$SO$_4$.

$^1$H-NMR (CDCl$_3$): 1.46 (s, 9H), 3.96 (m, 2H), 5.09 (br s, 1H), 9.69 (br s, 1H). MS m/z (TOF ES$^+$): 198 (M+Na).

The compound VII (500 mg, 100 mol-%) and the Boc-protected glycine (200 mol-%) were dissolved in dry DCM (20 ml). NMM (300 mol-%) and HOBT (170 mol-%) were added to the reaction mixture. After stirring for five minutes, the reaction mixture was cooled with ice-bath. EDCI (220 mol-%) was added. The reaction mixture was stirred overnight at rt. After dilution with DCM the reaction mixture was washed several times with 1H HCl-solution. The organic phase was washed with water and brine.

$^1$H-NMR (DMSO-d$_6$): 0.98 (s, 3H), 1.40 (s, 9H), 1.7-2.5 (m), 2.32 (s, 3H), 2.87 (m, 2H), 3.93 (d, 2H, —CH2), 6.84 (m, 2H), 7.11 (s, 1H), 7.15-7.42 (m, 3H), 11.91 (s, 1H). MS m/z (TOF ES$^+$): 596 (M+1).

The compound 15 (400 mg, 100 mol-%) was dissolved in dry DCM (1 ml). To the cooled mixture trifluoroacetic acid (TFA) (1.6 ml) was added. After stirring for an hour the solvent was evaporated. The precipitate was triturated with diethyl ether.

$^1$H-NMR (DMSO-d$_6$): 0.98 (s, 3H), 1.41 (m), 1.7-2.5 (m), 2.33 (s, 3H), 2.90 (m, 2H), 4.11 (br s, 2H), 6.93 (m, 2H), 7.11 (s, 1H), 7.36 (2×s, 2H), 8.37 (br s, 2H), 11.92 (s, 1H). MS m/z (TOF ES$^+$): 496 (M+1).

Compound 17

Undec-10-enoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

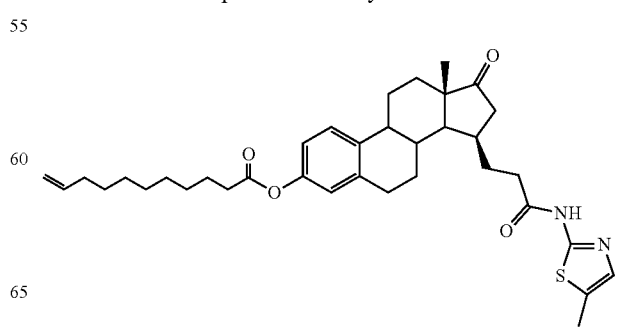

Prepared from the compound VII according to the general method described for the compound 1 using 10-undecenoyl chloride as a reagent in 80% yield.

¹H-NMR (DMSO-d₆): 0.98 (s, 3H), 1.29-2.56 (m, 35H), 2.86 (m, 2H), 4.91-5.05 (m, 2H), 5.69-5.89 (m, 1H), 6.81-6.85 (m, 2H), 7.11 (s, 1H), 7.29 (d, 1H), 11.92 (s, 1H). MS m/z (TOF ES⁺): 605 (M+1).

Compound 18

Hexadecanoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

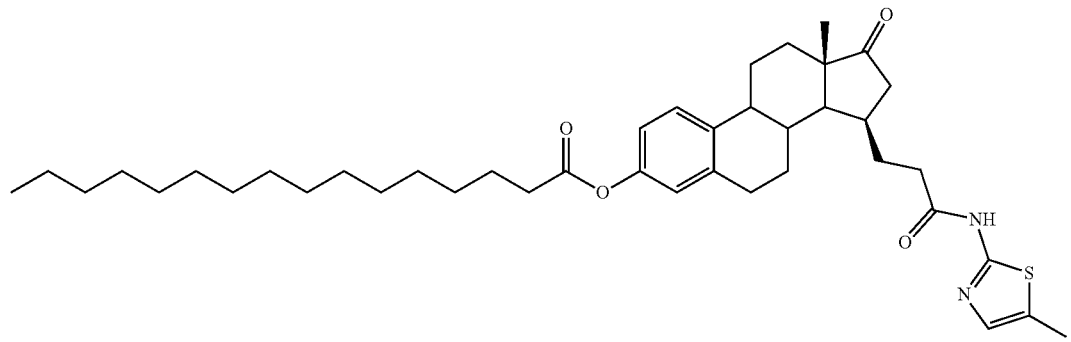 [SMILES: CCCCCCCCCCCCCCCC(=O)Oc1ccc2c(c1)CCC1C2CC[C@]2(C)C(=O)C[C@@H](CCC(=O)Nc3ncc(C)s3)C12]

Prepared from the compound VII according to the general method described for the compound 1 using palmitoyl chloride as a reagent in 81% yield.

¹H-NMR (DMSO-d₆): 0.84 (t, 3H), 0.99 (s, 3H), 1.22-2.46 (m, 47H), 2.88 (m, 2H), 6.77-6.81 (m, 2H), 7.05 (s, 1H), 7.25 (d, 1H), 11.86 (s, 1H). MS m/z (TOF ES⁺): 700 (M+Na).

Compound 19

2-Acetoxy-benzoic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

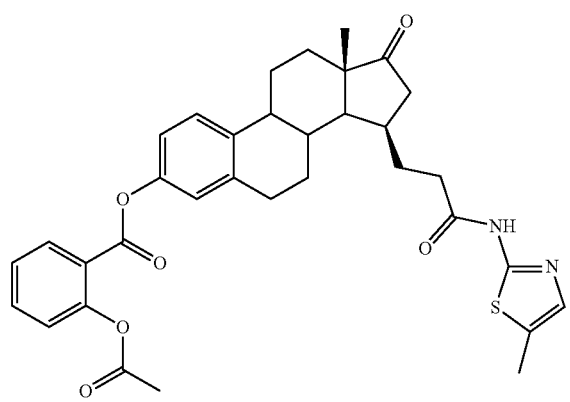 [SMILES: CC(=O)Oc1ccccc1C(=O)Oc1ccc2c(c1)CCC1C2CC[C@]2(C)C(=O)C[C@@H](CCC(=O)Nc3ncc(C)s3)C12]

Thionylchloride (1000 mol-%) was added to acetosalicylic acid (300 mol-%) in DCM (8 ml). A few drops of DMF were added. After refluxing for 45 minutes the solvent was evaporated. The precipitate was dissolved in dry DCM and added to the mixture of VII (200 mg, 100 mol-%) and TEA (500 mol-%) in DCM (8 ml) under nitrogen atmosphere, and stirred at rt for 24 hours. The reaction mixture was diluted with DCM, washed with water, 1N HCl and brine. The crude product was washed with ethanol.

¹H-NMR (DMSO-d₆): 0.98 (s, 3H), 1.42 (m), 1.6-2.4 (m), 2.23 (s, 3H), 2.32 (s, 3H), 2.90 (m, 2H), 6.95 (m, 2H), 7.10 (s, 1H), 7.33 (dd, 2H), 7.48 (dd, 1H), 7.77 (dd, 1H), 8.13 (d, 1H), 11.91 (s, 1H). MS m/z (TOF ES⁺): 601 (M+1).

Carbonic Acid Esters

Compound 20

Ethyl ((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl) carbonate

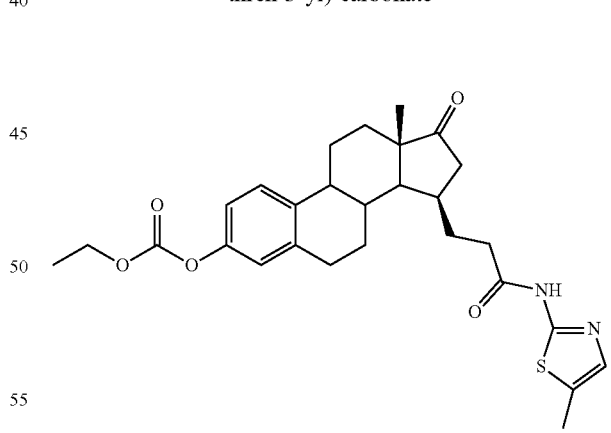

Synthesis was carried out by the same method as for the compound 22, using ethyl chloroformate instead of octylchloroformate; the yield 40 mg (78%, purity 99.3%, 275 nm) after chromatography.

¹H-NMR (DMSO-d₆): 0.98 (s, 3H), 1.28 (t, 3H), 1.35-2.40 (m, 19H), 1.48 (s, 9H) 2.88 (m, 2H), 4.22 (q, 2H), 6.93 (s, 1H), 6.95 (d, 1H) 7.11 (s, 1H), 7.31 (d, 1H), 11.92 (s, 1H). MS m/z (TOF ES⁺): 511 (M+1), 533 (M+Na).

Compound 21

Tert-butyl ((13S,15R)-13-methyl-15-(3-((5-methyl-thiazol-2-yl)amino)-3-oxopropyl)-17-oxo-7,8,9,11,12,13,14,15,16,17-decahydro-6H-cyclopenta[a]phenanthren-3-yl) carbonate

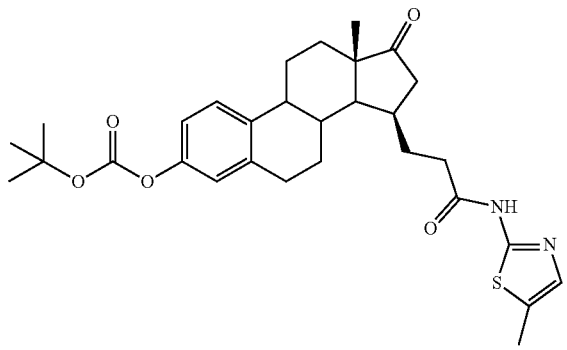 [SMILES: Cc1cnc(NC(=O)CC[C@@H]2CC(=O)[C@@]3(C)CCC4c5ccc(OC(=O)OC(C)(C)C)cc5CCC4C23)s1]

Di-tert-butylpyrocarbonate (44 mg, 0.2 mmol) was added at 0° C. to the reaction mixture of the compound VII (44 mg, 0.1 mmol) and TEA (50 mg, 0.5 mmol) in DCM (1 ml). Stirring was continued at 0° C. for 10 minutes, then the reaction mixture was allowed to warm to rt. Pyrocarbonate (50 μl) was added and stirring was continued at rt. Additional amount of pyrocarbonate (50 μl) was added and reaction was stirred overnight. 4-Dimethylaminopyridine (DMAP) (2 mg) was added and after 1.5 hours reaction was completed. Reaction mixture was poured into ice-water and extracted with DCM, washed with water, dried and evaporated. Finally the product was purified by flash chromatography giving quantitative yield of compound 21.

$^1$H-NMR (DMSO-d$_6$): 0.98 (s, 3H), 1.25-2.40 (m, 19H), 1.48 (s, 9H) 2.87 (m, 2H), 6.89 (s, 1H), 6.91 (d, 1H) 7.11 (s, 1H), 7.29 (d 1H), 11.92 (s, 1H). MS m/z (TOF ES$^+$): 539 (M+1), 561 (M+Na).

Compound 22

(13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl octyl carbonate

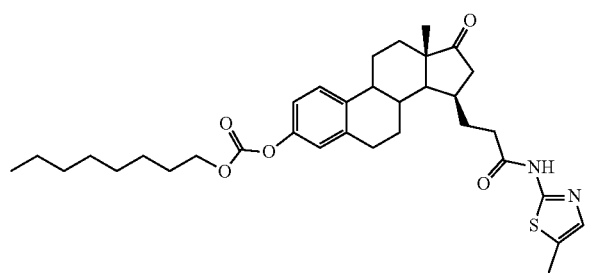 [SMILES: CCCCCCCCOC(=O)Oc1ccc2c(c1)CCC1C2CC[C@]2(C)C(=O)C[C@@H](CCC(=O)Nc3ncc(C)s3)C12]

Octylchloroformate (39 mg) was added at 0° C. to the reaction mixture of the compound VII (44 mg, 0.1 mmol) and TEA (50 mg, 0.5 mmol) in DCM (1 ml). Stirring was continued at 0° C. for 30 minutes. The reaction mixture was poured into ice-water and extracted with DCM, washed with water, dried and evaporated. Finally the product was purified by flash chromatography giving 43 mg of the compound 22; 72% yield.

$^1$H-NMR (CDCl$_3$+MeOH-d$_4$): 0.86 (t, 3H), 0.98 (t, 3H), 1.20-2.40 (m, 31H), 2.87 (m, 2H), 4.17 (t, 2H), 6.93 (s, 1H), 6.95 (d, 1H), 7.11 (s, 1H), 7.30 (d, 1H), 11.91 (s, 1H). MS m/z (TOF ES$^+$): 595 (M+1).

Compound 23

Dimethyl-sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

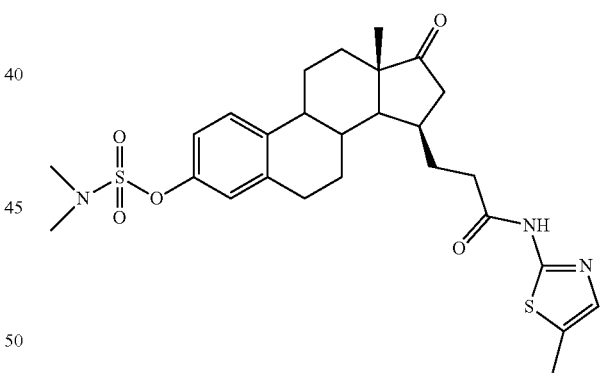

N,N-dimethylsulfamoyl chloride (300 mol-%) was added to the mixture of the compound VII (100 mg, 100 mol-%) and TEA (300 mol-%) in dry DCM at 0° C. Stirred at rt for two days, concentrated and purified by chromatography using DMC:EtOAc as an eluent (gradient from 100:0 to 75:25).

$^1$H-NMR (DMSO-d$_6$): 0.98 (s, 3H), 1.41 (m), 1.6-2.4 (m), 2.33 (s, 3H), 2.91 (s, 6H), 7.04 (s, 1H), 7.11 (m, 2H), 7.36 (d, 1H), 11.92 (s, 1H). MS m/z (TOF ES$^+$): 546 (M+1).

Carbamates

Compound 24

Morpholine-4-carboxylic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

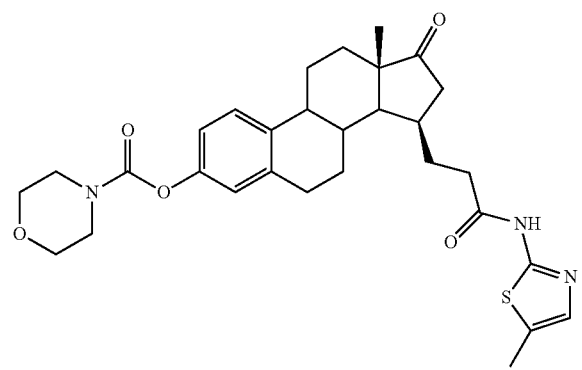 [SMILES: Cc1cnc(NC(=O)CC[C@@H]2CC(=O)[C@@]3(C)CCC4c5ccc(OC(=O)N6CCOCC6)cc5CCC4C23)s1]

Morfolinocarbonylchloride (30 mg) was added at 0° C. under nitrogen atmosphere into a mixture of the compound VII (44 mg, 0.1 mmol) and TEA (70 µl, 0.5 mmol) in DCM (1 ml). Reaction was allowed to warm and stirring was continued at rt for 1 h. A catalytic amount of DMAP (2 mg) was added and stirring continued at rt for two hours. Reaction mixture was poured into ice water and extracted with DCM, washed with water, dried and evaporated. Product was purified with flash-chromatography giving 42 mg of product 24.

$^1$H-NMR (DMSO-$d_6$): 0.98 (t, 3H), 1.20-2.40 (m, 16H), 2.86 (m, 2H), 2.90 (s, 3H), 3.02 (s, 3H), 6.82 (s, 1H), 6.84 (d, 1H), 7.12 (s, 1H), 7.26 (dd, 1H), 11.92 (s, 1H). MS m/z (TOF ES$^+$): 574 (M+Na).

Compound 25

Dimethyl-carbamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta-falphenanthren-3-yl ester

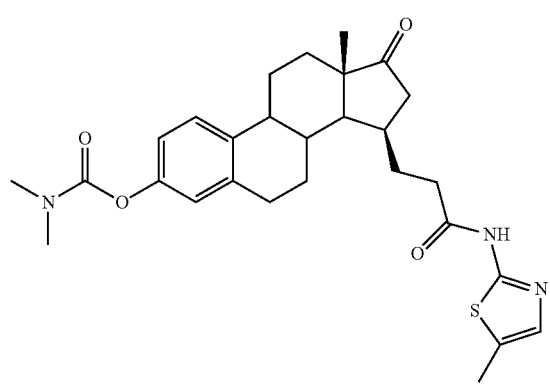 [SMILES: Cc1cnc(NC(=O)CC[C@@H]2CC(=O)[C@@]3(C)CCC4c5ccc(OC(=O)N(C)C)cc5CCC4C23)s1]

The compound 25 was synthesized according to the method used for 24 using N,N-dimethylcarbamoyl chloride as a reagent.

$^1$H-NMR (DMSO-$d_6$): 0.98 (t, 3H), 1.20-2.40 (m, 19H), 2.75 (m, 2H), 4.62 (s, 1H), 6.46 (s, 1H), 6.50 (d, 1H), 7.03 (d, 1H), 7.11 (s, 1H). 11.91 (br s, 1H), 12.21 (br s, 1H). MS m/z (TOF ES$^+$): 532 (M+Na).

Compound 26

Dimethylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

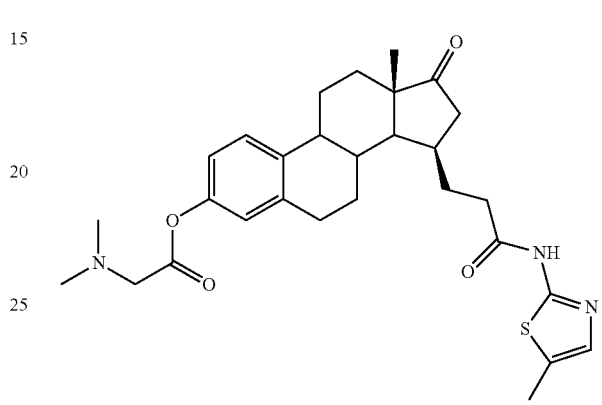

Prepared according to the method used for the compound 15 using N,N-dimethylglycine as a reagent.

$^1$H-NMR (DMSO-$d_6$): 0.98 (s, 3H), 1.40 (m), 1.6-2.4 (m), 2.31 (s, 3H), 2.39 (s, 6H), 2.87 (s, 2H), 6.86 (s, 2H), 7.11 (m, 1H), 7.30 (d, 1H), 11.92 (5, 1H). MS m/z (TOF ES$^+$): 524 (M+1).

Compound 27

Toluene-4-sulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester

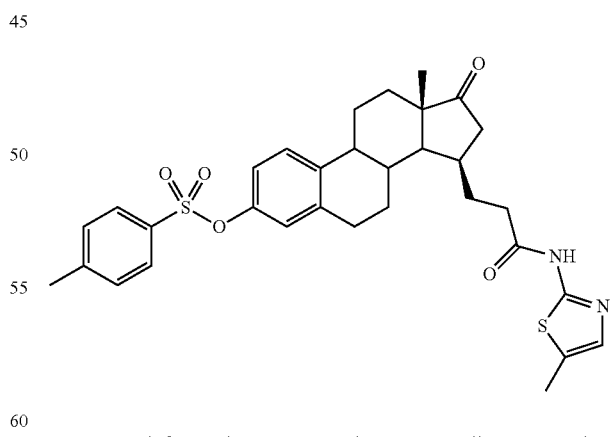

Prepared from the compound VII according to method used for the compound 23 using p-toluenesulfonyl chloride as a reagent.

$^1$H-NMR (DMSO-$d_6$): 0.95 (s, 3H), 1.36 (m), 1.6-2.4 (m), 2.32 (s, 3H), 2.42 (s, 3H), 2.81 (s, 2H), 6.72 (m, 2H), 7.10 (m, 1H), 7.25 (d, 1H), 7.48 (d, 2H), 7.75 (d, 2H), 11.91 (s, 1H). MS m/z (TOF ES+): 593 (M+1).

C-3 Glucuronidation
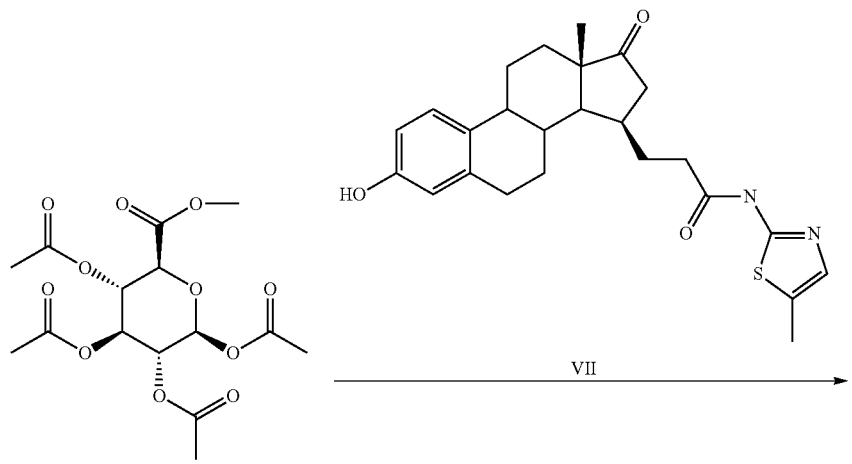
Tetra-acetylated glucuronic acid
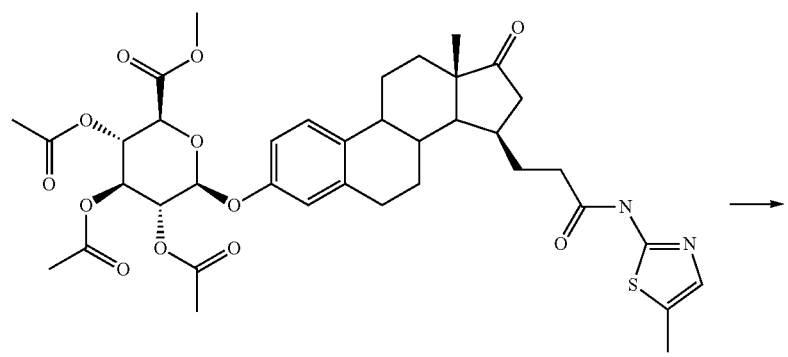
28
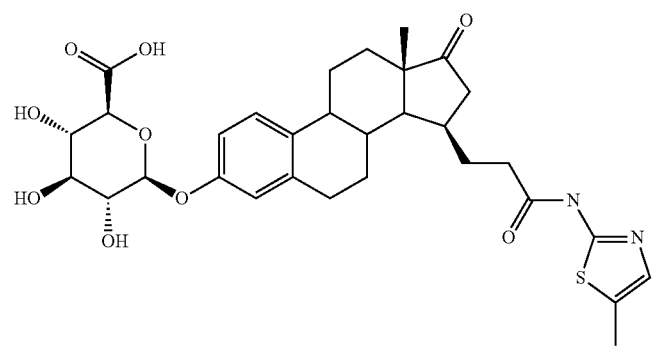
29

Compound 28

(2S,3S,4S,5R,6S)-2-(methoxycarbonyl)-6-(((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl)oxy)tetrahydro-2H-pyran-3,4,5-triyl triacetate

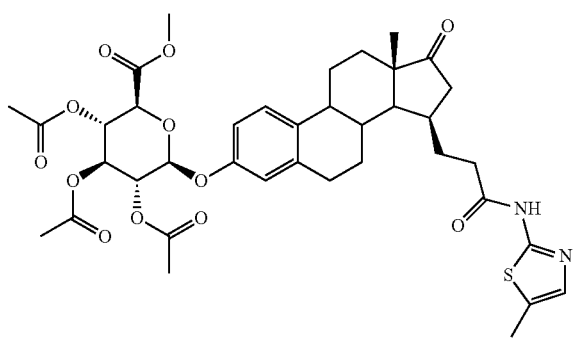 [SMILES: COC(=O)[C@H]1O[C@@H](Oc2ccc3c(c2)CCC2C3CC[C@]3(C)C(=O)C[C@@H](CCC(=O)Nc4ncc(C)s4)C23)[C@H](OC(C)=O)[C@@H](OC(C)=O)[C@@H]1OC(C)=O]

Activation of the Glucuronic Acid:
Tetra-acetylated methylglucuronide was dissolved in dry THF (dry conditions, $N_2$-atmosphere). Morpholine (150 mol-%) was added. After stirring overnight, almost all starting material was reacted. Additional amount of morpholine was added. The product was obtained in 74% yield, used in the preparation of activated glycoside. The 1-O-deacetylated intermediate was dissolved in DCM. Trichloroacetonitrile (800 ul) and 1,8-diazabicyclo[5.4.0]undec-7-ene (DBU) (120 mol-%) were added. Stirring for two hours at rt afforded the crude product, which was purified by chromatography. The yield of the activated glucuronic acid was 98%.

The compound VII (100 mol-%) and protected, activated glucuronic acid (300 mg, 150 mol-%) were stirred in dry DCM with molecular sieves (4 Å) for 30 minutes. Boron trifluoride etherate (400 mol-%) was added to the cooled mixture and stirred at rt for 2.5 hours. A few drops of TEA was added, molecular sieves were filtered. The reaction mixture was diluted with DCM, which was washed several times with water and brine.

$^1$H-NMR (CDCl$_3$): 1.05 (s, 3H), 1.25-2.4 (m), 2.05 (s, 6H), 2.07 (s, 3H), 2.42 (s, 3H), 2.91 (m, 2H), 3.75 (s, 3H), 4.20 (d, 1H), 5.2-5.34 (m, 4H), 6.76 (m, 2H), 7.05 (s, 1H), 7.19 (d, 1H).

Compound 29

(2S,3S,4S,5R,6S)-3,4,5-trihydroxy-6-(((13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl)oxy)tetrahydro-2H-pyran-2-carboxylic acid

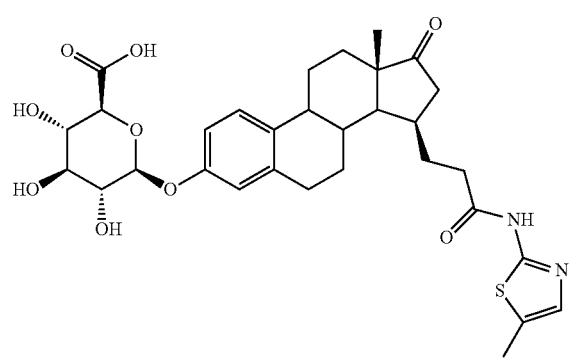 [SMILES: Cc1cnc(NC(=O)CC[C@@H]2CC(=O)[C@@]3(C)CCC4c5ccc(O[C@@H]6O[C@H](C(=O)O)[C@@H](O)[C@H](O)[C@H]6O)cc5CCC4C23)s1]

The acetylated compound 28 HM-5411 B I (400 mg) was stirred at rt for two hours with NaOH (400 mol-%) in methanol (1 ml). Water was added and extracted with EtOAc. The water phase neutralized with dilute HCl-solution. The product was extracted with EtOAc. Organic phases were evaporated.

$^1$H-NMR (CDCl$_3$+DMSO-d$_6$): 1.05 (s, 3H), 1.25-2.4 (m), 2.38 (s, 3H), 2.90 (m, 2H), 3.51-3.92 (m, 4H), 4.89 (d, 1H), 6.84 (m, 2H), 7.04 (s, 1H), 7.17 (d, 1H). MS m/z (TOF ES+): 615 (M+1).

Compound 30

3-((13S,15R)-3-Benzyloxy-13-methyl-17-oxo-7,8,9,11,12,13,14,15,16,17-decahydro-6H-cyclopenta[a]phenanthren-15-yl)-N-(5-methylthiazol-2-yl)propanamide

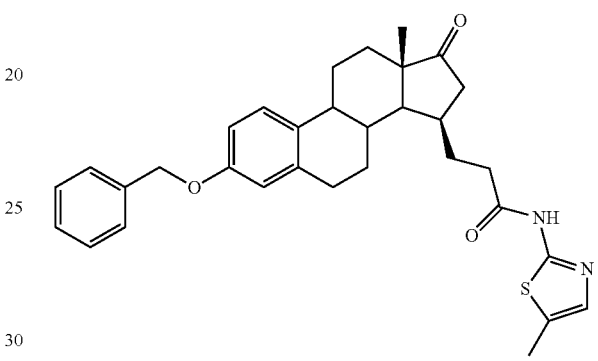

The compound V (2.0 g, 100 mol-%) was dissolved in DCM (80 ml). 2-Amino-5-methylthiazol (200 mol-%), NMM (300 mol-%) and HOBT (170 mol-%) were added to the reaction mixture and stirred for five minutes. The reaction mixture was cooled to 0-5° C. EDCI (220 mol-%) was added and stirred at rt overnight. The reaction mixture was diluted with DCM, washed several times with 1N HCl-solution and brine, and finally with 5% KOH-solution. The organic phase was washed with water and brine. The product 30 was triturated with ethanol-water (8:2).

$^1$H-NMR (DMSO-d$_6$): 0.97 (s, 3H), 1.37-2.50 (m, 19H), 2.85 (m, 2H), 5.06 (s, 2H), 6.74 (m, 2H), 7.11 (d, 1H), 7.16 (d, 1H), 11.92 (s, 1H). MS m/z (TOF ES$^+$): 551 (M+Na).

C-2 and C-4 Modification

Compound 31

3-((13S,15R)-2-(tert-butyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

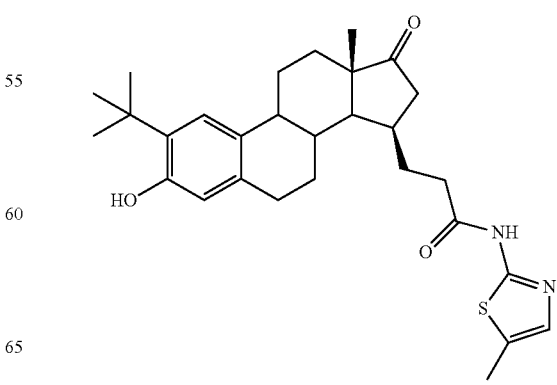

To a stirred suspension of the compound VII (2.0 g, 100 mol-%) in dry dichloromethane, tert-butanol (1.5 ml) and boron trifluoride diethyl etherate (3.2 ml) were added with a syringe at rt and the reaction was followed by TLC. The mixture was stirred overnight at rt and additional amount of boron trifluoride diethyl etherate (1 ml) and tert-butanol (500 µl) were added. The resulting orange solution was stirred for 3 hours before water (40 ml) and DCM (40 ml) were added carefully. The layers were separated and the aqueous layer was extracted with DCM (3×30 ml). The combined organic layers were washed with water (3×30 ml), saturated aqueous NaHCO$_3$ (30 ml) and brine (3×30 ml). The solvents were evaporated and the precipitate was washed with heptane affording 1.8 g of the product 31 (yield 80%).

$^1$H-NMR (DMSO-d$_6$): 0.97 (s, 3H), 1.2-1.45 (m, 12H), 1.5-2.4 (m, 16H), 2.6-2.95 (m, 2H), 6.47 (s, 1H), 7.01 (s, 1H), 7.11 (s, 1H), 8.97 (s, 1H), 11.92 (s, 1H, —NH); MS m/z (TOF ES+): 517 (M+Na)

Compound 32

3-((13S,15R)-3-hydroxy-2-isopropyl-13-methyl-17-oxo-7,8,9,11,12,13,14,15,16,17-decahydro-6H-cyclopenta[a]phenanthren-15-yl)-N-(5-methylthiazol-2-yl)propanamide

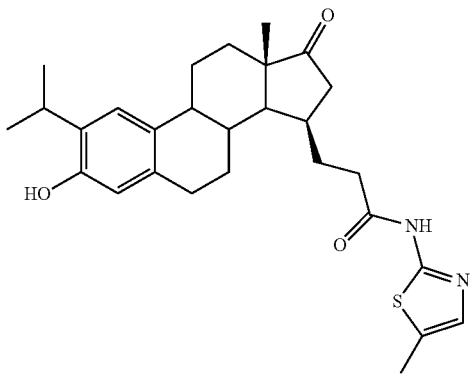

Prepared from the compound VII according to method used for the compound 31 using isopropanol as a reagent.

$^1$H-NMR (CDCl$_3$): 1.05 (s, 3H), 1.31 (s, 3H), 1.34 (s, 3H), 1.4-2.6 (m, 16H), 4.5 (m, 1H), 6.67 (m, 2H), 7.04 (s, 1H), 7.17 (d, 1H), 11.92 (s, 1H); MS m/z (TOF ES+): 481 (M+1)

Compound 33

3-((13S,15R)-2-acetyl-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

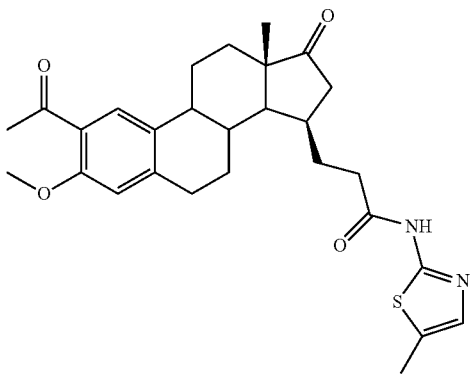 [SMILES: COc1cc2c(cc1C(C)=O)C1CC[C@]3(C)C(=O)C[C@@H](CCC(=O)Nc4ncc(C)s4)C3C1CC2]

Acetyl chloride (34 mg, 195 mol-%) was added dropwise to a cooled (0° C.) suspension of AlCl$_3$ (59 mg, 200 mol-%) in DCM (1 ml). To this was added dropwise a solution of the compound X (100 mg, 100 mol-%) in DCM (1 ml). The reaction mixture was stirred 2 h at 0° C. and let to stir overnight at rt. The additional suspension of AlCl$_3$ (63 mg, 210 mol-%) and acetyl chloride (32 mg, 190 mol-%) in DCM (1 ml) was added to the reaction. Ice-cold water (5 ml) and DCM (10 ml) were added to the reaction mixture and it was stirred 10 min. The layers were separated and aqueous layer was extracted with DCM (2×10 ml). The combined organic layers were washed with water (15 ml) and brine (15 ml), dried with Na$_2$SO$_4$ and the solvents were evaporated. The crude product was purified by column chromatography. Yield: 75 mg (69%).

$^1$H-NMR (CDCl$_3$): 1.05 (s, 3H), 1.36-2.68 (m, 22H), 2.90-3.03 (m, 2H), 3.89 (s, 3H), 6.69 (s, 1H), 7.05 (s, 1H), 7.69 (s, 1H), 11.76 (br, 1H); MS m/z (TOF ES+): 495 (M+1).

Nitration of VII and Further Modifications

The reaction vessel was charged with the compound VII (1.32 g, 3 mmol) and ethanol (45 ml) under nitrogen atmosphere. THF (30 ml) and ferric nitrate (600 mg, 1.5 mmol) were added. After stirring the reaction mixture for 4 h at 60° C., the solvents were evaporated. HPLC of the crude reaction mixture showed 45% of 2-nitro-isomer 34 and 35% of 4-nitroisomer 35. Purification by flash chromatography gave 358 mg of pure 34 and 284 mg of pure 35. In addition, the product mixture contained ca. 5% of 2,4-dinitro derivative 36.

Compound 34

3-((13S,15R)-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

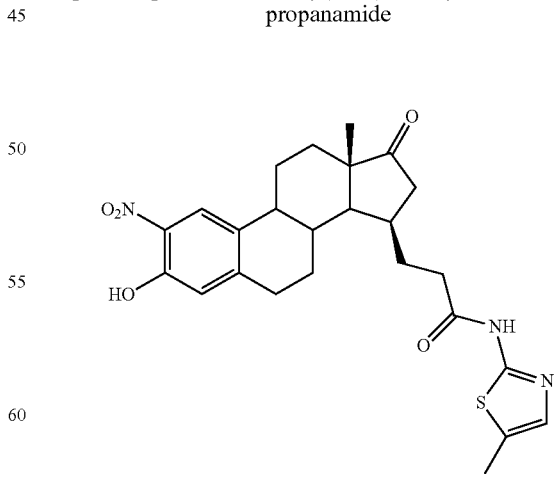

$^1$H-NMR (CDCl$_3$): 1.07 (s, 3H), 1.30-2.75 (m, 19H), 2.9-3.05 (m, 2H), 6.89 (s, 1H), 7.05 (s, 1H), 7.98 (s, 1H). MS m/z (TOF ES$^+$): 506 (M+Na)

Compound 35

3-((13S,15R)-3-hydroxy-13-methyl-4-nitro-17-oxo-7,8,9,11,12,13,14,15,16,17-decahydro-6H-cyclopenta[a]phenanthren-15-yl)-N-(5-methylthiazol-2-yl)propanamide

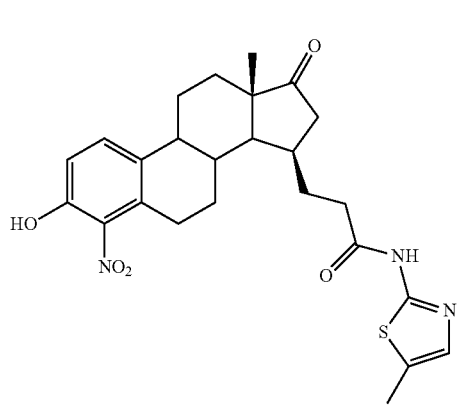

$^1$H-NMR (CDCl$_3$): 1.08 (s, 3H), 1.3-3.4 (m, 21H), 6.96 (d, 1H), 7.05 (s, 1H), 7.45 (d, 1H). MS m/z (TOF ES$^+$): 506 (M+Na)

Compound 36

3-((13S,15R)-3-hydroxy-13-methyl-2,4-dinitro-17-oxo-7,8,9,11,12,13,14,15,16,17-decahydro-6H-cyclopenta[a]phenanthren-15-yl)-N-(5-methylthiazol-2-yl)propanamide

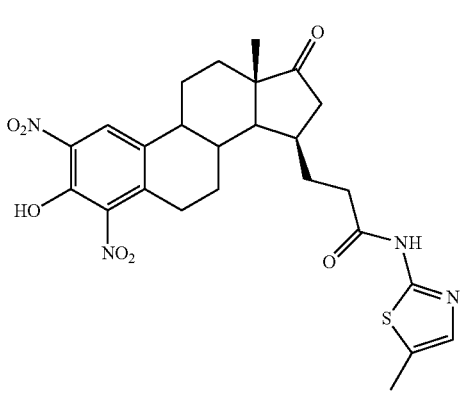 [SMILES: Cc1cnc(NC(=O)CC[C@@H]2CC(=O)[C@@]3(C)CCC4c5cc([N+](=O)[O-])c(O)c([N+](=O)[O-])c5CCC4C23)s1]

$^1$H-NMR (CDCl$_3$): 1.08 (s, 3H), 1.35-3.10 (m, 21H), 7.03 (s, 1H), 8.14 (s, 1H). MS m/z (TOF ES$^+$): 529 (M+H)

Aminoderivatives

Compound 37

3-((13S,15R)-2-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

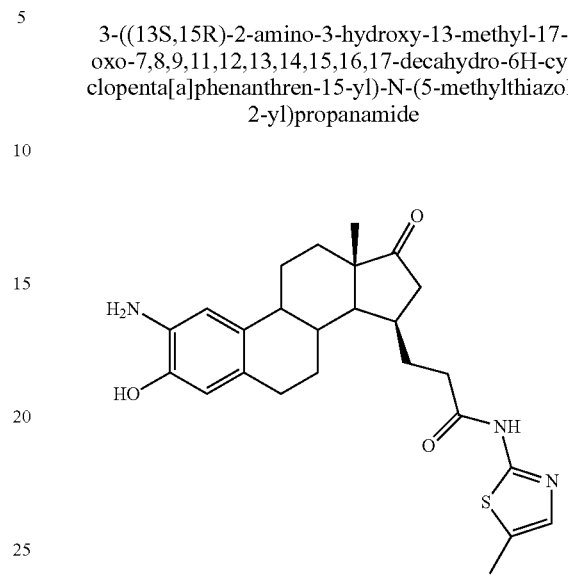

Hydrogenation of the compound 34 was carried out at atmospheric pressure at rt in ethanol/THF 1:1 using 10% Pd/C as catalyst. Catalyst was filtered off, solvents were evaporated and product purified by flash chromatography if needed.

$^1$H-NMR (CDCl$_3$+MeOH-d$_4$): 1.06 (s, 3H), 1.30-2.65 (m, 19H), 2.80-2.95 (m, 2H), 6.50 (s, 1H), 6.69 (s, 1H), 7.03 (s, 1H). MS m/z (TOF ES$^+$): 454 (M+H)

Compound 38

3-((13S,15R)-4-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

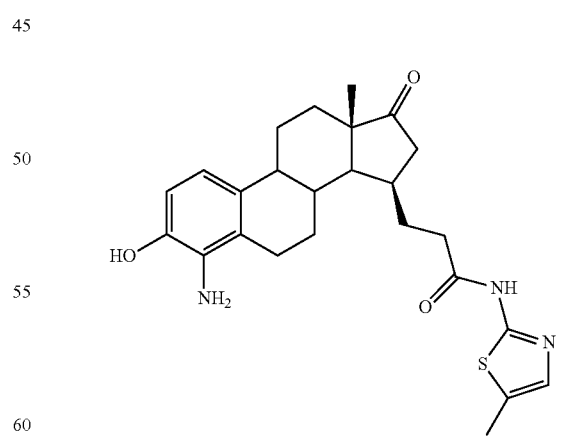

Prepared according to method used for the compound 37 using the compound 35 as a starting material.

$^1$H-NMR (CDCl$_3$+MeOH-d$_4$): 1.03 (s, 3H), 1.35-2.65 (m, 19H), 2.75-3.00 (m, 2H), 6.63 (s, 2H), 7.03 (s, 1H). MS m/z (TOF ES$^+$): 476 (M+Na).

Compound 39

(13S,15R)-13-methyl-15-(3-((5-methylthiazol-2-yl)amino)-3-oxopropyl)-4-nitro-17-oxo-7,8,9,11,12,13,14,15,16,17-decahydro-6H-cyclopentafalphenanthren-3-yl methanesulfonate

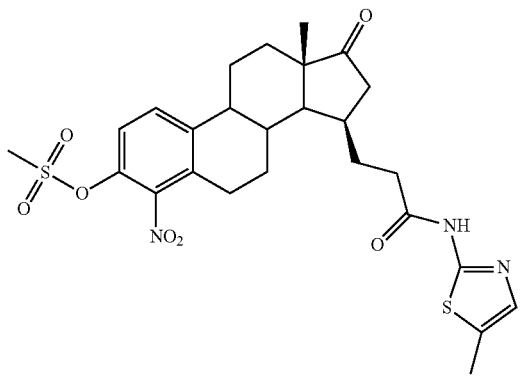 [SMILES: Cc1cnc(NC(=O)CC[C@@H]2CC(=O)[C@@]3(C)CCC4c5ccc(OS(C)(=O)=O)c([N+](=O)[O-])c5CCC4C23)s1]

Prepared from the compound 35 with methanesulfonic anhydride in DCM using TEA as a base at room temperature.

$^1$H-NMR (CDCl$_3$): 1.03 (s, 3H), 1.35-3.00 (m, 21H), 3.17 (s, 3H), 7.00 (s, 1H), 7.40 (AB, 2H), 11.25 (br s). MS m/z (TOF ES+): 584 (M+Na).

Compound 40

(13S,15R)-4-amino-13-methyl-15-(3-((5-methylthiazol-2-yl)amino)-3-oxopropyl)-17-oxo-7,8,9,11,12,13,14,15,16,17-decahydro-6H-cyclopentafalphenanthren-3-yl methanesulfonate

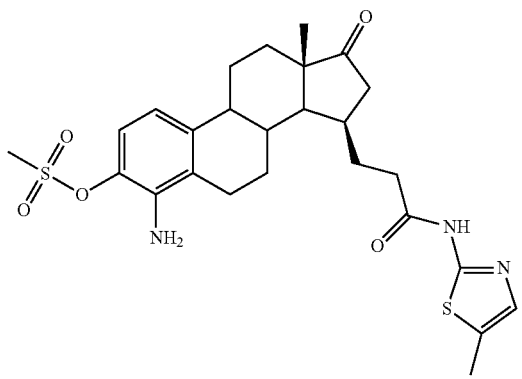

Prepared from the compound 39 (1 mmol) by reduction with 10% excess of Zn and ammonium chloride (300 mol-%) in 50 ml of methanol and 15 ml of THF. The reaction mixture was refluxed for 2.5 hours, and filtered through Celite with washing carefully with methanol. The product was purified by chromatography using 3% MeOH in DCM as an eluent.

$^1$H-NMR (CDCl$_3$): 1.01 (s, 3H), 1.35-2.90 (m, 19H), 3.18 (s, 3H), 6.72 (d, 1H), 7.05 (d, 1H), 7.06 (s, 1H), 12.37 (br s, 1H). MS m/z (TOF ES+): 554 (M+Na).

Compound 41

3-((13S,15R)-3-hydroxy-13-methyl-17-oxo-4-(2,2,2-trifluoroacetamido)-7,8,9,11,12,13,14,15,16,17-decahydro-6H-cyclopenta[a]phenanthren-15-yl)-N-(5-methylthiazol-2-yl)propanamide

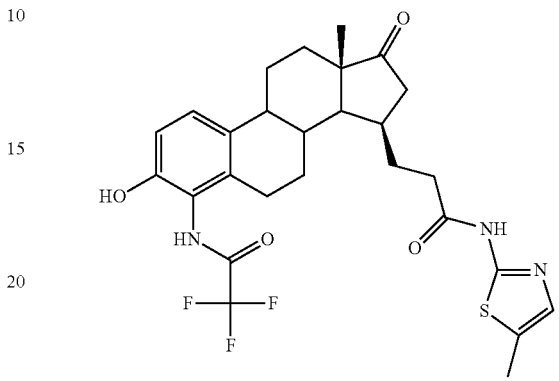

Prepared from the compound 38 with trifluoroacetic anhydride in DCM using TEA as a base at room temperature.

$^1$H-NMR (CDCl$_3$): 1.04 (s, 3H), 1.35-2.85 (m, 21H), 6.88 (d, 1H), 7.10 (s, 1H), 7.23 (d, 1H), 7.85 (s, 2H). MS m/z (TOF ES+): 550 (M+H).

General Method for Mann Ich Reaction (Aminomethylation) of Phenols

Phenol (0.1-0.2 mmol scale) in ethanol-THF (v/v 3:2) was heated with excess of amine and formalin until TLC showed formation of a new reaction product. New compounds were purified by preparative TLC.

Compound 42

3-((13S,15R)-3-hydroxy-13-methyl-2-(morpholinomethyl)-17-oxo-7,8,9,11,12,13,14,15,16,17-decahydro-6H-cyclopenta[a]phenanthren-15-yl)-N-(5-methylthiazol-2-yl)propanamide

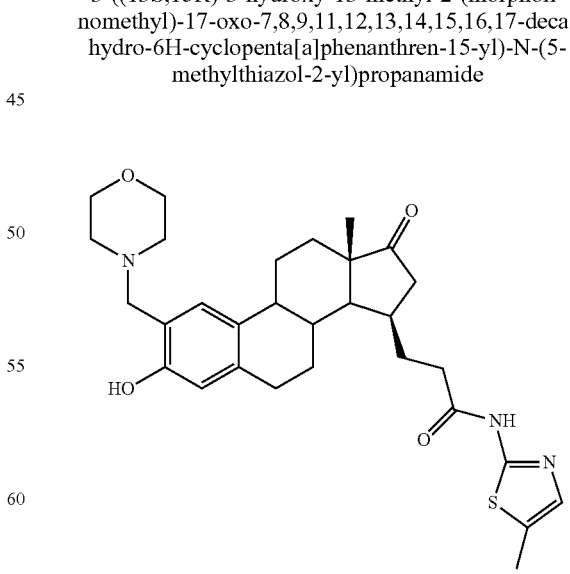

Prepared from the compound VII by the aminomethylation method described above using morpholine as an amine.

¹H-NMR (CDCl₃): 1.05 (s, 3H), 1.30-3.00 (m, 21H), 3.60-3.85 (m, 6H), 6.59 (s, 1H), 6.88 (s, 1H), 7.04 (s, 1H), 11.87 (br s, 1H). MS m/z (TOF ES+): 538 (M+H).

Compound 43

3-((13S,15R)-3-hydroxy-13-methyl-2-(morpholinomethyl)-4-nitro-17-oxo-7,8,9,11,12,13,14,15,16,17-decahydro-6H-cyclopenta[a]phenanthren-15-yl)-N-(5-methylthiazol-2-yl)propanamide

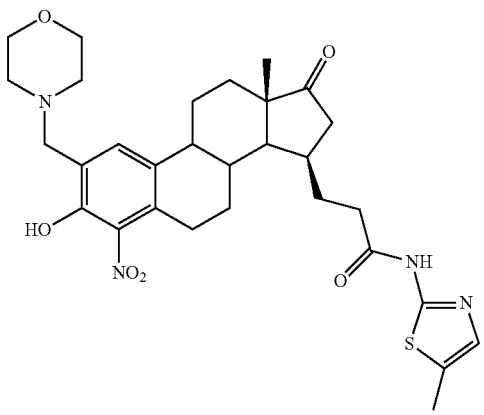 [SMILES: Cc1cnc(NC(=O)CC[C@@H]2CC(=O)[C@@]3(C)CCC4c5cc(CN6CCOCC6)c(O)c([N+](=O)[O-])c5CCC4C23)s1]

Prepared from the compound 35 by the aminomethylation method described above using morpholine as an amine.

¹H-NMR (CDCl₃): 1.06 (s, 3H), 1.30-3.00 (m, 21H), 3.65-3.85 (m, 6H), 7.02 (s, 1H), 7.04 (s, 1H), 11.58 (br s, 1H). MS m/z (TOF ES+): 583 (M+H).

Compound 44

3-((13S,15R)-2-(((dimethylamino)methyl)-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

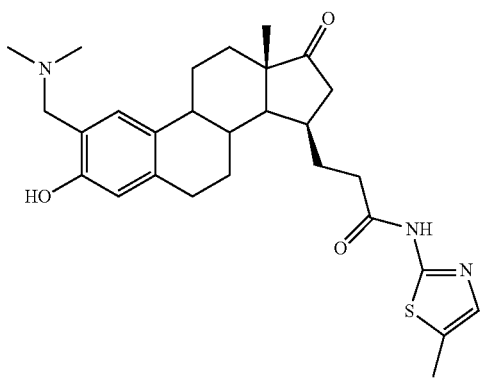 [SMILES: Cc1cnc(NC(=O)CC[C@@H]2CC(=O)[C@@]3(C)CCC4c5cc(CN(C)C)c(O)cc5CCC4C23)s1]

Prepared from the compound VII by the aminomethylation method described above using dimethylamine hydrochloride as an amine.

¹H-NMR (CDCl₃): 1.06 (s, 3H), 1.30-3.00 (m, 21H), 3.59 (AB, 2H), 6.58 (s, 1H), 6.85 (s, 1H), 7.05 (s, 1H), 11.50 (br s, 1H). MS m/z (TOF ES+): 496 (M+H).

Compound 45

3-((13S,15R)-3-hydroxy-13-methyl-17-oxo-2-(pyrrolidin-1-ylmethyl)-7,8,9,11,12,13,14,15,16,17-decahydro-6H-cyclopenta[a]phenanthren-15-yl)-N-(5-methylthiazol-2-yl)propanamide

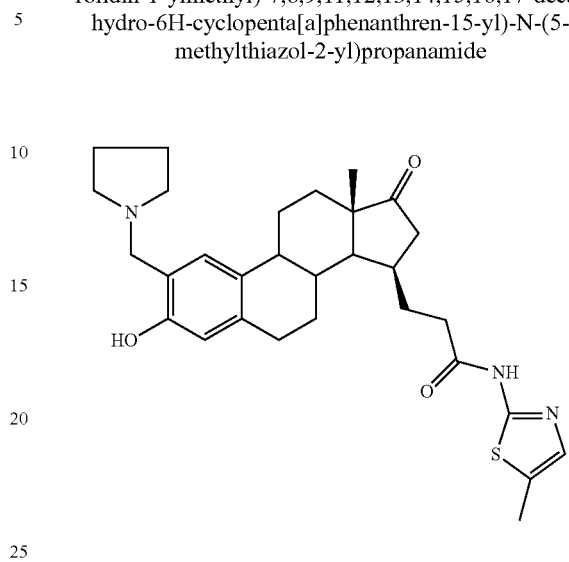

Prepared from the compound VII by the aminomethylation method described above using pyrrolidine as an amine.

¹H-NMR (CDCl₃): 1.06 (s, 3H), 1.30-3.00 (m, 21H), 3.78 (AB, 2H), 6.57 (s, 1H), 6.88 (s, 1H), 7.05 (s, 1H), 12.00 (br s, 1H). MS m/z (TOF ES+): 522 (M+H).

Heterocyclic 2,3- and 3,4-Modifications

Compound 46

3-((7aS,10R)-7a-methyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide

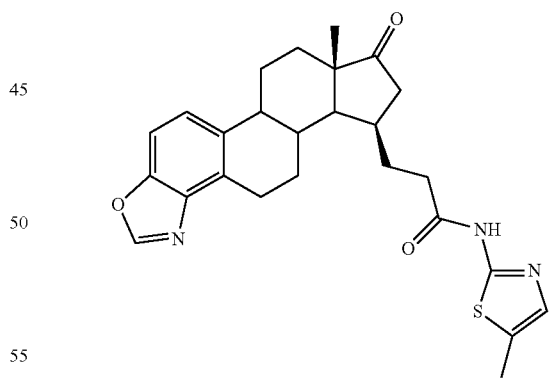

110 mg of the compound 38 was added under nitrogen atmosphere into a mixture of 1.5 ml trimethylortoformate and 1.5 ml of THF. Catalytic amount of p-toluenesulfonic acid was added and the mixture was stirred at rt until TLC showed starting material having disappeared. The mixture was evaporated and purified with flash chromatography giving 76 mg (68%) of the benzoxazole 46.

¹H-NMR (CDCl₃): 1.09 (s, 3H), 1.40-2.80 (m, 19H), 3.05-3.50 (m, 2H), 7.06 (s, 1H), 7.37 (s, 2H), 8.06 (s, 1H), 12.43 (s, 1H). MS m/z (TOF ES⁺): 486 (M+Na)

Compound 47

3-((3R,12aS)-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

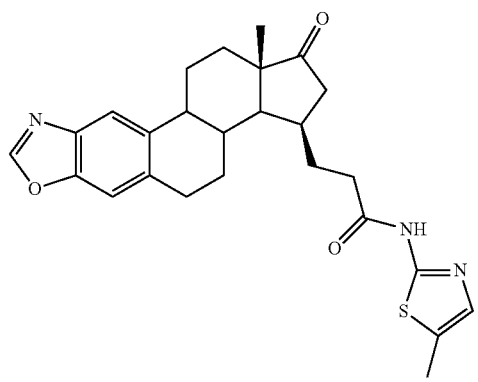 [SMILES: Cc1cnc(NC(=O)CC[C@@H]2CC(=O)[C@@]3(C)CCC4c5cc6ncoc6cc5CCC4C23)s1]

Prepared by the same method as the compound 46 using the compound 37 as starting material.

$^1$H-NMR (CDCl$_3$): 1.07 (s, 3H), 1.30-2.75 (m, 18H), 2.95-3.15 (m, 3H), 7.05 (s, 1H), 7.32 (s, 1H), 7.70 (s, 1H), 8.01 (s, 1H), 12.31 (s, 1H). MS m/z (TOF ES$^+$): 486 (M+Na)

Compound 48

3-((3R,12aS)-8,12a-dimethyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

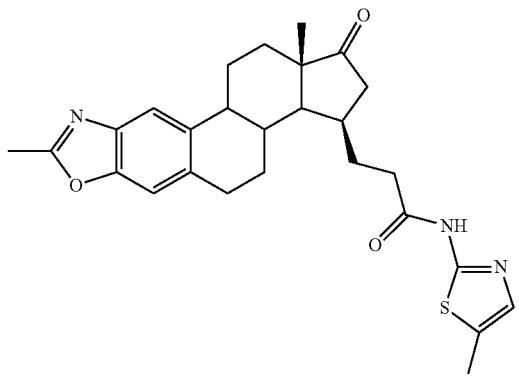 [SMILES: Cc1nc2cc3c(cc2o1)CCC1C3CC[C@]2(C)C(=O)C[C@@H](CCC(=O)Nc3ncc(C)s3)C12]

Prepared by the same method as the compound 46 using the compound 37 as starting material and trimethylortoacetate instead of trimethylortoformate as reagent.

$^1$H-NMR (CDCl$_3$): 1.07 (s, 3H), 1.35-2.75 (m, 22H), 2.90-3.10 (m, 2H), 7.05 (s, 1H), 7.19 (s, 1H), 7.55 (s, 1H), 12.22 (s, 1H). MS m/z (TOF ES$^+$): 478 (M+H)

Compound 49

3-((7aS,10R)-2,7a-dimethyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide

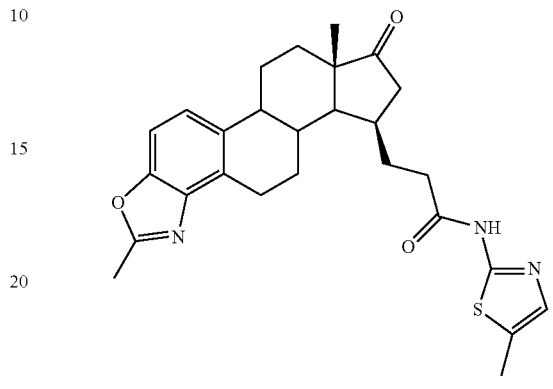

The compound 38 (100 mg) was dissolved in dry acetonitrile. Borontrifluoride dietherate (150 mol-%) was added and the reaction was started to refluxed. t-Butylnitrite (240 mol-%) was added slowly dropwise to the THF solution. The reaction was completed in two hours. Water was added to the reaction mixture followed by evaporation of the solvents. The crude product was purified by chromatography.

$^1$H-NMR (DMSO-d$_6$): 0.99 (s, 3H), 1.23-3.16 (m, 24H), 7.12-7.41 (m, 2H), 11.93 (s, 1H). MS m/z (TOF ES+): 500 (M+Na).

Compound 50

3-((3R,12aS)-12a-methyl-1,8-dioxo-2,3,3a,3b,4,5,8,9,10b,11,12,12a-dodecahydro-1H-cyclopenta[7,8]phenanthro[3,2-d]oxazol-3-yl)-N-(5-methylthiazol-2-yl)propanamide

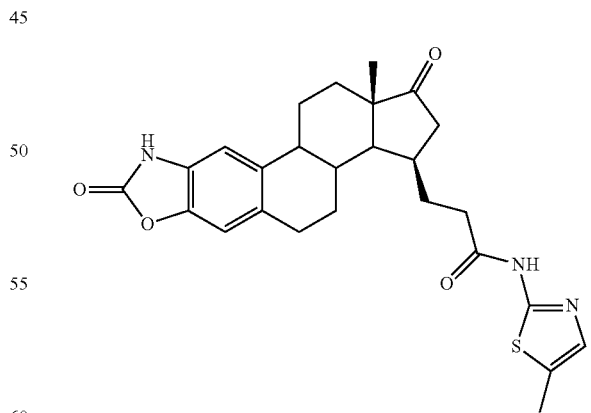

Into 23 mg (0.05 mmol) of the compound 37 in 0.3 ml of THF was added 10 mg of carbonyldiimidazole and the mixture was stirred under nitrogen at 60° C. for 7 h. Then dil. HCl was added and the product was extracted with EtOAc and purified with flash chromatography giving 12 mg of product 50.

¹H-NMR (CDCl₃): 1.06 (s, 3H), 1.35-2.75 (m, 19H), 2.80-3.00 (m, 2H), 6.91 (s 1H), 6.98 (s, 1H), 7.10 (s, 1H), 10.67 (br s, 1H), 11.93 (br s, 1H). MS m/z (TOF ES⁺): 502 (M+Na).

Compound 51

3-((7aS,10R)-7a-methyl-2,8-dioxo-2,5b,6,7,7a,8,9, 10,10a,10b,11,12-dodecahydro-1H-cyclopenta[7,8] phenanthro[1,2-d]oxazol-10-yl)-N-(5-methylthiazol-2-yl)propanamide

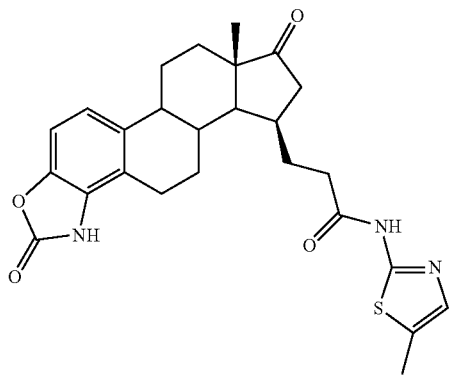 [SMILES: Cc1cnc(NC(=O)CC[C@@H]2CC(=O)[C@@]3(C)CCC4c5ccc6oc(=O)[nH]c6c5CCC4C23)s1]

The compound 51 was prepared by the same method as for the compound 50 using the compound 38 as a starting material ¹H-NMR (DMSO-d₆): 0.97 (s, 3H), 1.25-2.95 (m, 21H), 7.00-7.20 (m, 3H), 11.68 (br s, 1H), 11.93 (s, 1H). MS m/z (TOF ES+): 502 (M+Na).

Halogenation of the Aromatic Ring

Compound 52

3-((13S,15R)-2-iodo-3-methoxy-13-methyl-17-oxo-7,8,9,11,12,13,14,15,16,17-decahydro-6H-cyclo-penta[a]phenanthren-15-yl)-N-(5-methylthiazol-2-yl) propanamide

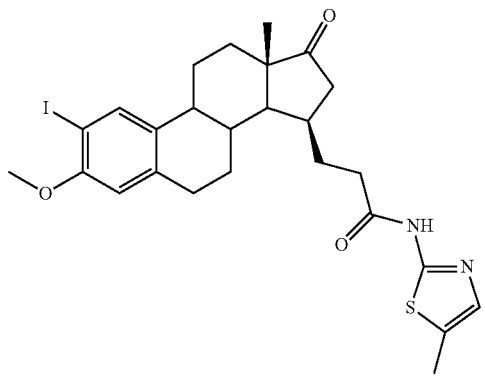 [SMILES: COc1cc2c(cc1I)C1CC[C@]3(C)C(=O)C[C@@H](CCC(=O)Nc4ncc(C)s4)C3C1CC2]

The compound X (100 mg, 100 mo-%) was dissolved in dry DCM (4 ml). Iodine, CF₃COOAg (73 mg, 150 mol-%) and NaHCO₃ (124 mg, 670 mol-%) were added and the reaction mixture was stirred for three hours at −30° C. The reaction mixture was filtered and the solid material was washed with DCM. The filtrate was evaporated followed by co-evaporation with toluene and heptane. The solid product was washed with heptane. The yield of the product 52 was 100 mg (78%).

¹H-NMR (CDCl₃): 1.06 (s, 3H, –Me), 1.20-3.00 (m, 21H), 3.85 (s, 3H), 6.56 (s, 1H), 7.11 (s, 1H), 7.64 (s, 1H). MS m/z (TOF ES+): 579 (M+1).

Compound 53

3-((13S,15R)-3-hydroxy-2,4-diiodo-13-methyl-17-oxo-7,8,9,11,12,13,14,15,16,17-decahydro-6H-cy-clopenta[a]phenanthren-15-yl)-N-(5-methylthiazol-2-yl)propanamide

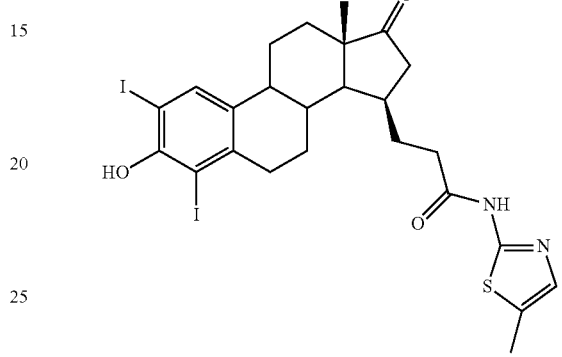

The compound VII (44 mg, 0.1 mmol) was dissolved into DCM and mixture was stirred in ice bath. 45 mg (0.2 mmol) of N-iodosuccinimide was added and reaction mixture was stirred for 10 min at 0° C. and then reaction was allowed to warm to rt. After 20 min water was added and the precipitated product was filtered, washed with water and finally with heptane. Trituration with DCM gave 40% of pure di-iododerivative 53.

MS m/z (TOF ES⁺): 691 (M+1), 713 (M+Na).

Compound 54

3-((13S,15R)-3-hydroxy-4-iodo-13-methyl-17-oxo-7,8,9,11,12,13,14,15,16,17-decahydro-6H-cyclo-penta[a]phenanthren-15-yl)-N-(5-methylthiazol-2-yl) propanamide

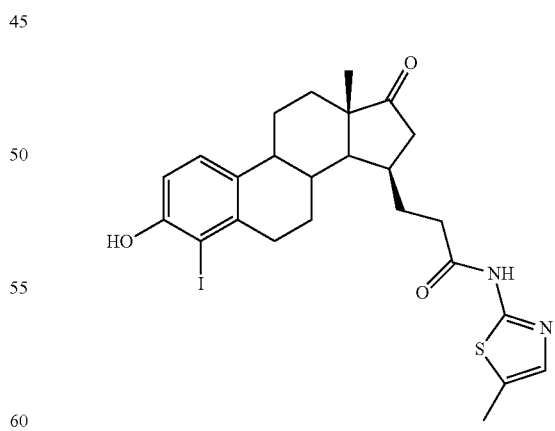

The compound 38 (23 mg, 0.05 mmol) was dissolved into a mixture of 0.5 ml of THF and 0.5 ml of 2N HCl and the solution chilled to 0° C. An ice-cold solution of NaNO₂ (5 mg) was added and stirring continued 15 min. Then 30 mg of KI in 50 ul of water was added and the reaction mixture was stirred at 80° C. for 1 h. Water was added into cooled reaction mixture and product was extracted with ethyl acetate, organic phases were washed with water and dried. After evaporation the product was purified by preparative TLC giving 7 mg of pure 54.

¹H-NMR (CDCl₃): 1.04 (s, 3H), 1.30-2.95 (m, 21H), 6.84 (d, 1H), 7.06 (s, 1H), 7.19 (d, 1H). MS m/z (TOF ES⁺): 565 (M+H)

Compound 55

3-((13S,15R)-3-hydroxy-2-iodo-13-methyl-17-oxo-7,8,9,11,12,13,14,15,16,17-decahydro-6H-cyclopenta[a]phenanthren-15-yl)-N-(5-methylthiazol-2-yl)propanamide

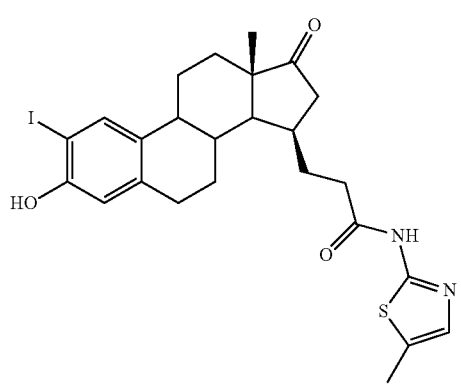 [SMILES: Cc1cnc(NC(=O)CC[C@@H]2CC(=O)[C@@]3(C)CCC4c5cc(I)c(O)cc5CCC4C23)s1]

Prepared using the same method as for the compound 54 using the compound 37 as a starting material.

¹H-NMR (CDCl₃): 1.05 (s, 3H), 1.28-2.75 (m, 19H), 2.75-2.90 (m, 2H), 6.74 (s, 1H), 7.05 (s, 1H), 7.51 (s, 1H). MS m/z (TOF ES⁺): 587 (M+Na)

Compounds 56 and 57

The reaction vessel was charged with VII (2.97 g) in DCM (140 ml) and methanol (20 ml). This solution was added dropwise to the solution of tetrabutylammonium tribromide in DCM/MeOH (v/v 1:1, 10 ml) during 30 minutes by stirring at 0-5° C. After 60 minutes the HPLC analysis showed the formation of three products with traces of unreacted starting material; 41% of the monobromide 56, 38% of the monobromide 57 and 16% of the dibromide 58.

Compound 56

3-((13S,15R)-2-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

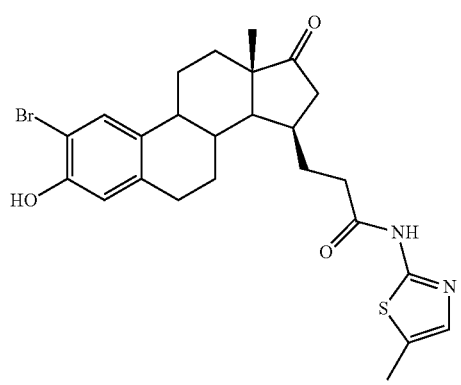

¹H-NMR (DMSO-d₆): 0.96 (s, 3H, –Me), 1.35-2.40 (m, 21H), 2.75 (m, 2H), 6.67 (s, 1H), 7.11 (s, 1H), 7.27 (s, 1H), 9.89 (s, 1H), 11.92 (s, 1H).

Compound 57

3-((13S,15R)-4-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

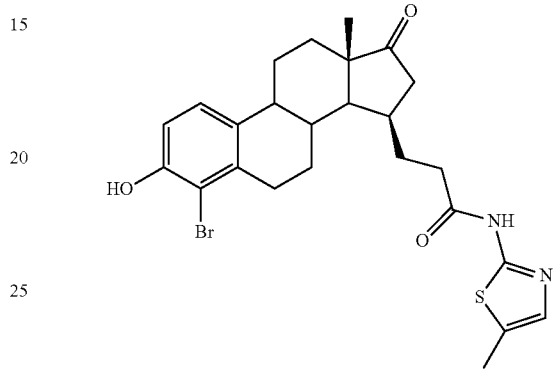

¹H-NMR (DMSO-d₆): 0.95 (s, 3H, –Me), 1.35-2.40 (m, 21H), 2.83 (m, 2H), 6.78 (d, 1H), 7.11 (m, 2H), 7.27 (s, 1H), 9.89 (s, 1H), 11.92 (s, 1H).

Compound 58

3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

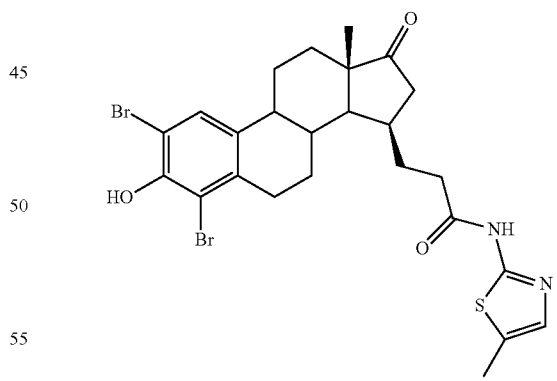

The compound VII (1.0 g, 2.3 mmol) was dissolved in DCM (13 ml), the mixture was cooled to 8° C. and N-bromosuccinimide (NBS) (1.0 g, 5.6 mmol) was added. Reaction mixture was let to warm to rt and stirring was continued for 2.5 h. Water was added and precipitated product was filtered, yielding 1.2 g of crystalline material.

¹H-NMR (DMSO-d₆): 0.95 (s, 3H), 1.22-2.32 (m, 19H), 2.79 (m, 2H), 7.12 (s, 1H), 7.40 (s, 1H), 9.55 (s, 1H), 11.92 (s, 1H). MS m/z (TOF ES⁺): 617/619/621 (M+Na).

Compound 59

N-(5-methylthiazol-2-yl)-3-((13S,15S)-2,4,16-tribromo-3-hydroxy-13-methyl-17-oxo-7,8,9,11,12,13,14,15,16,17-decahydro-6H-cyclopenta[a]phenanthren-15-yl)propanamide

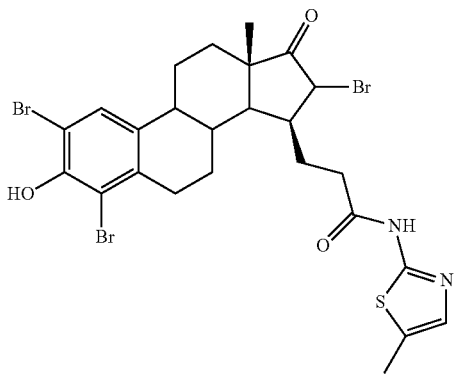 [SMILES: Cc1cnc(NC(=O)CC[C@@H]2C(Br)C(=O)[C@@]3(C)CCC4c5cc(Br)c(O)c(Br)c5CCC4C23)s1]

Isolated as a tribrominated by-product in the preparation of the compound 58.

$^1$H-NMR (CDCl$_3$): 1.10 (s, 3H), 1.35-3.10 (m, 21H), 4.55 (d, 1H), 7.15 (s, 1H), 7.38 (s, 1H). MS m/z (TOF ES$^+$): 695/697/699/701 (M+Na).

Compounds 60, 61 and 62

The compound X (0.3 g) was dissolved in dry DMSO (0.5 ml). Bromine (370 μl) in DCM (0.1 ml) was added to the reaction mixture and stirred overnight at rt. Water (5 ml) was added followed by stirring for one hour. The product was extracted with EtOAc. The organic phases were washed with water trice, and finally with brine. Purified by flash chromatography using DCM:EtOAc 10:1 as an eluent. Three bromide derivatives 60, 61, 62 were isolated.

Compound 60

N-(5-methylthiazol-2-yl)-3-((13S,15S)-2,4,16-tribromo-3-methoxy-13-methyl-17-oxo-7,8,9,11,12,13,14,15,16,17-decahydro-6H-cyclopenta[a]phenanthren-15-yl)propanamide

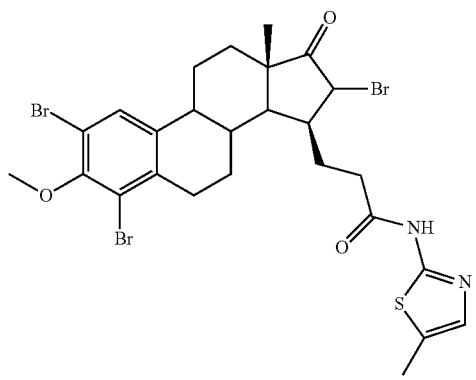 [SMILES: COc1c(Br)cc2c(c1Br)CCC1C2CC[C@]2(C)C(=O)C(Br)[C@@H](CCC(=O)Nc3ncc(C)s3)C12]

$^1$H-NMR (CDCl$_3$): 1.14 (s, 3H), 1.25-2.99 (m, 19H), 3.87 (s, 3H), 5.03 (s, 1H), 6.64 (s, 1H), 7.41 (s, 1H). MS m/z (TOF ES$^+$): 709/711/713/715 (M+Na).

Compound 61

3-((13S,15S)-2,16-dibromo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

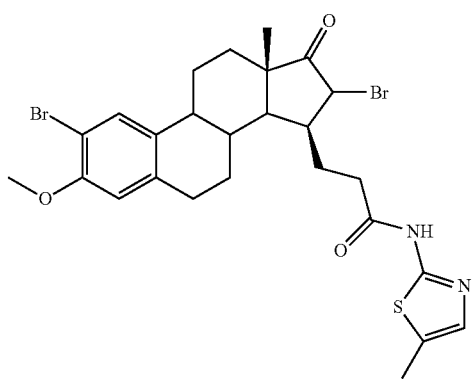 [SMILES: COc1cc2c(cc1Br)C1CC[C@]3(C)C(=O)C(Br)[C@@H](CCC(=O)Nc4ncc(C)s4)C3C1CC2]

$^1$H-NMR (CDCl$_3$): 1.12 (s, 3H), 1.3-2.99 (m, 19H), 3.87 (s, 3H), 4.48 (d, 1H), 5.03 (s, 1H), 6.64 (s, 1H), 7.20 (m, 1H), 7.42 (s, 1H). MS m/z (TOF ES$^+$): 631/633/635 (M+Na).

Compound 62

3-((13S,15S)-16-bromo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

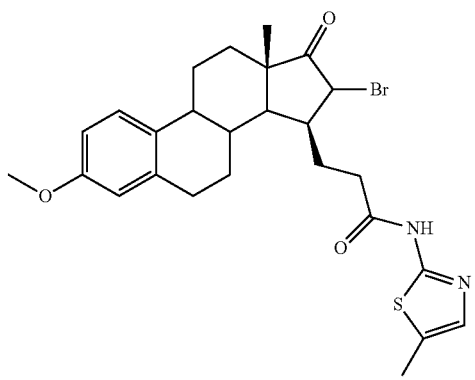 [SMILES: COc1ccc2c(c1)CCC1C2CC[C@]2(C)C(=O)C(Br)[C@@H](CCC(=O)Nc3ncc(C)s3)C12]

$^1$H-NMR (DMSO-d$_6$): 1.05 (s, 3H), 1.25-2.90 (m, 19H), 3.69 (s, 3H), 5.03 (s, 1H), 6.68 (m, 2H), 7.12 (s, 1H), 11.95 (s, 1H). MS m/z (TOF ES$^+$): 531/533

Compound 63

3-((13S,15R)-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

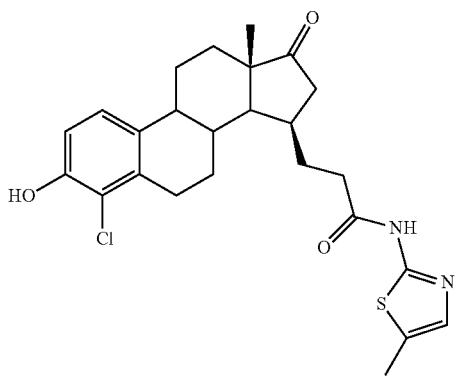

0.5 mmol of the amine 38 in 3 ml 2N HCl and 1 ml THF was chilled stirring at 0° C. Solution of 50 mg of NaNO$_2$ in 0.5 ml of water was added dropwise and mixture was stirred for 15 min at this temperature. Then ice bath was removed and preheated solution of 250 mg of CuCl in 5 ml of 2N HCl was added at 80° C. and reaction mixture was kept 2 h at this temperature. After cooling water was added, pH was adjusted to pH 3 and extracted with ethyl acetate, washed with water and brine, dried with Na$_2$SO$_4$ and evaporated. After flash chromatography 85 mg (36%) of the 4-chloro compound 63 was obtained.

$^1$H-NMR (CDCl$_3$): 1.05 (s, 3H), 1.30-3.10 (m, 21H), 6.86 (d, 1H), 7.05 (s, 1H), 7.13 (d, 1H). MS m/z (TOF ES$^+$): 473/475 (M+H).

Compound 64

3-((13S,15R)-2-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

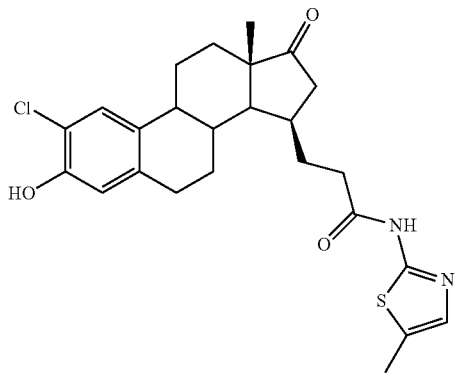

Prepared from the compound 37 in 0.4 mmol scale giving the desired product in 28% yield.

$^1$H-NMR (CDCl$_3$+MeOH-d$_4$): 1.06 (s, 3H), 1.20-2.65 (m, 19H), 2.75-3.05 (m, 2H), 6.70 (s, 1H), 7.03 (s, 1H), 7.18 (s, 1H). MS m/z (TOF ES+): 495/497 (M+Na).

Compound 65

3-((13S,15R)-2,4-dichloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

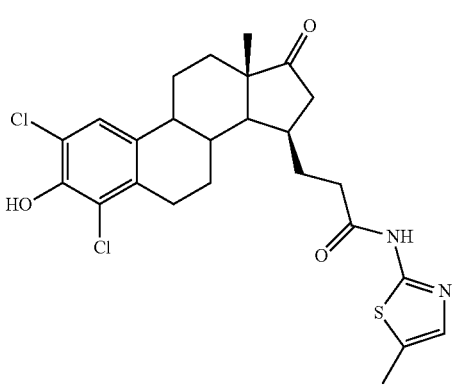 [SMILES: Cc1cnc(NC(=O)CC[C@@H]2CC(=O)[C@@]3(C)CCC4c5cc(Cl)c(O)c(Cl)c5CCC4C23)s1]

The reaction vessel was charged with the compound VII (4 g) and dry DCM (150 ml) at 0° C. under argon atmosphere. Diethylamine (1.4 ml, 150 mol-%) was added dropwise, followed by sulfuryl chloride (1.1 ml, 150 mol-%). After 30 minutes at 0° C. water was added to the reaction mixture. The organic phase was separated, dried over Na$_2$SO$_4$ and the solvent was evaporated. The residue was purified by column chromatography using DCM/acetone 98:2 as an eluent.

$^1$H-NMR (DMSO-d$_6$): 0.96 (s, 3H), 1.35-2.40 (m, 21H), 2.80 (m, 2H), 7.12 (s, 1H), 7.23 (s, 1H), 9.75 (s, 1H), 11.92 (s, 1H).

Fluorination Method I

Fluorides were prepared from the corresponding amines via thermolysis of their diazonium fluoroborate salts in 0.05-0.3 mmol scale, the compound 66 as an example:

A mixture of the compound 38 (91 mg, 0.2 mmol), ethanol (2 ml) and 48% tetrafluoroboric acid (0.5 ml) in water was chilled to 0° C. stirring in ice bath. A solution of NaNO$_2$ (20 mg) in 0.2 ml of water was added and stirring continued for 1 h at 0° C. Fluoroborate salt was precipitated by adding diethyl ether until there was no more salt coming out the solution. Ether was decanted and precipitated material was washed twice with diethyl ether and dried in vacuum without warming. The dried fluoroborate salt was heated in a flask at 120-130° C. in a good hood for a couple of hours. The remaining material was treated with DCM and filtered. The solvent was evaporated and the product was purified by flash chromatography giving 22 mg (24%) of the fluoride 66.

Compound 66

3-((13S,15R)-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

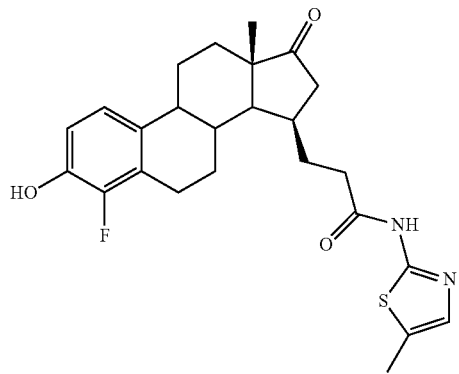

$^1$H-NMR (CDCl$_3$): 1.04 (s, 3H), 1.30-3.05 (m, 21H), 6.75-6.98 (m, 2H), 7.05 (br s, 1H). MS m/z (TOF ES+): 479 (M+Na).

Compound 67

3-((13S,15R)-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

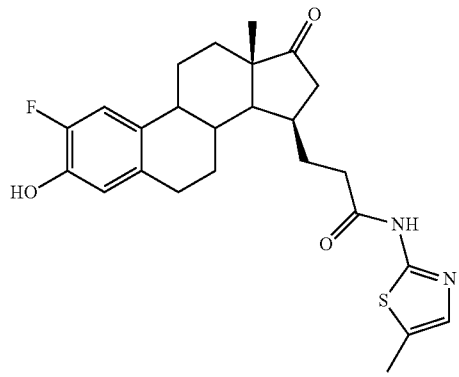

Prepared from the compound 37 using the method used for the compound 66. The catechol 68 was isolated as a by-product.

$^1$H-NMR (CDCl$_3$): 1.05 (s, 3H), 1.30-2.70 (m, 19H), 2.75-2.90 (m, 2H), 6.73 (d, J=10 Hz, 1H), 6.97 (d, J=14 Hz, 1H), 7.05 (br s, 1H). MS m/z (TOF ES$^+$): 479 (M+Na).

Compound 68

3-((13S,15R)-2,3-dihydroxy-13-methyl-17-oxo-7,8,9,11,12,13,14,15,16,17-decahydro-6H-cyclopenta[a]phenanthren-15-yl)-N-(5-methylthiazol-2-yl)propanamide

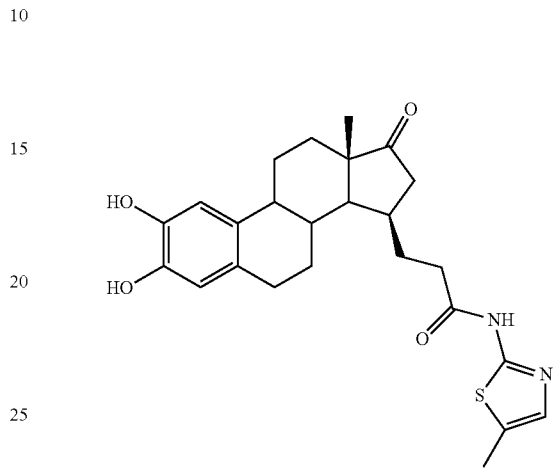

$^1$H-NMR (CDCl$_3$+MeOH-d$_4$): 1.07 (s, 3H), 1.20-2.70 (m, 21H), 7.07 (s, 1H), 7.16 (s, 1H), 7.31 (s, 1H). MS m/z (TOF ES$^+$): 477 (M+Na).

Fluorination Method II:

Compounds 69 and 70

(13S,15R)-2-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate

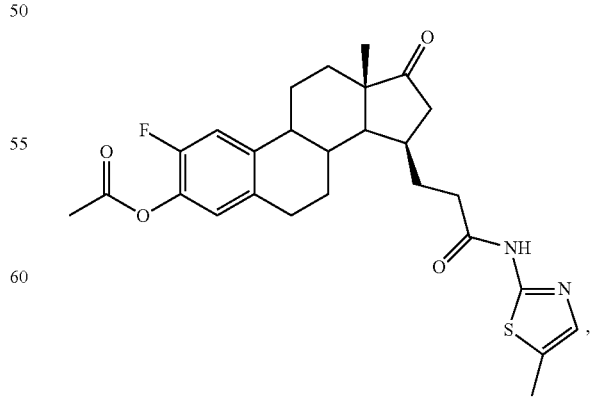

and

117

(13S,15R)-4-fluoro-13-methyl-15-(3-((5-methylthiazol-2-yl)amino)-3-oxopropyl)-17-oxo-7,8,9,11,12,13,14,15,16,17-decahydro-6H-cyclopenta[a]phenanthren-3-yl acetate

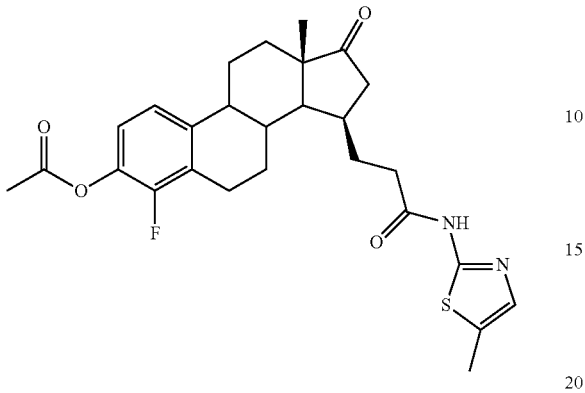

The compound VII (100 mg, 100 mol-%) and 1-fluoropyridinium triflate (225 mg, 400 mol-%) in 1,2-dichloroethane (2.5 ml) was heated at 100° C. for 1 h on microwave instrument. Water (10 ml) was added, and the mixture was extracted with DCM (3×10 ml). The combined organic layers were washed with water (10 ml) and brine (20 ml) and dried over $Na_2SO_4$. The solvents were removed under reduced pressure and residue was purified by column chromatography using DCM-MeOH (10:0 to 9:1) as an eluent. A mixture of 2- and 4-monofluoro derivatives (39 mg) was obtained. Mixture of 2- and 4-monofluoro derivatives: $^1$H-NMR (CDCl$_3$): 1.04 (s, 3H), 1.12-2.90 (m, 21H) 6.59-7.14 (m, 3H); MS m/z (TOF ES$^+$): 457 (M+1).

A mixture of 2- and 4-monofluorides (39 mg, 0.082 mmol) in acetic anhydride (2 ml) and pyridine (2 ml) was stirred at rt overnight. DCM (10 ml) was added to reaction mixture and organic layer was washed with water (5 ml), 1N HCl (3×5 ml) and brine (3×5 ml), dried over $Na_2SO_4$. The solvents were removed under reduced pressure and residue was purified by column chromatography using DCM-MeOH (10:0 to 9:1) as an eluent. Two isomers were obtained as a mixture of 2- and 4-monofluoro compounds 69 and 70 (17 mg, in a ratio 4:1).
$^1$H-NMR (CDCl$_3$): 1.06 (s, 3H) 1.16-2.75 (m, 25H), 2.76-3.0 (m, 2H), 6.83-7.1 (m, 3H); MS m/z (TOF ES$^+$): 499 (M+1).

Compound 71

3-((13S,15R)-2-bromo-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

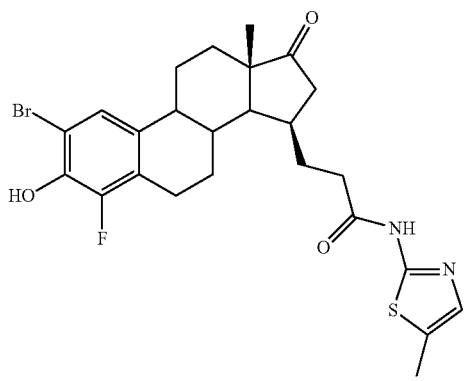 [SMILES: Cc1cnc(NC(=O)CC[C@@H]2CC(=O)[C@@]3(C)CCC4c5cc(Br)c(O)c(F)c5CCC4C23)s1]

The starting material, the compound 66 was brominated by using NBS (120 mol-%) in DCM at 0° C.
$^1$H-NMR (CDCl$_3$): 1.05 (s, 3H), 1.26-2.99 (m, 21H), 7.05 (s, 1H), 7.12 (s, 1H). MS m/z (TOF ES+): 557/559 (M+Na).

Compound 72

3-((13S,15R)-4-bromo-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

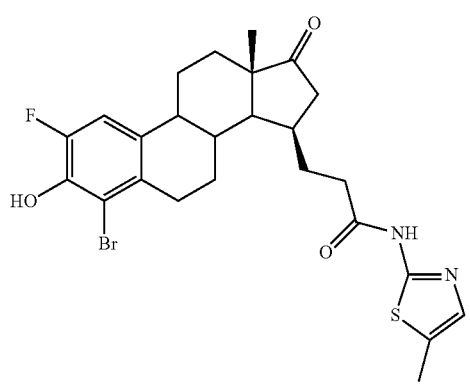 [SMILES: Cc1cnc(NC(=O)CC[C@@H]2CC(=O)[C@@]3(C)CCC4c5cc(F)c(O)c(Br)c5CCC4C23)s1]

The starting material, the compound 67 was brominated by using NBS (120 mol-%) in DCM at 0° C.
$^1$H-NMR (CDCl$_3$): 1.04 (s, 3H), 1.36-2.97 (m, 21H), 6.99 (d, 1H), 7.05 (br s, 1H). MS m/z (TOF ES$^+$): 535/537 (M+H).

Compound 73

3-((13S,15R)-4-fluoro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

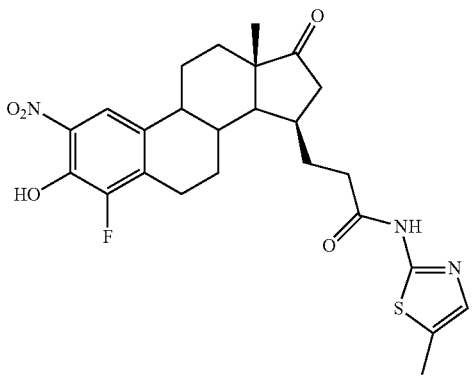 [SMILES: Cc1cnc(NC(=O)CC[C@@H]2CC(=O)[C@@]3(C)CCC4c5cc([N+](=O)[O-])c(O)c(F)c5CCC4C23)s1]

150 mg of the compound 66 was added into a suspension of 55 mg of silica and 55 µl water in a solution of 1.4 ml THF and 1.4 ml DCM and stirred at rt. 340 mg of silica-sulfuric acid (prepared by adding dropwise 8.0 g of sulphuric acid to 10 g of silica gel, and stirred for 30 minutes at rt) was added, followed by 32 mg of sodium nitrite. Stirring was continued at rt and reaction was monitored by TLC and HPLC. After the reaction was completed silica was filtered off, washed with DCM and finally with DCM-methanol. Solvents were evaporated and the product was purified by flash chromatography giving 40 mg of the compound 73.

$^1$H-NMR (CDCl$_3$): 1.07 (s, 3H), 1.30-3.20 (m, 21H), 7.05 (s, 1H), 7.82 (s, 1H). MS m/z (TOF ES+): 502 (M+H).

Compound 74

3-((13S,15R)-2-amino-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

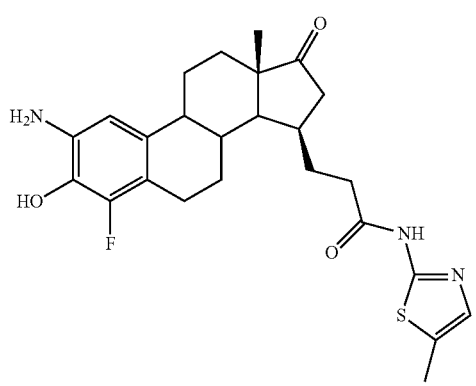

Prepared by hydrogenation of the compound 73 in ethanol containing 20% of THF with Pd/C at 25-30° C.

$^1$H-NMR (CDCl$_3$): 1.06 (s, 3H), 1.30-2.50 (m, 21H), 6.48 (s, 1H), 6.58 (s, 1H). MS m/z (TOF ES+): 494 (M+Na).

Compound 75

3-((13S,15R)-4-chloro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

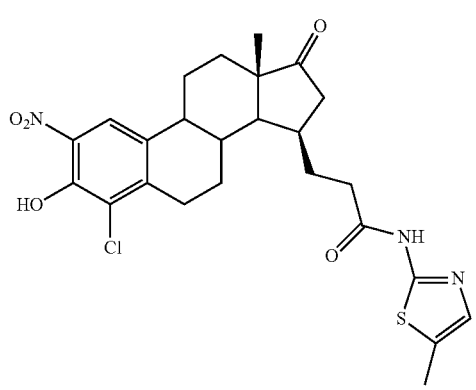 [SMILES: Cc1cnc(NC(=O)CC[C@@H]2CC(=O)[C@@]3(C)CCC4c5cc([N+](=O)[O-])c(O)c(Cl)c5CCC4C23)s1]

Prepared from the compound 63 as described for the compound 73.

$^1$H-NMR (CDCl$_3$): 1.07 (s, 3H), 1.35-3.20 (m, 21H), 7.05 (s, 1H), 7.99 (s, 1H). MS m/z (TOF ES+): 518/520 (M+H).

Compound 76

3-((13S,15R)-2-amino-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

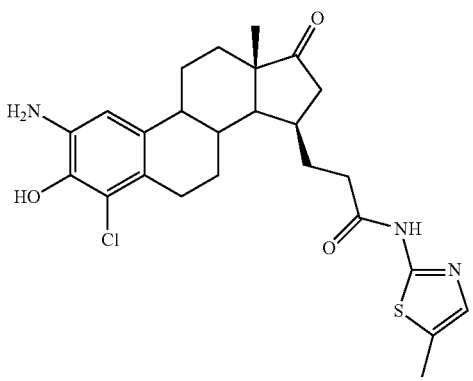

Prepared by hydrogenation of the compound 75 in ethanol containing 20% of THF with Pd/C at 25-30° C.

$^1$H-NMR (CDCl$_3$+MeOH-d$_4$): 1.05 (s, 3H), 1.35-3.00 (m, 21H), 6.64 (s, 1H), 7.04 (s, 1H). MS m/z (TOF ES+): 510/512 (M+Na).

Halogenated Heterocyclic Compounds

Compound 77

3-((3R,12aS)-6-chloro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

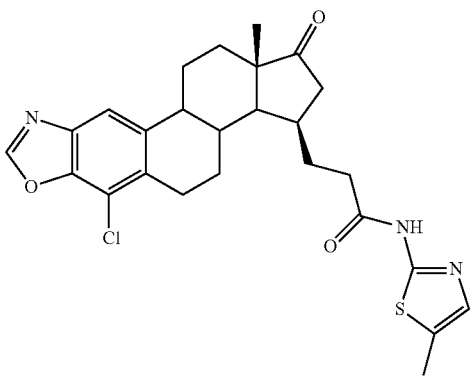 [SMILES: Cc1cnc(NC(=O)CC[C@@H]2CC(=O)[C@@]3(C)CCC4c5cc6ncoc6c(Cl)c5CCC4C23)s1]

The compound 77 was prepared from the compound 76 using trimethylortoformate as reagent as described for the compound 46.

$^1$H-NMR (CDCl$_3$): 1.07 (s, 3H), 1.40-3.45 (m, 21H), 7.06 (s, 1H), 7.66 (s, 1H), 8.06 (s, 1H), 11.89 (br s, 1H). MS m/z (TOF ES+): 498/500 (M+H).

Compound 78

3-((3R,12aS)-6-fluoro-12a-methyl-1-oxo-2,3,3a,3b,
4,5,10b,11,12,12a-decahydro-1H-cyclopenta[7,8]
phenanthro[3,2-d]oxazol-3-yl)-N-(5-methylthiazol-
2-yl)propanamide

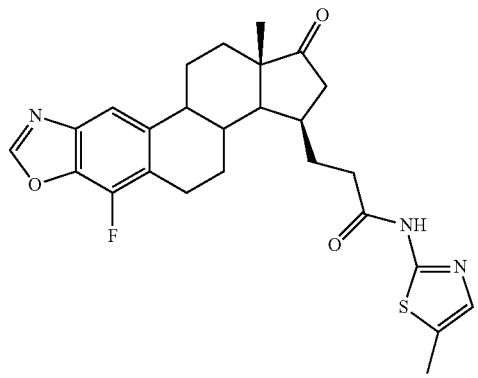 [SMILES: Cc1cnc(NC(=O)CC[C@@H]2CC(=O)[C@@]3(C)CCC4c5cc6ncoc6c(F)c5CCC4C23)s1]

The compound 78 was prepared from the compound 74 with trimethylortoformate, method described for the compound 46.

¹H-NMR (CDCl₃): 1.08 (s, 3H), 1.40-3.20 (m, 21H), 7.05 (s, 1H), 7.52 (s, 1H), 8.03 (s, 1H), 11.91 (br s, 1H). MS m/z (TOF ES+): 482 (M+H).

Synthesis of C3-Deoxo-Derivatives from Triflates
Triflates

Compound 79

(13S,15R)-13-methyl-15-(3-((5-methylthiazol-2-yl)
amino)-3-oxopropyl)-17-oxo-7,8,9,11,12,13,14,15,
16,17-decahydro-6H-cyclopenta[a]phenanthren-3-yl
trifluoromethanesulfonate

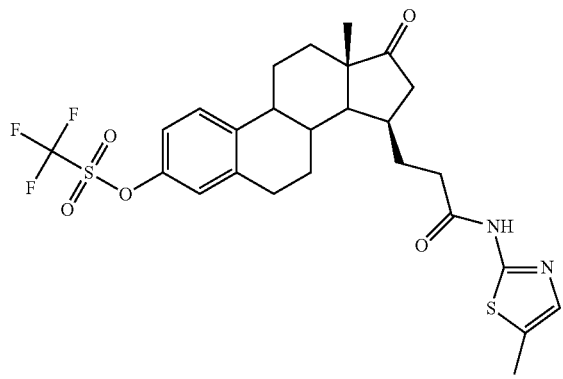 [SMILES: Cc1cnc(NC(=O)CC[C@@H]2CC(=O)[C@@]3(C)CCC4c5ccc(OS(=O)(=O)C(F)(F)F)cc5CCC4C23)s1]

The compound VII (877 mg, 2 mmol) was added into 16 ml of DCM under nitrogen atmosphere. TEA (1.0 g, 1 mmol) was added giving a clear solution. Into this solution at 0° C. was added triflic anhydride (512 µl, 3 mmol). Reaction mixture was then allowed to warm into rt and stirring was continued overnight. Reaction mixture was poured into ice-water. Phases were separated and aqueous phase was extracted twice with DCM. The combined extracts were washed twice with water, dried with Na₂SO₄ and evaporated giving after flash chromatography using DCM-MeOH (85:15) as an eluent 1.00 g (87%) of triflate 79.

¹H-NMR (DMSO-d₆): 0.98 (s, 3H), 1.25-2.50 (m, 19H), 2.85-3.00 (m, 2H), 7.11 (s, 1H), 7.22 (d+s, 2H), 7.46 (d, 1H), 11.91 (s, 1H). MS m/z (TOF ES⁺): 593 (M+Na).

Compound 80

(13S,15R)-13-methyl-15-(3-((5-methylthiazol-2-yl)
amino)-3-oxopropyl)-2-nitro-17-oxo-7,8,9,11,12,13,
14,15,16,17-decahydro-6H-cyclopenta[a]phenan-
thren-3-yl trifluoromethanesulfonate

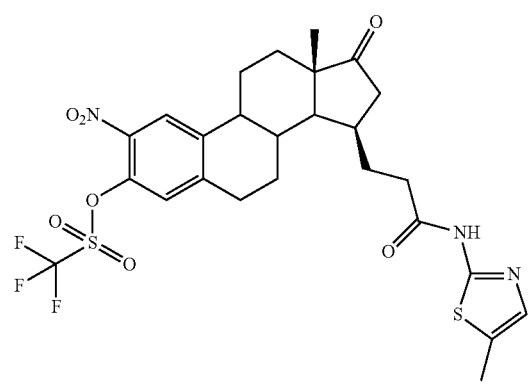 [SMILES: Cc1cnc(NC(=O)CC[C@@H]2CC(=O)[C@@]3(C)CCC4c5cc([N+](=O)[O-])c(OS(=O)(=O)C(F)(F)F)cc5CCC4C23)s1]

The compound 80 was prepared by the same method used for the compound 79. The triflate 80 was used directly to reduction without purification.

Compound 81

(13S,15R)-13-methyl-15-(3-((5-methylthiazol-2-yl)
amino)-3-oxopropyl)-4-nitro-17-oxo-7,8,9,11,12,13,
14,15,16,17-decahydro-6H-cyclopenta[a]phenan-
thren-3-yl trifluoromethanesulfonate

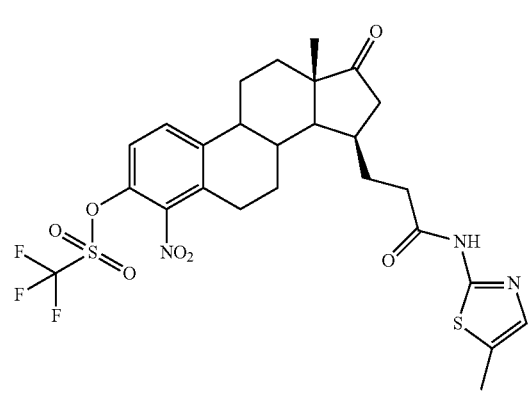 [SMILES: Cc1cnc(NC(=O)CC[C@@H]2CC(=O)[C@@]3(C)CCC4c5ccc(OS(=O)(=O)C(F)(F)F)c([N+](=O)[O-])c5CCC4C23)s1]

The compound 81 was prepared by the same method used for the compound 79. The triflate 81 was used directly to reduction without purification.

Compound 82

(13S,15R)-2-fluoro-13-methyl-15-(3-((5-methylthi-azol-2-yl)amino)-3-oxopropyl)-17-oxo-7,8,9,11,12,13,14,15,16,17-decahydro-6H-cyclopenta[a]phenanthren-3-yl trifluoromethanesulfonate

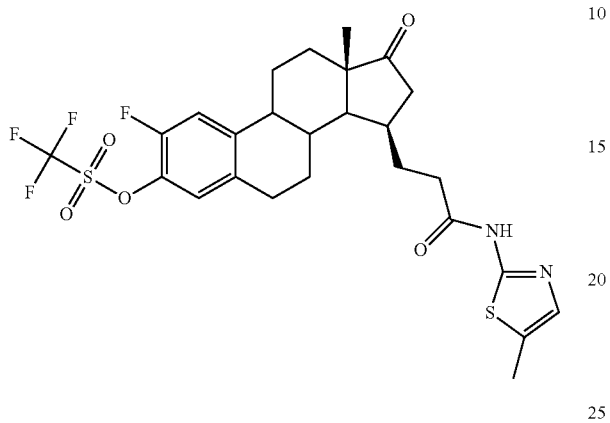

The triflate 72 was prepared by the same method used for the compound 79. The triflate 82 was used directly to reduction without purification.

Deoxo-Compounds

Compound 83

3-((13S,15R)-13-methyl-17-oxo-7,8,9,11,12,13,14,15,16,17-decahydro-6H-cyclopenta[a]phenanthren-15-yl)-N-(5-methylthiazol-2-yl)propanamide

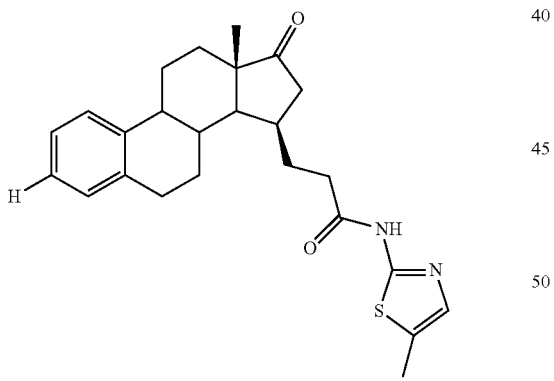

The triflate 79 (257 mg, 0.45 mmol, 100 mol-%), 1,1'-Bis[(diphenylphosphino)ferrocene]dichloropalladium(II) (22 mg, 0.027 mmol, 6 mol-%), TEA (0.19 ml, 1.35 mmol, 300 mol-%) and 4 ml of toluene were charged into reaction vessel. The vessel was closed with a septum and flushed using vacuum/nitrogen, formic acid (33 μl, 0.9 mmol, 200 mol-%) was added and the mixture stirred at 90° C. for 3 h. The reaction mixture was filtered with celite and filtrate was washed several times with toluene. Combined toluene fractions were washed thrice with 1 N HCl and then with water, dried and evaporated giving 178 mg (92%) of raw product, after flash chromatography 133 mg (70%) of pure 83.

$^1$H-NMR (DMSO-$d_6$): 0.98 (s, 3H), 1.25-2.45 (m, 19H), 2.80-2.95 (m, 2H), 7.05-7.15 (m, 4H), 7.20-7.35 (m, 1H), 11.93 (s, 1H). MS m/z (TOF ES$^+$): 445 (M+Na).

Compound 84

3-((13S,15R)-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

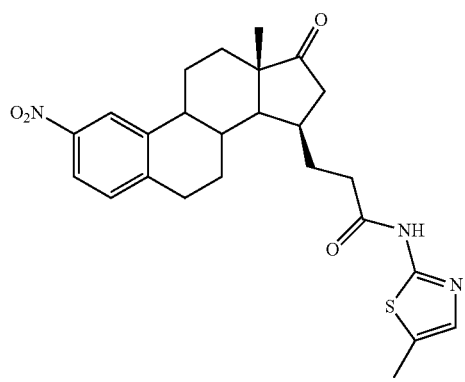 [SMILES: Cc1cnc(NC(=O)CC[C@@H]2CC(=O)[C@@]3(C)CCC4c5cc([N+](=O)[O-])ccc5CCC4C23)s1]

The compound 84 was prepared from the triflate 80 using the method described for the compound 83.

$^1$H-NMR (CDCl$_3$): 1.08 (s, 3H), 1.35-2.70 (m, 19H), 2.95-3.10 (m, 2H), 7.05 (s, 1H), 7.25 (d, 1H), 8.00 (d, 1H), 8.16 (s, 1H), 11.31 (br s, 1H). MS m/z (TOF ES$^+$): 468 (M+H).

Compound 85

3-((13S,15R)-13-methyl-4-nitro-17-oxo-7,8,9,11,12,13,14,15,16,17-decahydro-6H-cyclopenta[a]phenanthren-15-yl)-N-(5-methylthiazol-2-yl)propanamide

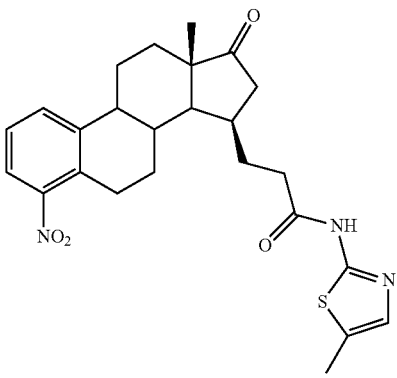 [SMILES: Cc1cnc(NC(=O)CC[C@@H]2CC(=O)[C@@]3(C)CCC4c5cccc([N+](=O)[O-])c5CCC4C23)s1]

The compound 85 was prepared from the triflate 81 using the method described for the compound 83.

$^1$H-NMR (CDCl$_3$): 1.08 (s, 3H), 1.35-3.35 (m, 21H), 7.05 (s, 1H), 7.31 (t, 1H), 7.52 (d, 1H), 7.66 (d, 1H), 12.20 (br s, 1H). MS m/z (TOF ES$^+$): 468 (M+H).

Compound 86

3-((13S,15R)-2-fluoro-13-methyl-17-oxo-7,8,9,11,12,13,14,15,16,17-decahydro-6H-cyclopenta[a]phenanthren-15-yl)-N-(5-methylthiazol-2-yl)propanamide

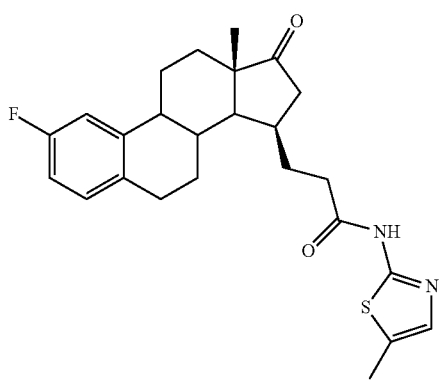 [SMILES: Cc1cnc(NC(=O)CC[C@@H]2CC(=O)[C@@]3(C)CCC4c5cc(F)ccc5CCC4C23)s1]

The compound 86 was prepared from the triflate 82 using the method described for the compound 83.

1H-NMR (CDCl$_3$): 1.06 (s, 3H), 1.30-3.0 (m, 21H), 6.50-7.10 (m, 4H), 6.94 (d, J=12 Hz, 1H), 7.03 (br s, 1H). MS m/z (TOF ES$^+$): 441 (M+H)

Compound 87

3-((13S,15R)-2-amino-13-methyl-17-oxo-7,8,9,11,12,13,14,15,16,17-decahydro-6H-cyclopenta[a]phenanthren-15-yl)-N-(5-methylthiazol-2-yl)propanamide

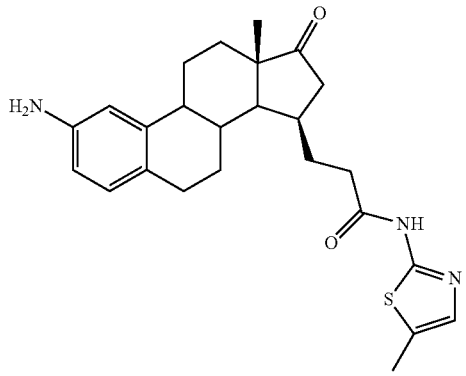 [SMILES: Cc1cnc(NC(=O)CC[C@@H]2CC(=O)[C@@]3(C)CCC4c5cc(N)ccc5CCC4C23)s1]

The compound 87 was prepared from the compound 84 using the method described for the compound 37.

$^1$H-NMR (CDCl$_3$): 1.05 (s, 3H), 1.30-2.90 (m, 19H), 2.70-2.90 (m, 2H), 6.53 (d, 1H), 6.64 (s, 1H), 6.90 (d, 1H), 7.04 (s, 1H) 12.12 (br s, 1H). MS m/z (TOF ES+): 438 (M+H).

Compound 88

3-((13S,15R)-2-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

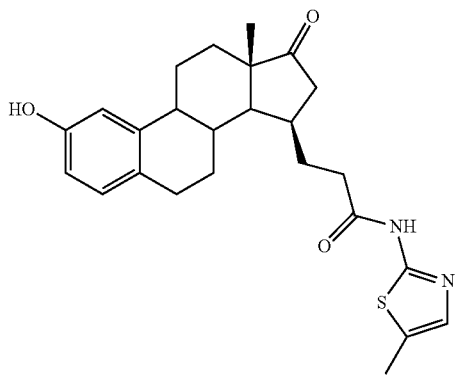 [SMILES: Cc1cnc(NC(=O)CC[C@@H]2CC(=O)[C@@]3(C)CCC4c5cc(O)ccc5CCC4C23)s1]

The starting material 87 (100 mg) in ethanol (3 ml) and HBF$_4$ (48%, 0.5 ml) was cooled with ice-bath. NaNO$_2$-solution was added (150 mol-%) and stirring was continued at ice-bath for 30 minutes. Then sulfamic acid (10 mg, 50 mol-%) was added and the reaction mixture was warmed at 40° C. for two hours. Water and 2N NaOH were added and the product was extracted in DCM. The crude product was purified by flash chromatography using DCM with methanol as a gradient.

$^1$H-NMR (CDCl$_3$): 0.97 (s, 3H), 1.30-2.85 (m, 21H), 6.65 (d, 1H), 6.77 (s, 1H), 6.91 (d, 1H), 7.05 (s, 1H). MS m/z (TOF ES+): 439 (M+H).

Compound 89

3-((13S,15R)-4-amino-13-methyl-17-oxo-7,8,9,11,12,13,14,15,16,17-decahydro-6H-cyclopenta[a]phenanthren-15-yl)-N-(5-methylthiazol-2-yl)propanamide

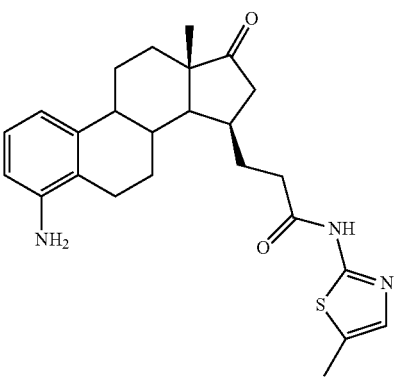 [SMILES: Cc1cnc(NC(=O)CC[C@@H]2CC(=O)[C@@]3(C)CCC4c5cccc(N)c5CCC4C23)s1]

The compound 89 was prepared from the compound 85 using the method described for the compound 37.

$^1$H-NMR (CDCl$_3$+MeOH-d$_4$): 1.05 (s, 3H), 1.35-2.70 (m, 21H), 6.60 (d, 1H), 6.79 (d, 1H), 7.03 (t, 1H), 7.03 (s, 1H). MS m/z (TOF ES+): 438 (M+H).

Compound 90

3-((13S,15R)-4-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

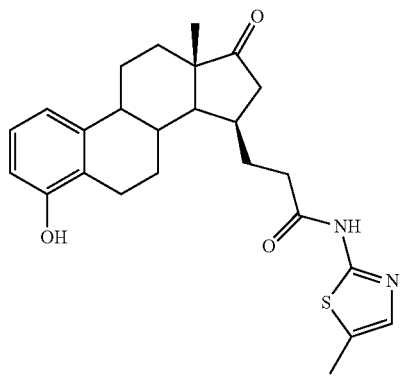 [SMILES: Cc1cnc(NC(=O)CC[C@@H]2CC(=O)[C@@]3(C)CCC4c5cccc(O)c5CCC4C23)s1]

The compound 90 was prepared from the compound 89 using the method described for the compound 88.

$^1$H-NMR (CDCl$_3$+MeOH-d$_4$): 1.05 (s, 3H), 1.30-3.05 (m, 21H), 6.67 (d, 1H), 6.85 (d, 1H), 7.00 (t, 1H), 7.03 (s, 1H). MS m/z (TOF ES+): 439 (M+H).

Compound 91

3-((13S,15R)-2-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

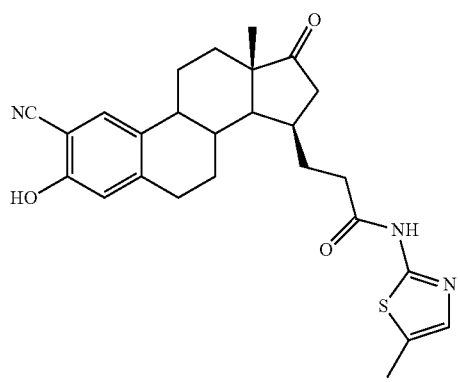

The C-2 bromide 56 (50 mg, 100 mol-%) and copper(I) cyanide (230 mol-%) were dissolved in dry DMF (5 ml) and refluxed under nitrogen for six hours. The reaction mixture was cooled and FeCl$_3$ (5000 mol-%) in conc. HCl (500 µl) was added, and stirred at 55-60° C. for 30 minutes. The reaction mixture was cooled, diluted with water. The product was extracted with EtOAc, washed with water, sat. sodium-bicarbonate solution until pH was 8, and finally with brine. Purification by chromatography.

$^1$H-NMR (CDCl3+MeOH-d$_4$): 1.05 (s, 3H), 1.40-2.65 (m, 19H), 2.89 (m, 2H), 6.70 (s, 1H), 7.06 (s, 1H), 7.36 (s, 1H).

Compound 92

3-((13S,15R)-4-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

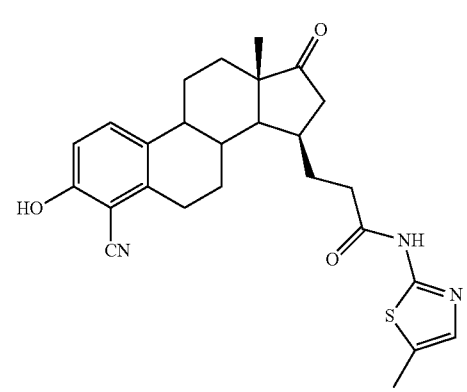

Prepared according to method used for the compound 91 using the C-4 bromide 57 as a starting material.

$^1$H-NMR (CDCl3+MeOH-d$_4$): 1.03 (s, 3H), 1.22-2.56 (m, 19H), 3.05 (m, 2H), 6.76 (d, 1H), 7.06 (s, 1H), 7.31 (s, 1H). MS m/z (TOF ES$^+$): 464 (M+1).

Compound 93

3-((13S,15S)-16-hydroxy-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

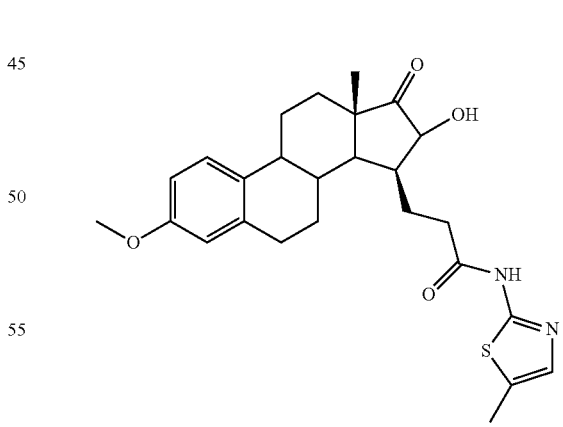

The compound was prepared from the C-16 bromide 62 (100 mg, 100 mol-%) by stirring at rt for 40 minutes with NaOH 150 mol-% in water (0.2 ml) and DMF (2 ml).

$^1$H-NMR (CDCl$_3$): 0.83 (s, 3H), 1.46-2.48 (m, 22H), 2.95 (m, 2H), 3.79 (s, 3H), 6.67 (m, 2H), 7.05 (s, 1H), 7.20 (d, 1H), 11.66 (br s, 1H). MS m/z (TOF ES$^+$): 469 (M+1).

Compound 94

3-((13S,15R)-4-hydroxy-13-methyl-1-nitro-17-oxo-7,8,9,11,12,13,14,15,16,17-decahydro-6H-cyclopenta[a]phenanthren-15-yl)-N-(5-methylthiazol-2-yl)propanamide

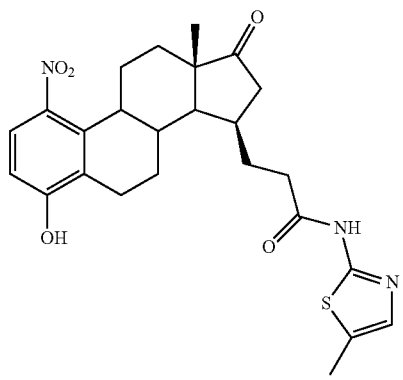 [SMILES: Cc1cnc(NC(=O)CC[C@@H]2CC(=O)[C@@]3(C)CCC4c5c([N+](=O)[O-])ccc(O)c5CCC4C23)s1]

Prepared from the compound 90 by using the general nitration method described for the compound 34. The nitration was achieved in the C-1 position.

¹H-NMR (CDCl₃): 1.08 (s, 3H), 1.26-3.20 (m, 21H), 6.98 (d, 1H), 7.07 (s, 1H), 7.93 (d, 1H), MS m/z (TOF ES+): 506 (M+Na).

Preparation of C-16-Hydroxymethylene Derivatives

C-16-hydroxymethylene derivatives were prepared using the general method: C-17 ketone (1 mmol) was dissolved into THF (5 ml), toluene (20 ml) and ethylformate (5 ml) under nitrogen atmosphere. Sodium hydride (4 mmol) was added and stirring was continued at rt overnight.

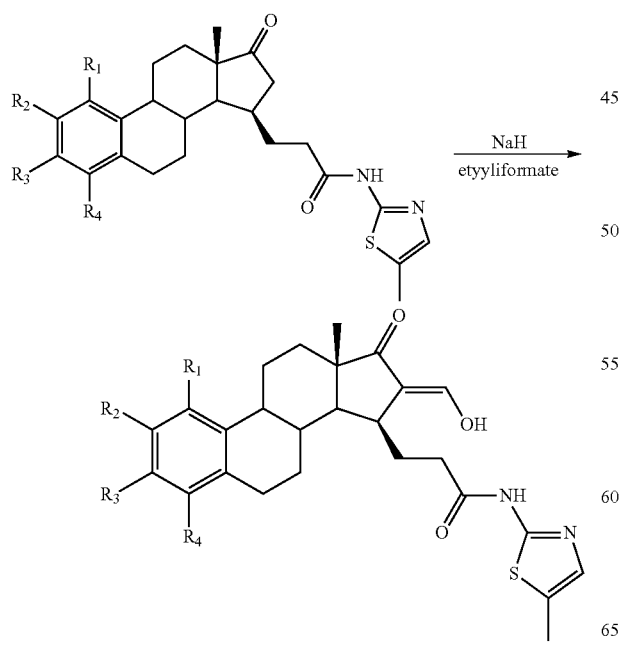

Compound 95

3-{(13S,15S)-3-Hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

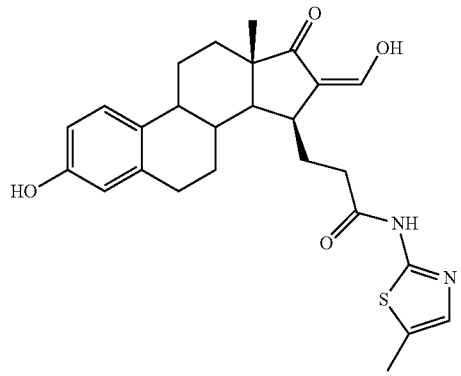 [SMILES: Cc1cnc(NC(=O)CC[C@@H]2/C(=C/O)C(=O)[C@@]3(C)CCC4c5ccc(O)cc5CCC4C23)s1]

The compound VII (100 mol-%) was dissolved into tetrahydrofuran (THF) (1 ml) under nitrogen atmosphere. Toluene (4 ml) was added to the reaction mixture followed by addition of ethyl formate (6000 mol-%). Sodium hydride (50%) (450 mol-%) was added and the reaction mixture was stirred overnight at rt. Additional amount of ethyl formate (6000 mol-%) and sodium hydride (450 mol-%) was added to the reaction mixture and stirring was continued overnight at rt. pH was adjusted to neutral with 0.5 N HCl and the solvents were evaporated. Water was added to the residue and extracted with EtOAc (3×10 ml). The combined organic phases were washed with water (10 ml) and brine (3×10 ml), dried over Na₂SO₄, filtered and evaporated. The product 95 was obtained in quantitative yield.

¹H-NMR (DMSO-d₆): 0.96 (s, 3H), 1.20-2.95 (m, 19H), 6.45 (s, 1H), 6.48 (d, 1H), 7.02 (d, 1H), 7.08 (s, 1H), 7.72 (s, 1H), 9.01 (s, 1H) 12.43 (br s, 1H). MS m/z (TOF ES⁺): 489 (M+Na)

Compound 96

3-{(13S,15S)-16-[1-Hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

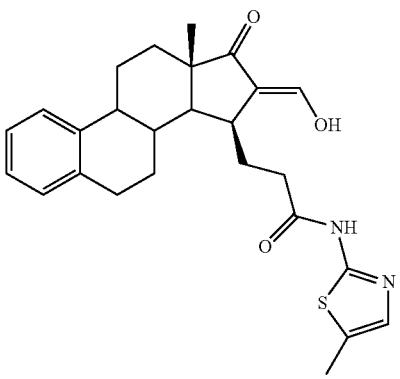 [SMILES: Cc1cnc(NC(=O)CC[C@@H]2/C(=C\O)C(=O)[C@@]3(C)CCC4c5ccccc5CCC4C23)s1]

Prepared by the method used for preparation of the compound 95 using the compound 83 as the starting material.

¹H-NMR (CDCl₃): 1.12 (s, 3H), 1.30-3.0 (m, 19H), 7.0-7.3 (m, 5H). MS m/z (TOF ES⁺): 451 (M+H).

Compound 97

3-{(13S,15S)-16-[1-Hydroxy-methylidene]-3-methoxy-13-methyl-17-oxo-7,8,9,11,12,13,14,15,16,17-decahydro-6H-cyclopenta[a]phenanthren-15-yl}-N-(5-methylthiazol-2-yl)propanamide

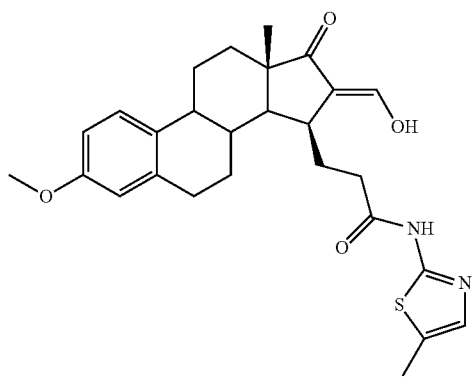 [SMILES: COc1ccc2c(c1)CCC1C2CC[C@]2(C)C(=O)/C(=C/O)[C@@H](CCC(=O)Nc3ncc(C)s3)C12]

Prepared by the method used for preparation of the compound 95 using the compound X as the starting material (quantitative yield).

¹H-NMR (CDCl₃+MeOH-d₄): 0.97 (t, 3H), 1.15-2.40 (m, 16H), 2.84 (m, 3H), 3.69 (s, 3H), 6.64 (s, 1H), 6.66 (d, 1H), 7.08 (s, 1H), 7.15 (d 1H), 8.13 (s, 1H). MS m/z (TOF ES⁺): 503 (M+Na), 481 (M+1).

Compound 98

3-{(13S,15S)-2-tert-Butyl-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

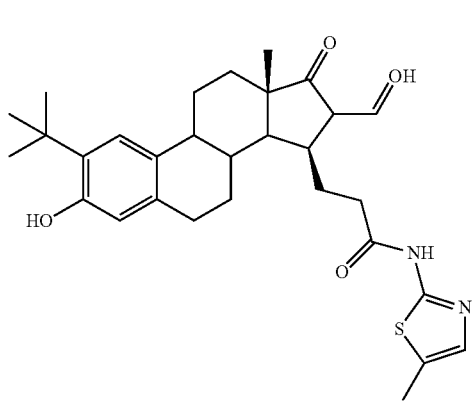 [SMILES: Cc1cnc(NC(=O)CC[C@@H]2C(C=O)C(=O)[C@@]3(C)CCC4c5cc(C(C)(C)C)c(O)cc5CCC4C23)s1]

Prepared by the method used for preparation of the compound 95 using the compound 31 as the starting material (74% yield).

¹H-NMR (DMSO-d₆): 0.99 (s, 3H), 1.05-3.00 (m, 32H), 6.46 (s, 1H), 7.00 (s, 1H), 7.09 (s, 1H), 7.58 (s, 1H), 8.95 (s, 1H), 12.01 (s, 1H); MS m/z (TOF ES⁺): 523 (M+1), 545 (M+Na).

Compound 99

3-{(13S,15S)-2-Bromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

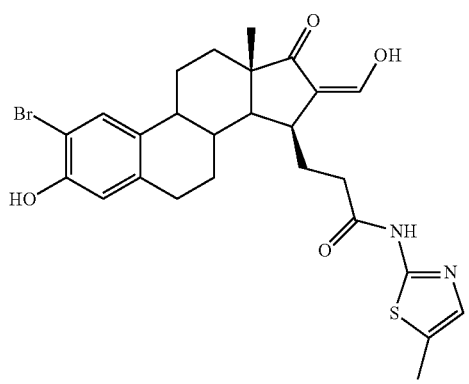 [SMILES: Cc1cnc(NC(=O)CC[C@@H]2/C(=C/O)C(=O)[C@@]3(C)CCC4c5cc(Br)c(O)cc5CCC4C23)s1]

Prepared by the method used for preparation of the compound 95 using the compound 56 as a starting material.

¹H-NMR (CDCl₃): 1.13 (s, 3H), 1.40-2.9 (m, 19H), 3.40 (s, 1H), 6.76 (d, 1H) 7.05 (s, 1H), 7.32 (d, 1H); MS m/z (TOF ES⁻): 543/545

Compound 100

3-{(13S,15S)-4-Bromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

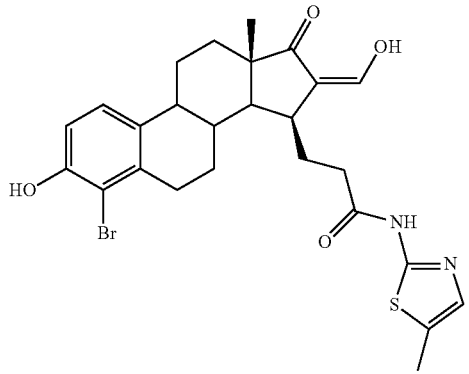 [SMILES: Cc1cnc(NC(=O)CC[C@@H]2/C(=C/O)C(=O)[C@@]3(C)CCC4c5ccc(O)c(Br)c5CCC4C23)s1]

Prepared by the method used for preparation of the compound 95 using the compound 57 as a starting material.

¹H-NMR (CDCl₃): 1.12 (s, 3H), 1.40-3.0 (m, 19H), 3.67 (s, 1H), 6.86 (d, 1H) 7.06 (s, 1H), 7.16 (d, 1H); MS m/z (TOF ES⁺): 545/547

Compound 101

3-{(13S,15S)-2,4-Dibromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

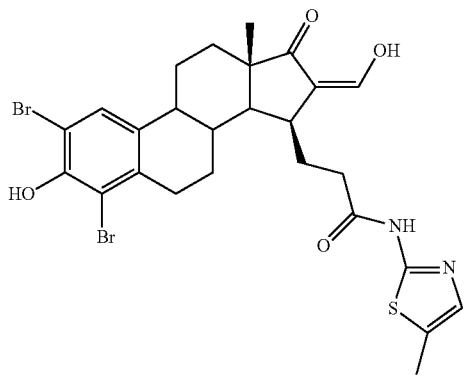 [SMILES: Cc1cnc(NC(=O)CC[C@@H]2/C(=C/O)C(=O)[C@@]3(C)CCC4c5cc(Br)c(O)c(Br)c5CCC4C23)s1]

Prepared by the method used for preparation of the compound 95 using the compound 58 as a starting material.

$^1$H-NMR (DMSO-d$_6$): 0.96 (s, 3H), 1.20-3.00 (m, 19H), 7.09 (s, 1H), 7.39 (s, 1H), 7.55 (s, 1H), 9.53 (br s, 1H), 11.95 (br s, 1H). MS m/z (TOF ES$^+$): 645/647/649 (M+Na)

Compound 102

3-{(13S,15S)-16-[1-hydroxy-methylidene]-2-iodo-3-methoxy-13-methyl-17-oxo-7,8,9,11,12,13,14,15,16,17-decahydro-6H-cyclopenta[a]phenanthren-15-yl}-N-(5-methylthiazol-2-yl)propanamide

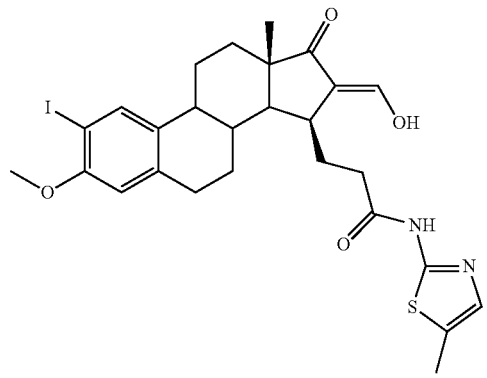 [SMILES: COc1cc2c(cc1I)C1CC[C@]3(C)C(=O)/C(=C/O)[C@@H](CCC(=O)Nc4ncc(C)s4)C3C1CC2]

Prepared by the general method used for preparation of the compound 95 using the compound 52 as a starting material (yield 74%).

$^1$H-NMR (CDCl$_3$): 1.14 (s, 3H), 1.20-2.97 (m, 20H), 3.85 (s, 3H), 6.57 (s, 1H) 7.07 (s, 1H), 7.63 (s, 1H); MS m/z (TOF ES$^+$): 607 (M+1)

Compound 103

3-{(13S,15S)-3-hydroxy-16-[1-hydroxy-methylidene]-13-methyl-2-nitro-17-oxo-7,8,9,11,12,13,14,15,16,17-decahydro-6H-cyclopenta[a]phenanthren-15-yl}-N-(5-methylthiazol-2-yl)propanamide

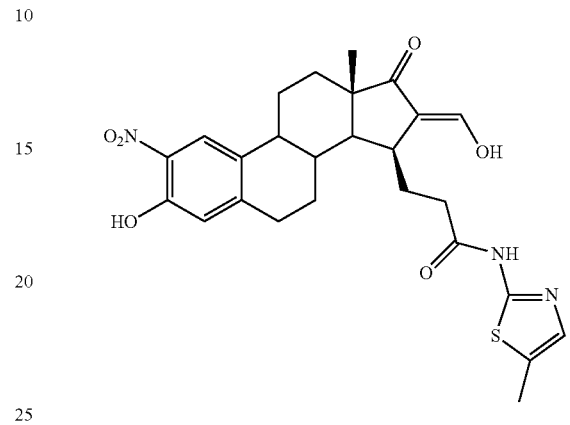

Prepared by the method used for preparation of the compound 95 using the compound 34 as a starting material.

$^1$H-NMR (CDCl$_3$): 1.14 (s, 3H), 1.20-3.05 (m, 19H), 6.88 (s, 1H), 7.04 (s, 1H), 7.23 (s, 1H), 7.97 (s, 1H). MS m/z (TOF ES$^+$): 534 (M+Na)

Compound 104

3-{(13S,15S)-3-hydroxy-16-[1-hydroxy-methylidene]-13-methyl-4-nitro-17-oxo-7,8,9,11,12,13,14,15,16,17-decahydro-6H-cyclopenta[a]phenanthren-15-yl}-N-(5-methylthiazol-2-yl)propanamide

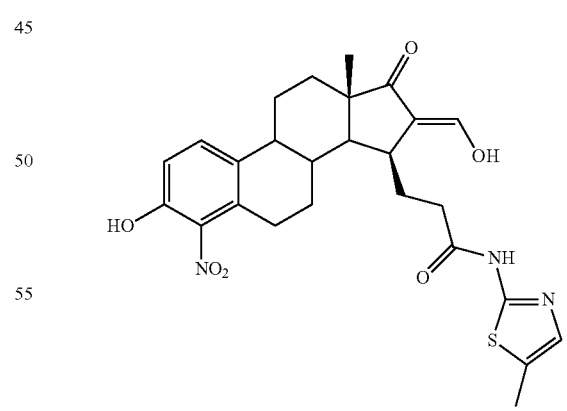

Prepared by the method used for preparation of the compound 95 using the compound 35 as a starting material.

$^1$H-NMR (CDCl$_3$): 1.14 (s, 3H), 1.30-3.35 (m, 19H), 6.97 (d, 1H), 7.06 (s, 1H), 7.44 (d, 1H). MS m/z (TOF ES$^+$): 534 (M+Na).

Compound 105

3-((13S,15R)-4-(tert-butyl)-13-methyl-17-oxo-7,8,9,11,12,13,14,15,16,17-decahydro-6H-cyclopenta[a]phenanthren-15-yl)-N-(5-methylthiazol-2-yl)propanamide

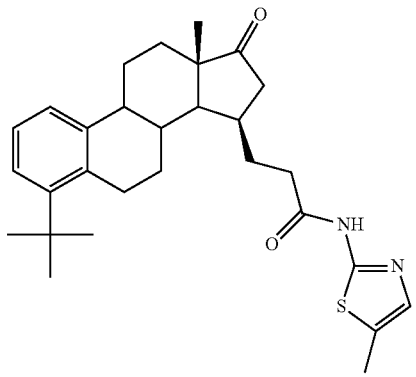 [SMILES: Cc1cnc(NC(=O)CC[C@@H]2CC(=O)[C@@]3(C)CCC4c5cccc(C(C)(C)C)c5CCC4C23)s1]

The compound 83 (50 mg, 0.12 mmol, 100 mol-%) was dissolved in dry DCM (2 ml) under nitrogen atmosphere. Tert-butanol (45 μl, 0.47 mmol, 400 mol-%) was added. Borontrifluoride etherate (0.7 ml, 0.47 mmol, 400 mol-%) was added slowly. Reaction was stirred at rt for 6 hours. Tert-butanol (0.45 ml) and $BF_3.Et_2O$ (0.67 ml) were added and stirring was continued overnight. Water (10 ml) was added and layers separated. Water layer was washed with DCM (3×5 ml). Combined organic layers were washed with water (3×10 ml), saturated sodium bicarbonate (3×10 ml) and brine (3×10 ml) and dried with $Na_2SO_4$. Solvent was evaporated. Crude product (130 mg) was purified by flash chromatography affording 27 mg of the compound.

$^1$H-NMR ($CDCl_3$): 1.06 (s, 3H), 1.31 (s, 9H), 1.40-2.20 (m, 10H), 2.33-2.67 (m, 9H), 2.92 (m, 2H), 7.04-7.33 (m, 4H), 12.32 (s, 1H).

Pharmacological Tests

The following tests are provided to demonstrate the present invention in illustrative way and should not be considered as limiting in the scope of invention. Further, the concentrations of the compound in the assays are exemplary and should not be taken as limiting. A person skilled in the art may define pharmaceutically relevant concentrations with method known in the art.

Inhibition of 17β-Hydroxysteroid Dehydrogenase Type 1 Enzyme

17β-HSD1 Production and Isolation:

Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994) Site-directed mutagenesis of the putative active site of human 17 β-hydroxysteroid dehydrogenase type 1. Biochem. J. 304: 289-293. Aliquots were stored frozen until determination of enzymatic activity.

Assay—Inhibition of Recombinant Human 17β-HSD1:

Recombinant protein (1 μg/ml) was incubated in 20 mM $KH_2PO_4$ pH 7.4 with 30 nM estrone (including 800 000 cpm/ml of $^3$H-estrone) and 1 mM NADPH for 30 min at RT, in the presence of the potential inhibitor at concentrations 1 μM or 0.1 μM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(\text{cpm estradiol in sample with inhibitor})/[(\text{cpm estrone in sample with inhibitor}) + (\text{cpm estradiol in sample with inhibitor})]\}}{[(\text{cpm estradiol in sample without inhibitor})/[(\text{cpm estrone in sample without inhibitor}) + (\text{cpm estradiol in sample without inhibitor})]\}}$$

Percent inhibition was calculated flowingly: % inhibition=100–% conversion

The values % inhibition were determined for exemplified compounds and the results are summarized in Table 2.

Inhibition of the 17β-Hydroxysteroid Dehydrogenase Type 2 Enzyme

17β-HSD2 Production and Isolation:

Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

- cells were dissolved into 40 ml of A-buffer (40 mM TRIS, pH8.0, 20% glycerol, 20 μM NAD, 0.4 mM PMSF, 150 mM NaCl, 0.5% dodecyl-β-maltoside+protease inhibitor cocktail)
- cells were sonicated
- lysate was incubated on ice for 15 min
- lysate was centrifuged 5000 rpm 15 min, +4° C.
- centrifugation of the supernatant 180 000 g 30 min, +4° C.
- pellet was dissolved into 8 ml of A-buffer
- not resuspended material was removed by centrifugation 5000 rpm 15 min, +4° C.
- the clear supernatant was divided into 100 μl aliquots and were stored frozen until determination of enzymatic activity.

The amount of 17β-HSD2 was analysed by immunoblotting and total protein concentration of each extract batch was determined.

Assay—Inhibition of Recombinant Human 17β-HSD2:

Recombinant protein (4 μg/ml) was incubated in 20 mM $KH_2PO_4$ pH 8.5 with 50 nM estradiol (including 800 000 cpm/ml of $^3$H-estradiol) and 1 mM NADH for 30 min at RT, in the presence of the potential inhibitor at concentrations 1 μM or 0.1 μM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estradiol to estrone was calculated according to the following formula:

$$\% \text{ conversion} = 100 \times \frac{\{(\text{cpm estrone in sample with inihibitor})/[(\text{cpm estradiol in sample with inhibitor}) + (\text{cpm estrone in sample with inhibitor})]\}}{[(\text{cpm estrone in sample without inhibitor})/[(\text{cpm estradiol in sample without inhibitor}) + (\text{cpm estrone in sample without inhibitor})]\}}.$$

Percent inhibition was calculated flowingly: % inhibition=100−% conversion

The values % inhibition were determined for exemplified compounds and the results are summarized in Table 2.

Estrogen Receptor Binding Assay

The binding affinity of the compounds of the invention to the estrogen receptor a (ERα) may be determined according to the in vitro ER binding assay described by Koffmann et al REF. Alternatively, an estrogen receptor binding assay may be performed according to international patent application WO2000/07996.

Estrogen Receptor Transactivation Assays

Compound of the invention showing binding affinity towards the estrogen receptor may be further tested with regard to their individual estrogenic or anti-estrogenic potential (Agonistic or antagonistic binding to the ERα or ERβ). The determination of the estrogen receptor antagonistic activity may be performed according to an in vitro assay system using the MMTV-ERE-LUC reporter system for example described in US patent application US2003/0170292.

Metabolic Stability Assay

The in vitro metabolic stability of the compounds of the invention was determined for exemplified compounds using human liver microsome and homogenate incubations. The incubation time points used with or without appropriate cofactors were 0 min and 60 min. Samples were collected at both time points and substrates were detected using LC/PDA/TOF-MS. In vitro metabolic stability (')/0 remaining after 60 min in human liver homogenate or microsomes) of the compounds were calculated and the results are summarized in Table 3.

Pharmacological Test Results

TABLE 2

| # | 17β-HDS1 Inhibition % at 1 μM | 17β-HSD2 Inhibition % at 1 μM |
| --- | --- | --- |
| VII | 97 | 7 |
| X | 96 | 3 |
| 1 | 92 | 13 |
| 2 | 95 | 11 |
| 4 | 82 | 3 |
| 5 | 92 | 4 |
| 7 | 80 | 3 |
| 8 | 81 | 0 |
| 10 | 98 | 1 |
| 11 | 87 | 0 |
| 11 | 88 | 2 |

TABLE 2-continued

| # | 17β-HDS1 Inhibition % at 1 μM | 17β-HSD2 Inhibition % at 1 μM |
| --- | --- | --- |
| 15 | 66 | 0 |
| 16 | 93 | 0 |
| 19 | 58 | 0 |
| 20 | 52 | 0 |
| 23 | 74 | 6 |
| 25 | 52 | 6 |
| 26 | 96 | 6 |
| 27 | 81 | 5 |
| 31 | 87 | 12 |
| 32 | 84 | 1 |
| 33 | 71 | 3 |
| 34 | 91 | 10 |
| 36 | 87 | 33 |
| 37 | 88 | 4 |
| 38 | 87 | 9 |
| 39 | 96 | 1 |
| 40 | 75 | 1 |
| 42 | 90 | 0 |
| 43 | 94 | 0 |
| 44 | 91 | 2 |
| 45 | 83 | 0 |
| 46 | 87 | 3 |
| 47 | 87 | 2 |
| 48 | 91 | 2 |
| 49 | 84 | 1 |
| 50 | 91 | 40 |
| 51 | 78 | 1 |
| 52 | 93 | 1 |
| 53 | 94 | 5 |
| 54 | 86 | 4 |
| 55 | 98 | 7 |
| 56 | 93 | 18 |
| 57 | 92 | 16 |
| 58 | 95 | 5 |
| 59 | 79 | 2 |
| 63 | 99 | 21 |
| 64 | 98 | 5 |
| 66 | 98 | 8 |
| 67 | 98 | 6 |
| 68 | 88 | 3 |
| 69 | 57 | 4 |
| 71 | 91 | 7 |
| 72 | 89 | 10 |
| 73 | 90 | 2 |
| 75 | 89 | 2 |
| 77 | 87 | 0 |
| 78 | 91 | 1 |
| 79 | 72 | 0 |
| 83 | 92 | 1 |
| 84 | 93 | 1 |
| 85 | 93 | 2 |
| 86 | 92 | 0 |
| 87 | 87 | 2 |
| 88 | 93 | 1 |
| 89 | 71 | 0 |
| 90 | 94 | 0 |
| 91 | 97 | 1 |
| 92 | 97 | 0 |
| 93 | 54 | 3 |
| 94 | 95 | 4 |
| 95 | 97 | 3 |
| 97 | 92 | 11 |
| 105 | 90 | 16 |

TABLE 3

| # | In vitro metabolic stability, % remaining after 60 min |
| --- | --- |
| VII | 13 |
| 2 | 25 |
| 3 | 30 |
| 5 | 50 |
| 30 | 74 |

TABLE 3-continued

| # | In vitro metabolic stability, % remaining after 60 min |
|---|---|
| 47 | 48 |
| 58 | 81 |
| 83 | 74 |

Utility of the Invention

Compounds of the invention show selective inhibitory potential of the 17β-HSD1 enzyme and little or no inhibitory activity to the 17β-HSD2 enzyme and therefor, and may be useful for the treatment of a steroid hormone dependent malign or benign disease or disorder, in particular for treatment and prevention of several estrogen dependent diseases and disorders. Further, compounds of the present invention may be useful for the treatment of diseases and disorders associated with increased levels of estradiol and which may be prevented, treated, and/or ameliorated by an inhibitor of 17β-HSD1 enzyme.

Examples of inflammatory diseases and conditions include, but are not limited to, breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Compounds of the present invention may be administered in an effective amount within the dosage range of about 0.1 μg/kg to about 300 mg/kg, in particular between 1.0 μg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention may be used alone or in combination i.e. administered simultaneously, separately or sequentially with other active ingredients. Compounds of the invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant.

Compounds may be formulated into a suitable composition; suitable administration forms include, for example, solutions, dispersions, suspensions, powders, capsules, tablet, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Furthermore, compounds of formula (I) can be used as synthesis intermediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:

1. A compound of formula (Ih)

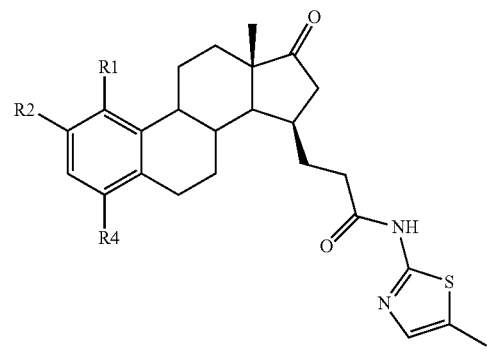

(Ih)

wherein
(i) R1 is selected from the group consisting of H, $NO_2$, OH, and $N(R')_2$;
(ii) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n N(R')_2$, OR', $(CH_2)_n OR'$, $CO_2R'$, CONHR', NHCOR", C(=NH)R", C(=N—OH)R" and COR";

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R" is $C_{1-6}$-alkyl, $C_{1-3}$-haloalkyl, or $C_{1-3}$-perhaloalkyl; and
n is 1 or 2;
or a pharmaceutically acceptable salt thereof.

2. A compound as claimed in claim 1, wherein R1 is H or $NO_2$.

3. A compound as claimed in claim 2, wherein R1 is H.

4. A compound as claimed in claim 1, wherein R2 is selected from the group consisting of H, halogen, branched $C_{3-6}$-alkyl, CN, $NO_2$, $NH_2$, $(CH_2)N(R')_2$, COR" and OH, wherein R' is methyl or both R's together with the nitrogen they are attached to form an 5 to 6 membered aliphatic or aromatic heterocyclic ring comprising 1 or 2 heteroatoms each independently selected from N and O.

5. A compound as claimed in claim 1, wherein R4 is selected from the group consisting of H, halogen, $NO_2$, $NH_2$, CN, and $NHCOCF_3$.

6. A compound as claimed in claim 1, wherein one or two of R1, R2 and R4 is independently selected from the group consisting of F, Cl, Br, I, OH, NH₂, and NO₂; or a pharmaceutically acceptable salt thereof.

7. A compound of formula (Ic), (Id), (Ie), or (If)

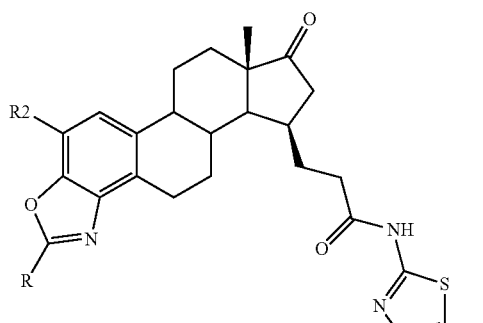
(Ic)

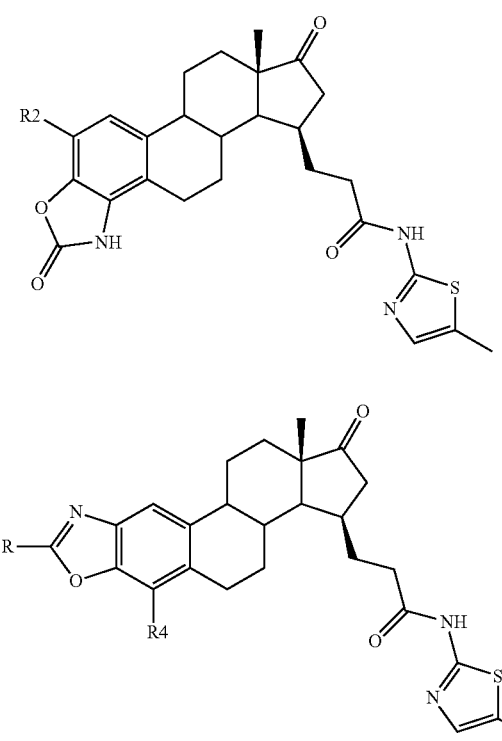
(Id)

(Ie)

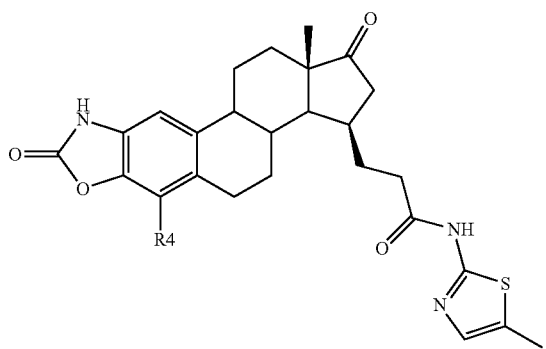
(If)

wherein R2 and R4 are selected from the group consisting of H, F, Cl, Br, and I, and R is H or methyl;
or a pharmaceutically acceptable salt thereof.

8. A compound as claimed in claim 7, having formula (Ie), or (If)

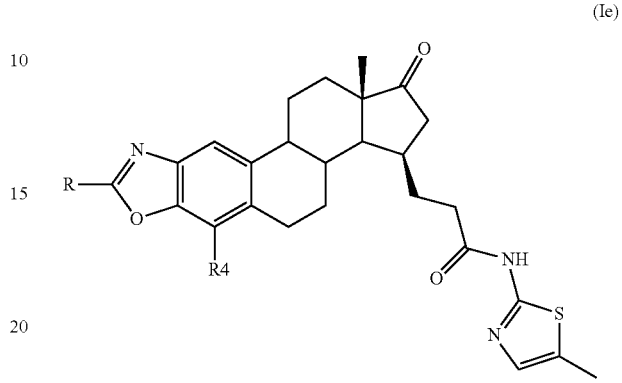
(Ie)

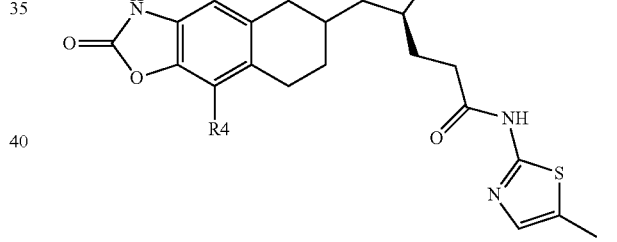
(If)

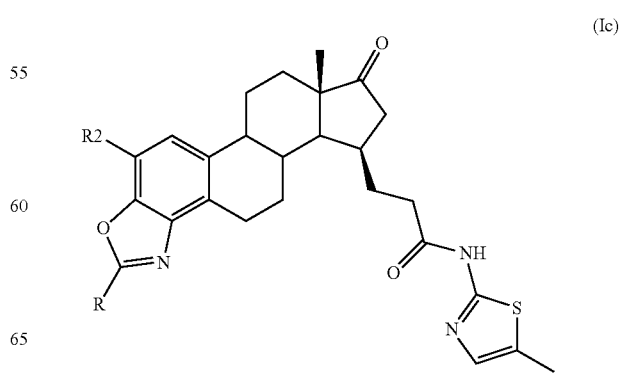

wherein R4 is selected from the group consisting of H, F, Cl, Br, and I, and R is H or methyl;
or a pharmaceutically acceptable salt thereof.

9. A compound as claimed in claim 7, having formula (Ic), or (Id)

(Ic)

143

-continued

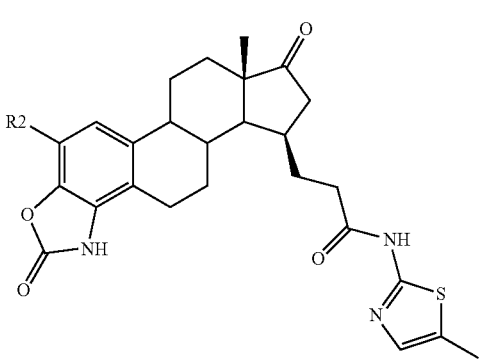

(Id)

wherein R2 is selected from the group consisting of H, F, Cl, Br, and I, and R is H or methyl;
or a pharmaceutically acceptable salt thereof.

10. A compound selected from the group consisting of:
Compound 46 3-((7aS,10R)-7a-methyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide;
Compound 47 3-((3R,12aS)-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;
Compound 48 3-((3R,12aS)-8,12a-dimethyl-1-oxo-2,3,3a,3b,4,5, 10b,11, 12,12a-decahydro-1H-cyclopenta[7,8]phenanthro[3,2-d]oxazol-3-yl)-N-(5-methylthiazol-2-yl)propanamide;
Compound 49 3-((7aS,10R)-2,7a-dimethyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide;
Compound 50 3-((3R,12aS)-12a-methyl-1,8-dioxo-2,3,3a,3b,4,5,8,9,10b,11,12,12a-dodecahydro-1H-cyclopenta[7,8]phenanthro[3,2-d]oxazol-3-yl)-N-(5-methylthiazol-2-yl)propanamide;
Compound 51 3-((7aS,10R)-7a-methyl-2,8-dioxo-2,5b,6,7,7a,8,9,10,10a,10b,11,12-dodecahydro-1H-cyclopenta[7,8]phenanthro[1,2-d]oxazol-10-yl)-N-(5-methylthiazol-2-yl)propanamide;
Compound 77 3-((3R,12aS)-6-chloro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;
Compound 78 3-((3R,12aS)-6-fluoro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide;
Compound 83 3-((13S,15R)-13-methyl-17-oxo-7,8,9,11,12,13,14,15,16,17-decahydro-6H-cyclopenta[a]phenanthren-15-yl)-N-(5-methylthiazol-2-yl)propanamide;
Compound 84 3-((13S,15R)-13-methyl-2-nitro-17-oxo-7,8,9,11,12,13,14,15,16,17-decahydro-6H-cyclopenta[a]phenanthren-15-yl)-N-(5-methylthiazol-2-yl) propanamide;
Compound 85 3-((13S,15R)-13-methyl-4-nitro-17-oxo-7,8,9,11,12,13,14,15,16,17-decahydro-6H-cyclopenta[a]phenanthren-15-yl)-N-(5-methylthiazol-2-yl) propanamide;
Compound 86 3-((13S,15R)-2-fluoro-13-methyl-17-oxo-7,8,9,11,12,13,14,15,16,17-decahydro-6H-cyclopenta[a]phenanthren-15-yl)-N-(5-methylthiazol-2-yl)propanamide;
Compound 87 3-((13S,15R)-2-amino-13-methyl-17-oxo-7,8,9,11,12,13,14,15,16,17-decahydro-6H-cyclopenta[a]phenanthren-15-yl)-N-(5-methylthiazol-2-yl)propanamide;
Compound 88 3-((13S,15R)-2-hydroxy-13-methyl-17-oxo-7,8,9,11,12,13,14,15,16,17-decahydro-6H-cyclopenta[a]phenanthren-15-yl)-N-(5-methylthiazol-2-yl) propanamide;
Compound 89 3-((13S,15R)-4-amino-13-methyl-17-oxo-7,8,9,11,12,13,14,15,16,17-decahydro-6H-cyclopenta[a]phenanthren-15-yl)-N-(5-methylthiazol-2-yl)propanamide;
Compound 90 3-((13S,15R)-4-hydroxy-13-methyl-17-oxo-7,8,9,11,12,13,14,15,16,17-decahydro-6H-cyclopenta[a]phenanthren-15-yl)-N-(5-methylthiazol-2-yl) propanamide;
Compound 94 3-((13S,15R)-4-hydroxy-13-methyl-1-nitro-17-oxo-7,8,9,11,12,13,14,15,16,17-decahydro-6H-cyclopenta[a]phenanthren-15-yl)-N-(5-methylthiazol-2-yl)propanamide; and
Compound 105 3-((13S,15R)-4-(tert-butyl)-13-methyl-17-oxo-7,8,9,11,12,13,14,15,16,17-decahydro-6H-cyclopenta[a]phenanthren-15-yl)-N-(5-methylthiazol-2-yl)propanamide;
or a pharmaceutically acceptable salt thereof.

11. A pharmaceutical composition comprising an effective amount of one or more compounds as claimed in claim 1, or a pharmaceutically acceptable salt thereof, together with one or more pharmaceutically acceptable excipient(s).

12. The pharmaceutical composition as claimed in claim 11, further comprising one or more other active ingredients.

13. A method of alleviating or ameliorating disease or disorder selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts, comprising administering a compound as claimed in claim 1, or a pharmaceutically acceptable salt thereof, to a patient in need thereof.

14. A pharmaceutical composition comprising an effective amount of one or more compounds as claimed in claim 7, or a pharmaceutically acceptable salt thereof, together with one or more pharmaceutically acceptable excipient(s).

15. The pharmaceutical composition as claimed in claim 14, further comprising one or more other active ingredients.

16. A method of alleviating or ameliorating disease or disorder selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts, comprising administering a compound as claimed in claim 7, or a pharmaceutically acceptable salt thereof, to a patient in need thereof.

\* \* \* \* \*